(12) United States Patent
Daifuku et al.

(10) Patent No.: US 7,772,197 B2
(45) Date of Patent: Aug. 10, 2010

(54) 1,3,5-TRIAZINES FOR TREATMENT OF VIRAL DISEASES

(75) Inventors: Richard Daifuku, Mercer Island, WA (US); Alexander Gall, Woodinville, WA (US); Dmitri Sergueev, Kirkland, WA (US)

(73) Assignee: 1,3,5-Triazines for Treatment of Viral Diseases, Redmond, WA (US)

( * ) Notice: Subject to any disclaimer, the term of this patent is extended or adjusted under 35 U.S.C. 154(b) by 655 days.

(21) Appl. No.: 10/670,915

(22) Filed: Sep. 24, 2003

(65) Prior Publication Data

US 2004/0127436 A1 Jul. 1, 2004

Related U.S. Application Data

(60) Provisional application No. 60/413,337, filed on Sep. 24, 2002.

(51) Int. Cl.
*A61K 31/706* (2006.01)
*C07H 19/12* (2006.01)

(52) U.S. Cl. ...................................... 514/43; 536/28.3

(58) Field of Classification Search ................ 514/395, 514/12, 232.8, 307, 336, 352, 388, 50, 48; 536/23.7, 28.4, 28.1, 28.3; 544/106, 131, 544/140; 549/282; 548/331.5

See application file for complete search history.

(56) References Cited

U.S. PATENT DOCUMENTS

| 3,988,314 | A |   | 10/1976 | Argoudelis et al. |
| 4,140,850 | A | * | 2/1979 | Wierenga ................... 536/27.1 |
| 4,171,431 | A |   | 10/1979 | Skulnick |
| 4,587,117 | A |   | 5/1986 | Edgren et al. |
| 4,666,892 | A |   | 5/1987 | Fox et al. |
| 4,788,181 | A | * | 11/1988 | Driscoll et al. ................. 514/49 |
| 5,324,831 | A |   | 6/1994 | Marquez et al. |
| 5,574,142 | A | * | 11/1996 | Meyer et al. ............... 536/23.1 |
| 5,696,277 | A |   | 12/1997 | Hostetler et al. |
| 6,852,334 | B1 |   | 2/2005 | Cullis et al. |
| 2004/0127436 | A1 |   | 7/2004 | Daifuku et al. |
| 2007/0142310 | A1 |   | 6/2007 | Daifuku et al. |
| 2007/0207973 | A1 |   | 9/2007 | Daifuku et al. |
| 2007/0219200 | A1 |   | 9/2007 | Daifuku et al. |
| 2008/0033172 | A1 |   | 2/2008 | Daifuku et al. |
| 2008/0249097 | A1 |   | 10/2008 | Daifuku et al. |

FOREIGN PATENT DOCUMENTS

WO  WO 95/28940 A1  11/1995

OTHER PUBLICATIONS

McGuigan et al., "Synthesis and anti-HIV activity of some novel substituted dialkyl phosphate derivatives of AZT and ddCyd" Antiviral Chemistry and Chemotherapy (1990) vol. 1, No. 6, pp. 355-360.*

McGuigan et al. (2) "Aryl phosphate derivatives of AZT retain activity against HIV1 in cell lines whih are resistant to the action of AZT" Antiviral Research (1992) vol. 17, pp. 311-321.*
Powell et al. "Biochemical pharmacology of 5,6-dihydro-5-azacytidine (DHAC) and DNA hypomethylation in tumor (L1210)-bearing mice" Cancer Chemother Pharmacol (1988) vol. 21, pp. 117-121.*
Bukrinskaia et al., "Comparative Effects of histones and 6-azauridine on the reproduction of myxoviruses," *Vopr. Virusol*, Sep. 1968, pp. 549-554, vol. 13, No. 9.
Daifuku, R., et al., "Stealth Nucleosides: Mode of Action and Potential Use in the Treatment of Viral Diseases," *Biodrugs*, 2003, pp. 169-177, vol. 17, No. 3.
Bouchard et al., "5-azacytidine and 5-azadeoxycytidine inhibit human immunodeficiency virus type 1 replication in vitro." *Antimicrobial Agents and Chemotherapy*, vol. 34, pp. 206-209, Feb. 1990.
Halle, "5-azacytidine as a mutagen for arboviruses." *Journal of Virology*., pp. 1228-1229, Oct. 1968.
Johnson-Thompson et al., "Azapyrimidine analogues: inhibition of viral DNA synthesis and protein synthesis in SV40 infected BSC-1 cells." *In Vitro Cellular & Developmental Biology*, vol. 24, No. 11, pp. 1114-1120, Nov. 1988.
Kedzierska et al., "Cytokines and HIV-1: interactions and clinical implications." *Antiviral Chemistry & Chemotherapy*, vol. 12, pp. 133-150, 2001.
Novotny et al., "Polarographic reduction and potential carcinogenity of substituted 1,3,5-triazine nucleosides." *Collec. Czech. Chem. Commun.* vol. 60, pp. 1469-1475, 1995.
Pathak et al., "5-azacytidine and RNA secondary structure increase the retrovirus mutation rate." *Journal of Virology*, pp. 3093-3100, May 1992.
Pískala et al., "Nucleic acids components and their analogues. LI. Synthesis of 1-glycosyl derivatives of 5-azauracil and 5-azacytosine." *Collec. Czech. Chem. Commun.*, vol. 29, pp. 2060-2076, 1964.
Pískala et al., "Synthesis, molecular conformation and biological activity of 6-animo-5-azacytidine." *Collec. Czech. Chem. Commun.*, vol. 54, pp. 2502-2512, 1989.
Schuster et al., "Analogues of pyrimidine base precursors as antophytoviral agents." *Antiviral Research*, 7, pp. 179-184, 1987.
Sierra et al., "Response of foot-and-mouth disease virus to increased mutagenesis: influence of viral load and fitness in loss of inf Scheme 1

5-Azacytidine (1)

2'-Deoxy-5-azacytidine (2)

5-Azauridine (3)

5,6-Dihydro-5-azauridine (4)

Scheme 2

Scheme 3

Scheme 4

Scheme 5

Scheme 6

Scheme 7

Scheme 8

R = H, CH₃
R₁ = H, OH

Scheme 9

Scheme 10

Scheme 11

5-Azacytidine (1)

23

24

2'-Deoxy-5-azauridine (25)

26

1,3,5-TRIAZINES FOR TREATMENT OF VIRAL DISEASES

CROSS-REFERENCE TO RELATED APPLICATIONS

This is a non-provisional filing of U.S. Provisional Application No. 60/413,337, filed Sep. 24, 2002, the disclosure of which is incorporated herein by reference in its entirety for all purposes.

BACKGROUND OF THE INVENTION

RNA viral diseases are responsible for the vast majority of viral morbidity and mortality of viral diseases of mankind, including AIDS, hepatitis, rhinovirus infections of the respiratory tract, flu, measles, polio and others. There are a number of chronic persistent diseases caused by RNA or DNA viruses that replicate through an RNA intermediate which are difficult to treat, such as hepatitis B and C, and T-cell human leukemia. Many common human diseases are caused by RNA viruses that are replicated by a viral encoded RNA replicase. Included in this group are influenza (Zurcher, et al., *J. Gen. Virol.* 77:1745 (1996), dengue fever (Becker, *Virus-Genes* 9:33 (1994), and rhinovirus infections (Horsnell, et al., *J. Gen. Virol.,* 76:2549 (1995). Important RNA viral diseases of animals include feline leukemia and immunodeficiency, *Visna maedi* of sheep, bovine viral diarrhea, bovine mucosal disease, and bovine leukemia. Although some vaccines are available for DNA viruses, diseases such as hepatitis B are still prevalent. Hepatitis B is caused by a DNA virus that replicates its genome through a RNA intermediate (Summers and Mason, *Cell* 29:4003 (1982). While an effective vaccine exists as a preventive, there is no efficacious treatment for chronic persistent HBV infection.

Chain terminating nucleoside analogs have been used extensively for the treatment of infections by DNA viruses and retroviruses. These analogs are incorporated into DNA by DNA polymerases or reverse transcriptases. Once incorporated, they cannot be further extended and thus terminate DNA synthesis. Unfortunately, there is immediate selective pressure for the development of resistance against such chain terminating analogs that results in development of mutations in the viral polymerase that prevent incorporation of the nucleoside analog.

An alternative strategy is to utilize mutagenic deoxyribonucleosides (MDRN) or mutagenic ribonucleosides (MRN) that are preferentially incorporated into a viral genome. MDRN are incorporated into DNA by viral reverse transcriptase or by a DNA polymerase enzyme. MRN are incorporated into viral RNAs by viral RNA replicases. As a result, the mutations in the viral genome are perpetuated and accumulated with each viral replication cycle. With each cycle of viral infection, there ensues a chain like increase in the number of mutations in the viral genome. Eventually the number of mutations in each viral genome is so large that no active virally encoded proteins are produced.

5-aza-2'-deoxycytidine (5-aza-dC) is an antineoplastic agent that has been tested in patients with leukemia and is thought to act predominantly by demethylating DNA. 5-azacytidine (5-aza-C) has also been used to treat patients with leukemia. Methylation is thought to silence tumor growth suppressor and differentiation genes. Interestingly deamination of 5-aza-dC to 5-aza-2'-deoxyuridine (5-aza-dU) has been shown to result in loss of antineoplastic activity (see e.g., Momparler, et al., *Leukemia.* 11:1-6 (1997)).

5-aza-cytidine (5-aza-C) has also been used to treat patients with leukemia. Both 5-aza-C and 5-aza-dC were shown to inhibit HIV replication in vitro, although the mechanism of action was not determined (see e.g., Bouchard et al, *Antimicrob. Agents Chemother.* 34: 206-209 (2000)). More recently, 5-aza-C has been shown to be mutagenic to foot-and-mouth disease virus (see e.g., Sierra et al., *J. Virol.* 74(18): 8316-8323 (2000)). Both 5-aza-C and 5-aza-dC are unstable compounds. 5-aza-dC is rapidly degraded upon reconstitution. At pH 7.0, a 10% degradation occurs at temperatures of 25° C. and 50° C. after 5 and 0.5 hours, respectively (see e.g., Van Groeningen et al., *Cancer Res.* 46:4831-4836 (1986)). Thus, therapeutic use of 5-aza-C and 5-aza-dC is limited for treatment of both viral diseases and cancer. The present invention solves this and other problems.

BRIEF SUMMARY OF THE INVENTION

The present invention provides a genus of nucleoside or nucleotide analogues and method of using the analogues as antiviral and anti-cancer chemotherapeutic agents.

Thus, in a first aspect, there is provided a compound according to Formula I:

(I)

In Formula I, the dashed circle indicates that the ring system may include one or more double bonds at any position, such that the valence of the intra-annular atoms is satisfied. The ring system may be aromatic (e.g., heteroaryl) or non-aromatic. The substituents $R^2$, $R^7$, $R^8$ are present or absent as dictated by the application of the laws of valency to a selected ring structure.

The symbol Y represents C, CH or N, and the symbol Z represents C, CH or B. $R^1$ is a member selected from H, acyl, $OR^9$, $SR^9$, $NR^9NHR^{10}$, $NR^9R^{10}$, =O and $=NR^9$, in which $R^9$ and $R^{10}$ are members independently selected from H, substituted or unsubstituted alkyl, acyl, substituted or unsubstituted heteroalkyl and substituted or unsubstituted aryl.

The symbol $R^2$ represents a substituent that is a member selected from H, acyl, substituted or unsubstituted alkyl, $OR^{11}$, $SR^{11}$, $NR^{11a}$, $NR^{12a}$, halogen, and =O. The symbol $R^{11}$ represents a member selected from H, substituted or unsubstituted alkyl, substituted or unsubstituted heterocycloalkyl, or substituted or unsubstituted heteroaryl. $R^{11a}$ and $R^{12a}$ are members independently selected from H, substituted or unsubstituted alkyl, substituted or unsubstituted heteroalkyl, substituted or unsubstituted aryl and substituted or unsubstituted heteroaryl.

$R^3$ is a member selected from H, acyl, substituted or unsubstituted alkyl, $NR^{12}R^{13}$, $NR^{12}OR^{13}$, $SR^{12}$, (=O) and $OR^{12}$. The symbols $R^{12}$ and $R^{13}$ represent members independently selected from H, substituted or unsubstituted alkyl, acyl, substituted or unsubstituted heteroalkyl, substituted or unsubstituted aryl or substituted or unsubstituted heteroaryl.

$R^4$ and $R^{4a}$ are members independently selected from H, halogen, OMe and OH. In a preferred embodiment, the halogen is F.

$R^5$ and $R^6$ are members independently selected from H, and $OR^{14}$. The symbol $R^{14}$ represents H, substituted or unsubstituted alkyl, acyl, substituted or unsubstituted heteroalkyl, or substituted or unsubstituted aryl and $P(O)(R^{15})(R^{16})$. $R^{15}$ and $R^{16}$ are independently selected from $OR^{17}$, $NR^{17}R^{18}$, substituted or unsubstituted alkyl and substituted or unsubstituted nucleosides. $R^{17}$ and $R^{18}$ are independently selected from H, $CH_2CH$ CN, substituted or unsubstituted alkyl, substituted or unsubstituted heteroalkyl, substituted or unsubstituted aryl and substituted or unsubstituted heteroaryl.

A member selected from $R^5$ and $R^3$; $R^6$ and $R^3$; and $R^{15}$ and $R^{16}$ together with the atoms to which they are attached, are optionally joined to form a ring system selected from substituted or unsubstituted cycloalkyl and substituted or unsubstituted heterocycloalkyl. In an exemplary embodiment, the ring system is a 5 or 6 membered ring system.

$R^7$ and $R^8$ are independently selected from H, acyl, substituted or unsubstituted alkyl. $R^1$ and $R^8$, together with the atoms to which they are attached are optionally joined into a ring system selected from substituted or unsubstituted cycloalkyl and substituted or unsubstituted heterocycloalkyl.

In another aspect of the present invention, the nucleoside and nucleotide analogues (e.g., the compounds of Formula I) of the present invention are used for treating a viral disease by administering a therapeutically effective amount of a compound of Formula I to a patient with a viral disease. In some embodiments, the compounds are given orally. In other embodiments, the compound is given in an enteric formulation. In a further embodiment, the compound is delivered in an oral osmotic drug delivery device.

When the compounds are given orally, it is generally preferred that they have a bioavailability that is greater than about 15%, more preferably greater than about 20% of the administered dose. In an exemplary embodiment, the compound is formulated as an acid addition salt, e.g. a quaternary ammonium salt. The salt is generally formed by contacting the compound with a mineral or an organic acid. In a preferred embodiment, the acid is a carboxylic acid, such as palmitic acid.

The viral disease can be a viral disease caused by an RNA virus, a DNA virus, or a retrovirus. In some embodiments, the viral disease is caused by HIV. In a further embodiment, the HIV strain is resistant to nucleotide reverse transcriptase inhibitors or other treatments of HIV infection, including non-nucleoside reverse transcriptase inhibitors, or protease inhibitors. In other embodiments, the viral disease is caused by a virus of the Flaviviridae family. In a further embodiment the viral disease is hepatitis C. In other embodiments, the viral disease is caused by a virus of the Paramyxoviridae family. In a further aspect, the virus is hepatitis B virus or smallpox/vaccinia virus.

In another aspect of the present invention the compounds of Formula I are used to treat treat cancer, e.g., hematopoetic cancers.

Other aspects, objects and advantages of the present invention will be apparent from the detailed description that follows.

DETAILED DESCRIPTION OF THE INVENTION

Introduction

Figure 1:
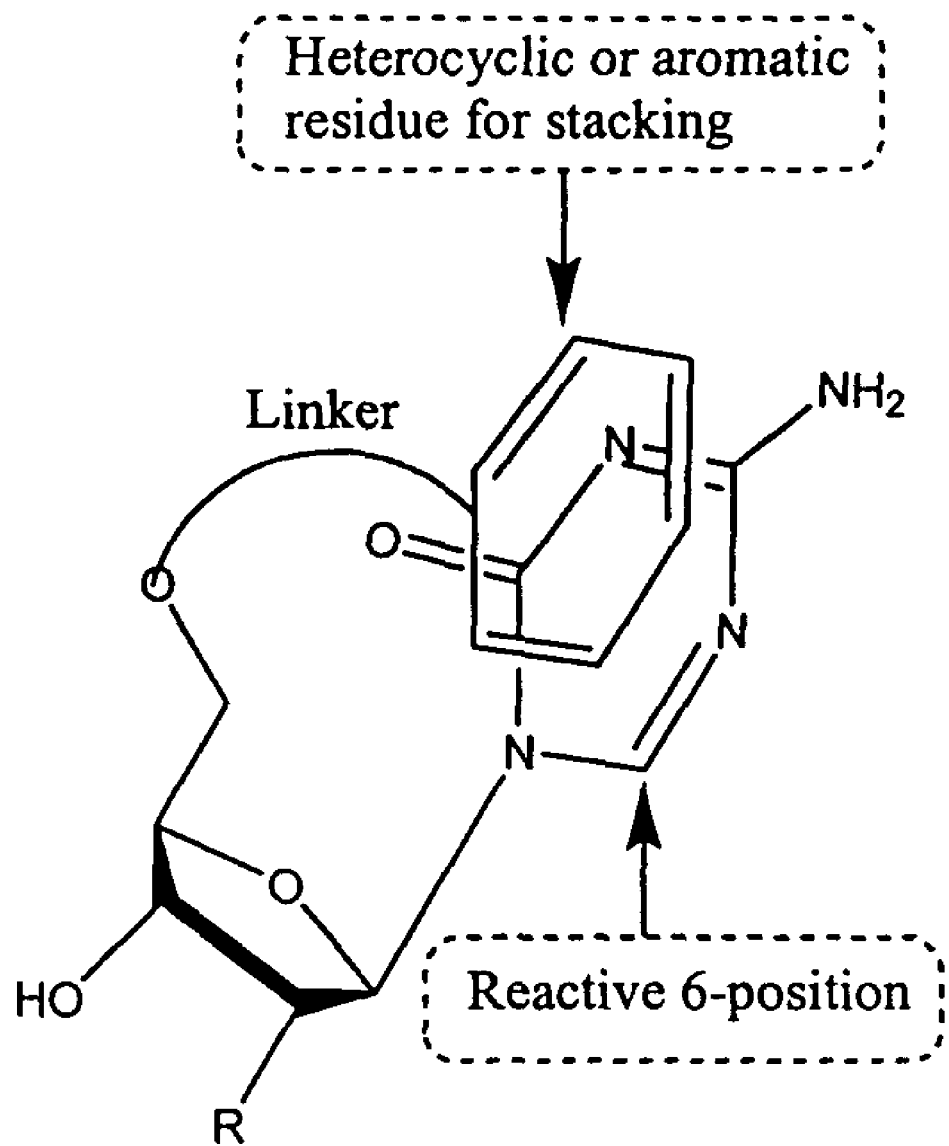
FIG. 1 is an illustration of the hydrophobic-hydrophobic stacking interactions of selected compositions of the invention.

The present invention is directed to a method of inducing viral mutagenesis, using hydrolytically stable derivatives and formulations of 5-aza-cytidine, 5-aza-2'-deoxycytidine and derivatives and variants thereof, which is useful in cell culture as well as in therapy for animals and humans. This method is advantageous in that it is useful against DNA or RNA viruses (i.e., viruses that have DNA or RNA genomes). In one embodiment, the methods of the invention are advantageous when used to target RNA viruses (viruses with an RNA genome), and retroviruses or other viruses otherwise replicated by an RNA intermediate. In another embodiment, the methods of the invention are advantageous for targeting DNA viruses such as hepatitis B virus, herpes viruses, and papilloma viruses. Without being held to a mechanism of action, in one embodiment, the methods of the invention utilize miscoding nucleosides and nucleotides that are incorporated into both viral encoded and cellular encoded viral genomic nucleic acids, thereby causing miscoding in progeny copies of the genomic virus, e.g., by tautomerism, which promotes base mispairing (see, e.g., Moriyama et al., *Nucleic Acids Symposium* 42: 131-132 (1999); Robinson et al., *Biochemistry* 37: 10897-10905 (1998); Anensen et al., *Mutation Res.* 476: 99-107 (2001); Lutz et al., *Bioorganic & Medicinal Chem. Letts.* 8: 499-504 (1998); and Klungland et al., *Toxicology Letts.* 119: 71-78 (2001)).

The virus may be one in which the viral genomic nucleic acid is integrated into the cellular genome. Examples of viruses that integrate their cellular genome include, but are not limited to, retroviruses. In one particularly preferred embodiment, the virus is HIV. Other preferred viruses include HIV-1, HIV-2, HTLV-1, HTLV-II, and SIV. In another embodiment, the virus is a DNA virus such as hepatitis B virus, herpes viruses (e.g., HSV, CMV, EBV), smallpox virus, or papilloma virus (e.g., HPV). Alternatively, the viral genome can be episomal. These include many human and animal pathogens, e.g., flaviviruses such as dengue fever, West Nile virus, and yellow fever, pestiviruses (a genus of the Flaviviridae family) such as BVDV (bovine viral diarrhea virus), hepatitis C viruses (also a genus of the Flaviviridae family), filoviruses such as ebola virus, influenza viruses, parainfluenza viruses, including respiratory syncytial virus, measles, mumps, the picornaviruses, including the echoviruses, the coxsackieviruses, the polioviruses, the togaviruses, including encephalitis, coronoviruses, rubella, bunyaviruses, reoviruses, including rotaviruses, rhabdoviruses, arenaviruses such as lymphocytic choriomeningitis as well as other RNA viruses of man and animals.

Retroviruses that can be targeted include the human T-cell leukemia (HTLV) viruses such as HTLV-1 and HTLV-2, adult T-cell leukemia (ATL), the human immunodeficiency viruses such as HIV-1 and HIV-2 and simian immunodeficiency virus (SIV). In some embodiments, the HIV virus is resistant to non-nucleoside reverse transcriptase inhibitors. In certain embodiments, the virus is hepatitis A or hepatitis B. See, e.g., Fields Virology (3rd ed. 1996). Further information regarding viral diseases and their replication can be found in White and Fenner, Medical Virology 4th ed. Academic Press (1994) and in Principles and Practice of Clinical Virology, ed. Zuckerman, Banatvala and Pattison, John Wiley and Sons (1994). In addition, the compounds of the invention can be used to treat cancer.

Assays for detecting the mutagenic potential of a nucleoside or nucleotide analog are provided (see, e.g., Example 1). In the assays, the nucleoside or nucleotide analog is incorporated into a viral nucleic acid in the presence of a nucleic acid template, the nucleic acid synthesized by a cellular or viral polymerase, and a determination is made regarding whether the incorporation causes a mutation in a progeny virus. Optionally, naturally occurring (i.e., G, A, U, and/or C) nucleotides are also incorporated into the nucleic acid polymer. The method optionally comprises comparing the rate of incorporation of the nucleoside or nucleotide analog and any naturally occurring ribonucleoside in the assay into the nucleic acid. For additional examples of assays, see, e.g., U.S. Pat. No. 6,132,776, U.S. Pat. No. 6,130,036, U.S. Pat. No. 6,063,628, and U.S. Pat. No. 5,512,431 and U.S. patent application Ser. Nos. 10/226,799 and 60/314,728, which are incorporated herein by reference in their entirety.

Exemplary compounds for use in the methods of the invention include 5-aza-cytidine, 5-aza-2'-deoxycytidine, and derivatives and variants thereof.

DEFINITIONS

Where substituent groups are specified by their conventional chemical formulae, written from left to right, they equally encompass the chemically identical substituents which would result from writing the structure from right to left, e.g., —CH$_2$O— is intended to also recite —OCH$_2$—; —NHS(O)$_2$— is also intended to represent. —S(O)$_2$HN—, etc.

As used herein, "linking member" refers to an alkylene unit or a covalent chemical bond that includes at least one heteroatom. Exemplary linking members include —C(O)NH—, —C(O)O—, —NH—, —S—, —O—, and the like.

The term "targeting group" is intended to mean a moiety that is (1) able to direct the entity to which it is attached (e.g., therapeutic agent or marker) to a target region, e.g. cell; or (2) is preferentially activated at a target region, for example a region of viral infection. The targeting group can be a small molecule, which is intended to include both non-peptides and peptides. The targeting group can also be a macromolecule, which includes saccharides, lectins, receptors, ligand for receptors, proteins such as BSA, antibodies, and so forth.

The term "alkyl," by itself or as part of another substituent, means, unless otherwise stated, a straight or branched chain, or cyclic hydrocarbon radical, or combination thereof, which may be fully saturated, mono- or poly-unsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups, which are limited to hydrocarbon groups, are termed "homoalkyl".

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

"Acyl" refers to a moiety that is a residue of a carboxylic acid from which an oxygen atom is removed, i.e., —C(O)R, in which R is substituted or unsubstituted alkyl, substituted or unsubstituted heteroalkyl, substituted or unsubstituted heterocycloalkyl, substituted or unsubstituted aryl or substituted or unsubstituted heteroaryl.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, and —CH═CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both (O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, typically aromatic, hydrocarbon substituent, which can be a single ring or multiple rings (up to three rings), which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O) NR"R'", —NR"C(O)$_2$R', —NR—C(NR'R" R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O) $CH_3$, —C(O)$CF_3$, —C(O)$CH_2OCH_3$, and the like).

Similar to the substituents described for the alkyl radical, substituents for the aryl and heteroaryl groups are varied and are selected from, for example: halogen, —OR', =O, =NR', =N—OR', —NR'R", —SR', -halogen, —SiR'R" R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted ($C_1$-$C_6$)alkyl.

As used herein, the term "heteroatom" includes oxygen (O), nitrogen (N), sulfur (S) and silicon (Si).

"Moiety" refers to the radical of a molecule that is attached to another moiety.

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocyclyl groups.

"Reactive functional group," as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids, isonitriles, amidines, imides, imidates, nitrones, hydroxylamines, oximes, hydroxamic acids, thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

"Protecting group," as used herein refers to a portion of a substrate that is substantially stable under a particular reaction condition, but which is cleaved from the substrate under a different reaction condition. A protecting group can also be selected such that it participates in the direct oxidation of the aromatic ring component of the compounds of the invention. For examples of useful protecting groups, see, for example, Greene et al., PROTECTIVE GROUPS IN ORGANIC SYNTHESIS, John Wiley & Sons, New York, 1991.

As used herein the term "nucleoside," includes both the naturally occurring nucleosides and modifications thereof. Modifications include, but are not limited to, those providing chemical groups that incorporate additional charge, polarizability, hydrogen bonding, and electrostatic interaction to the nucleosides. Such modifications include, but are not limited to, peptide nucleic acids (PNAs), 2'-position sugar modifications, 5-position pyrimidine modifications, 8-position purine modifications, modifications at exocyclic amines, substitution of 4-thiouridine, substitution of 5-bromo or 5-iodouracil; backbone modifications, methylations, isobases, such as isocytidine and isoguanidine and the like. "Nucleosides" can also include non-natural bases, such as, for example, nitroindole. Modifications can also include derivitization with a quencher, a fluorophore or another moiety. "Nucleotides" are phosphate esters of nucleosides. Many modifications of nucleosides can be also be practiced on nucleotides.

The symbol , whether utilized as a bond or displayed perpendicular to a bond indicates the point at which the displayed moiety is attached to the remainder of the molecule, solid support, etc.

The term "pharmaceutically acceptable salts" includes salts of the active compounds prepared with relatively non-toxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, palmitic and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S ENCYCLOPEDIA OF PRACTICAL ORGANIC CHEMISTRY $5^{TH}$ ED., Longman Scientific and Technical Ltd., Essex, 1991, pp. 809-816; and Heller, *Acc. Chem. Res.* 23: 128 (1990).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The term "viral disease" refers to a condition caused by a virus. A viral disease can be caused by a DNA virus, an RNA virus, or by a retrovirus. In some embodiments, viral diseases include virus of the Flavaviridae family. The family Flaviviridae includes the three genera of the family, the flaviviruses, the pestiviruses (e.g., BVDV), and the hepatitis C viruses (e.g., HCV). The family Paramyxoviridae includes without limitation, parainfluenza virus, respiratory syncytial virus, Newcastle Disease virus, mumps virus and measles virus. DNA virus includes the family Poxyiridae. Poxyiridae family members include vaccinia virus and variola virus, which can cause small pox. DNA virus includes, but is not limited to, the Hepatitis B virus, which replicates its genome through an RNA intermediate. Retrovirus includes HIV-1, HIV-2, HTLV-1, HTLV-II, and SIV.

In a preferred embodiment, the compounds of the invention are used to treat an HIV strain that is resistant to nucleoside reverse transcriptase inhibitors (NRTI).

The four "naturally occurring nucleotides" in RNA and DNA contain adenine, guanine, uracil, thymine or cytosine. Nucleotides which are complementary to one another are those that tend to form complementary hydrogen bonds between them and, specifically, the natural complement to A is U or T, the natural complement to U is A, the natural complement to T is A, the natural complement to C is G and the natural complement to G is C.

A "nucleic acid" is a deoxyribonucleotide or ribonucleotide polymer in either single- or double-stranded form, and unless otherwise limited, encompasses analogs of natural nucleotides.

A "nucleoside analog" as used herein is defined in more detail below and includes analogs of ribonucleosides and deoxyribonucleosides and the mono- di-, an triphosphates (nucleotides) thereof. As described above, they can be naturally occurring or non-naturally occurring, and derived from natural sources or synthesized. These monomeric units are nucleoside analogs (or "nucleotide" analogs if the monomer is considered with reference to phosphorylation). For instance, structural groups are optionally added to the sugar or base of a nucleoside for incorporation into an oligonucleotide, such as a methyl or allyl group at the 2'-O position on the sugar, or a fluoro group which substitutes for the 2'-O group, or a bromo group on the nucleoside base. The phosphodiester linkage, or "sugar-phosphate backbone" of the oligonucleotide analog is substituted or modified, for instance with methyl phosphonates or O-methyl phosphates.

A "genomic nucleic acid" is a nucleic acid polymer homologous to a nucleic acid which encodes a naturally occurring nucleic acid polymer (RNA or DNA) packaged by a viral particle. Typically, the packaged nucleic acid encodes some or all of the components necessary for viral replication. The genomic nucleic acid optionally includes nucleotide analogs. Nucleic acids are homologous when they are derived from a nucleic acid with a common sequence (an "ancestral" nucleic acid) by natural or artificial modification of the ancestral nucleic acid. Retroviral genomic nucleic acids optionally encode an RNA competent to be packaged by a retroviral particle. Such nucleic acids can be constructed by recombinantly combining a packaging site with a nucleic acid of choice.

A "virally infected cell" is a cell transduced with a viral nucleic acid. The nucleic acid is optionally incorporated into the cellular genome, or is optionally episomal.

The "mutation rate" of a virus or nucleic acid refers to the number of changes occurring upon copying the nucleic acid, e.g., by a polymerase. Typically, this is measured over time, i.e., the number of alterations occurring during rounds of copying or generations of virus.

A "polymerase" refers to an enzyme (DNA or RNA polymerase) that produces a polynucleotide sequence, complementary to a pre-existing template polynucleotide (DNA or RNA). For example, an RNA polymerase may be either an RNA viral polymerase or replicase or RNA cellular polymerase. A "cellular polymerase" is a polymerase derived from a cell. The cell may be prokaryotic or eukaryotic. The cellular RNA polymerase is typically an RNA polymerase such as Pol II or Pol III. Pol II enzymes are most preferred. A "mammalian RNA polymerase II" is an RNA polymerase II derived from a mammal. A "human RNA polymerase II" is an RNA polymerase II derived from a human. A "murine RNA polymerase II" is an RNA polymerase II derived from a mouse. The polymerase is optionally naturally occurring, or artificially (e.g., recombinantly) produced.

A "cell culture" is a population of cells residing outside of an animal. These cells are optionally primary cells isolated from a cell bank, animal, or blood bank, or secondary cells cultured from one of these sources, or long-lived artificially maintained in vitro cultures that are widely available.

A "progressive loss of viability" refers to a measurable reduction in the replicative or infective ability of a population of viruses over time.

A "viral particle" is a viral particle substantially encoded by an RNA virus or a virus with an RNA intermediate, such as BVDV, HCV, or HIV. The presence of non-viral or cellular components in the particle is a common result of the replication process of a virus, which typically includes budding from a cellular membrane.

An "HIV particle" is a retroviral particle substantially encoded by HIV. The presence of non-HIV viral or cellular components in the particle is a common result of the replication process of HIV, typically including budding from a cellular membrane. In certain applications, retroviral particles are deliberately "pseudotyped" by co-expressing viral proteins from more than one virus (often HIV and VSV) to expand the host range of the resulting retroviral particle. The presence or absence of non-HIV components in an HIV particle does not change the essential nature of the particle, i.e., the particle is still produced as a primary product of HIV replication.

Where the methods discussed below require sequence alignment, such methods of alignment of sequences for comparison are well known in the art. Optimal alignment of sequences for comparison may be conducted by the local homology algorithm of Smith and Waterman (1981) *Adv. Appl. Math.* 2: 482; by the homology alignment algorithm of Needleman and Wunsch (1970) *J. Mol. Biol.* 48: 443; by the search for similarity method of Pearson and Lipman (1988) *Proc. Natl. Acad. Sci. USA* 85: 2444; by computerized implementations of these algorithms (including, but not limited to CLUSTAL in the PC/Gene program by Intelligenetics, Mountain View, Calif., GAP, BESTFIT, FASTA, and TFASTA in the Wisconsin Genetics Software Package, Genetics Computer Group (GCG), 575 Science Dr., Madison, Wis., USA); the CLUSTAL program is well described by Higgins and Sharp (1988) *Gene,* 73: 237-244 and Higgins and Sharp (1989) *CABIOS* 5: 151-153; Corpet, et al., (1988) *Nucleic Acids Research* 16, 10881-90; Huang, et al., (1992) *Computer Applications in the Biosciences* 8, 155-65, and Pearson, et al., (1994) *Methods in Molecular Biology* 24, 307-31. Typically, the alignments are visually inspected and refined manually after computer-aided adjustment.

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the default parameters described herein, to determine percent sequence identity for the nucleic acids and proteins of the invention. Software for performing BLAST analyses is publicly available through the National Center for Biotechnology Information (http://www.ncbi.nlm.nih.gov/). The BLASTN program (for nucleotide sequences) uses as defaults a wordlength (W) of 11, an expectation (E) of 10, M=5, N=-4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=-4, and a comparison of both strands.

As used herein, "cancer" includes solid tumors and hematological malignancies. The former includes cancers such as breast, colon, and ovarian cancers. The latter include hematopoietic malignancies including leukemias, lymphomas and myelomas. This invention provides new effective methods, compositions, and kits for treatment and/or prevention of various types of cancer.

Hematological malignancies, such as leukemias and lymphomas, are conditions characterized by abnormal growth and maturation of hematopoietic cells.

Leukemias are generally neoplastic disorders of hematopoietic stem cells, and include adult and pediatric acute myeloid leukemias (AML), chronic myeloid leukemia (CML), acute lymphocytic leukemia (ALL), chronic lymphocytic leukemia (CLL), hairy cell leukemia and secondary leukemia. Myeloid leukemias are characterized by infiltration of the blood, bone marrow, and other tissues by neoplastic cells of the hematopoietic system. CLL is characterized by the accumulation of mature-appearing lymphocytes in the peripheral blood and is associated with infiltration of bone marrow, the spleen and lymph nodes.

Specific leukemias include acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

Lymphomas are generally neoplastic transformations of cells that reside primarily in lymphoid tissue. Among lymphomas, there are two major distinct groups: non-Hodgkin's lymphoma (NHL) and Hodgkin's disease. Lymphomas are tumors of the immune system and generally are present as both T cell- and as B cell-associated disease. Bone marrow, lymph nodes, spleen and circulating cells are all typically involved. Treatment protocols include removal of bone marrow from the patient and purging it of tumor cells, often using antibodies directed against antigens present on the tumor cell type, followed by storage. The patient is then given a toxic dose of radiation or chemotherapy and the purged bone marrow is then reinfused in order to repopulate the patient's hematopoietic system.

Other hematological malignancies include myelodysplastic syndromes (MDS), myeloproliferative syndromes (MPS) and myelomas, such as solitary myeloma and multiple myeloma. Multiple myeloma (also called plasma cell myeloma) involves the skeletal system and is characterized by multiple tumorous masses of neoplastic plasma cells scattered throughout that system. It may also spread to lymph nodes and other sites such as the skin. Solitary myeloma involves solitary lesions that tend to occur in the same locations as multiple myeloma.

Hematological malignancies are generally serious disorders, resulting in a variety of symptoms, including bone marrow failure and organ failure. Treatment for many hematological malignancies, including leukemias and lymphomas, remains difficult, and existing therapies are not universally effective. While treatments involving specific immunotherapy appear to have considerable potential, such treatments are limited by the small number of known malignancy-associated antigens. Moreover the ability to detect such hematological malignancies in their early stages can be quite difficult depending upon the particular malady. Accordingly, there remains a need in the art for improved methods for treatment of hematological malignancies such as B cell leukemias and lymphomas and multiple myelomas. The present invention fulfills these and other needs in the field.

Other cancers are also of concern, and represent similar difficulties insofar as effective treatment is concerned. Such cancers include those characterized by solid tumors. Examples of other cancers of concern are skin cancers, including melanomas, basal cell carcinomas, and squamous cell carcinomas. Epithelial carcinomas of the head and neck are also encompassed by the present invention. These cancers typically arise from mucosal surfaces of the head and neck and include salivary gland tumors.

The present invention also encompasses cancers of the lung. Lung cancers include squamous or epidermoid carcinoma, small cell carcinoma, adenocarcinoma, and large cell carcinoma. Breast cancer is also included, both invasive breast cancer and non-invasive breast cancer, e.g., ductal carcinoma in situ and lobular neoplasia.

The present invention also encompasses gastrointestinal tract cancers. Gastrointestinal tract cancers include esophageal cancers, gastric adenocarcinoma, primary gastric lymphoma, colorectal cancer, small bowel tumors and cancers of the anus. Pancreatic cancer and cancers that affect the liver are also of concern, including hepatocellular cancer. The present invention also includes treatment of bladder cancer and renal cell carcinoma.

The present invention also encompasses prostatic carcinoma and testicular cancer.

Gynecologic malignancies are also encompassed by the present invention including ovarian cancer, carcinoma of the fallopian tube, uterine cancer, and cervical cancer.

Treatment of sarcomas of the bone and soft tissue are encompassed by the present invention. Bone sarcomas include osteosarcoma, chondrosarcoma, and Ewing's sarcoma.

The present invention also encompasses malignant tumors of the thyroid, including papillary, follicular, and anaplastic carcinomas.

In some embodiments, a "subject in need of treatment" is a mammal with a viral disease that is life-threatening, or that impairs health, or shortens the lifespan of the mammal. In other embodiments, a "subject in need of treatment" is a mammal with cancer that is life-threatening or that impairs health or shortens the lifespan of the mammal.

A "pharmaceutically acceptable" component is one that is suitable for use with humans and/or animals without undue adverse side effects (such as toxicity, irritation, and allergic response) commensurate with a reasonable benefit/risk ratio.

A "safe and effective amount" refers to the quantity of a component that is sufficient to yield a desired therapeutic response without undue adverse side effects (such as toxicity, irritation, or allergic response) commensurate with a reasonable benefit/risk ratio when used in the manner of this invention. In some embodiments "therapeutically effective amount" refers to an amount of a component effective to yield the desired therapeutic response, for example, an amount effective to enhance mutagenesis of a virus, or to diminish the ability of the virus to produce active proteins, or to inhibit replication of a virus, or to eliminate or diminish the ability of a virus to produce infectious particles, or to kill the virus or a virally infected cell. Other embodiments encompass other therapeutic responses, for example, an amount of a component effective to halt or to delay the growth of a cancer, or to cause a cancer to shrink, or not metastasize. The specific safe and effective amount or therapeutically effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

An "enteric formulation" is a formulation of a compound wherein the compound is stable in the acidic environment of the stomach, and after passage through the stomach, an active form of the compound is available for absorbtion in the intestinal tract. An "oral osmotic drug device" as used herein is a device that delivers a drug at a controlled rate in a region of the gastrointestinal tract having a pH less than 3.5, and then delivers all the drug in the immediately continuing region of the gastrointestinal tract having a pH greater than 3.5. Methods to make and use an oral osmotic drug device are found, for example, in U.S. Pat. No. 4,587,117, herein incorporated by reference.

The Compounds

The present invention provides compounds that display antiviral activity, in addition to salts and prodrugs of such compounds. The compounds are generally nucleosides, nucleotides, nucleoside analogues, nucleotide analogues, salts and prodrugs thereof. The inventors have recognized that antiviral pharamacophores comprising highly active, yet biologically unstable nucleosides or nucleotides and nucleoside or nucleotide analogues are converted to useful therapeutic agents by altering selected properties of the pharmacophore. In an exemplary embodiment, the pharmacophore is stabilized by the attachment of the active species containing the pharmacophore to a modifying group that increases the lipophilicity of the pharmacophore. The combination of the pharmacophore and the modifying group preferably provides the pharmacophore in a prodrug format.

Prodrugs comprise inactive forms of active drugs in which a chemical group is present on the prodrug, which renders it inactive and/or confers solubility or some other property to the drug. Prodrugs are generally inactive, or less active than the parent compound, but once the chemical group has been cleaved from the prodrug (e.g., by hydrolysis, heat, cavitation, pressure, and/or enzymes in the surrounding environment), the active drug is generated. Prodrugs may be designed as reversible drug derivatives and utilized as modifiers to enhance drug transport to site-specific tissues. Prodrugs are described in the art, for example, in Sinkula et al., *J. Pharm. Sci* 64: 181-210 (1975) and in U.S. Provisional Patent Application No. 60/480,037, filed Jun. 20, 2003, which is herein incorporated by reference for all purposes.

Thus, the present invention provides, inter alia, novel nucleoside and nucleotide analogues that are covalently attached to a group that modifies the properties of the nucleoside or nucleotide analogue. In exemplary embodiments, the "modifying group" enhances the stability or bioavailability of nucleoside or nucleotide or its analogue. In the discussion that follows, the invention is exemplified by reference to lipophilic modifying groups. The focus of the discussion is for clarity of illustration, and those of skill in the art will appreciate that compounds including modifying groups other the lipophilic groups discussed herein are within the scope of the invention.

Thus, in a first aspect, there is provided a compound according to Formula I:

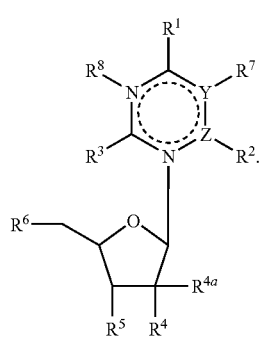
(I)

In Formula I, the dashed circle indicates that the ring system may include one or more double bonds at any position, such that the valence of the intra-annular atoms is satisfied. The ring system may be aromatic (e.g., heteroaryl) or non-aromatic. The substituents $R^2$, $R^7$, $R^9$ are present or absent as dictated by the application of the laws of valency to a selected ring structure.

The symbol Y represents C, CH or N, and the symbol Z represents C, CH or B. $R^1$ is a member selected from H, acyl, $OR^9$, $SR^9$, $NR^9NHR^{10}$, $NR^9R^{10}$, =O and =$NR^9$, in which $R^9$ and $R^{10}$ are members independently selected from H, substituted or unsubstituted alkyl, acyl, substituted or unsubstituted heteroalkyl and substituted or unsubstituted aryl.

The symbol $R^2$ represents a substituent that is a member selected from H, acyl, substituted or unsubstituted alkyl, $OR^{11}$, $SR^{11}$, $NR^{11a}$, $NR^{12a}$, halogen, and =O. The symbol $R^{11}$ represents a member selected from H, substituted or unsubstituted alkyl, substituted or unsubstituted heterocycloalkyl, or substituted or unsubstituted heteroaryl. $R^{11a}$ and $R^{12a}$ are members independently selected from H, substituted or unsubstituted alkyl, substituted or unsubstituted heteroalkyl, substituted or unsubstituted aryl and substituted or unsubstituted heteroaryl.

$R^3$ is a member selected from H, acyl, substituted or unsubstituted alkyl, $NR^{12}R^{13}$, $NR^{12}OR^{13}$, $SR^{12}$, (=O) and $OR^{12}$. The symbols $R^{12}$ and $R^{13}$ represent members independently selected from H, substituted or unsubstituted alkyl, acyl, substituted or unsubstituted heteroalkyl, substituted or unsubstituted aryl or substituted or unsubstituted heteroaryl.

$R^4$ and $R^{4a}$ are members independently selected from H, halogen, OMe and OH. In a preferred embodiment, the halogen is F.

$R^5$ and $R^6$ are members independently selected from H, and $OR^{14}$. The symbol $R^{14}$ represents H, substituted or unsubstituted alkyl, acyl, substituted or unsubstituted heteroalkyl, or substituted or unsubstituted aryl and $P(O)(R^{15})(R^{16})$. $R^{15}$ and $R^{16}$ are independently selected from $OR^{17}$, $NR^{17}R^{18}$, substituted or unsubstituted alkyl and substituted or unsubstituted nucleosides. $R^{17}$ and $R^{18}$ are independently selected from H, $CH_2CH CN$, substituted or unsubstituted alkyl, substituted or unsubstituted heteroalkyl, substituted or unsubstituted aryl and substituted or unsubstituted heteroaryl.

A member selected from $R^5$ and $R^3$; $R^6$ and $R^3$; and $R^{15}$ and $R^{16}$ together with the atoms to which they are attached, are optionally joined to form a ring system selected from substituted or unsubstituted cycloalkyl and substituted or unsubstituted heterocycloalkyl. In an exemplary embodiment, the ring system is a 5 or 6 membered ring system.

$R^7$ and $R^8$ are independently selected from H, acyl, substituted or unsubstituted alkyl. $R^1$ and $R^8$, together with the atoms to which they are attached are optionally joined into a ring system selected from substituted or unsubstituted cycloalkyl and substituted or unsubstituted heterocycloalkyl.

In an exemplary embodiment, the invention provides a compound according to Formula II:

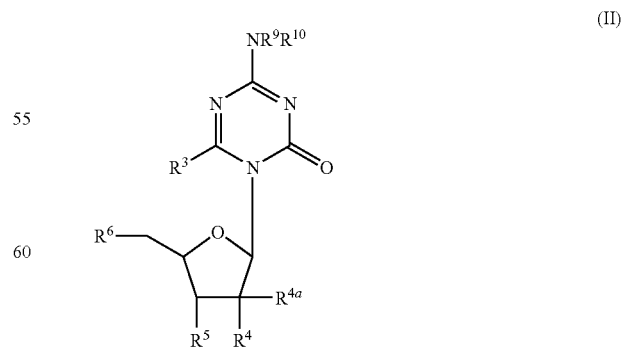
(II)

in which the identity of each of the radicals is substantially as described above.

In another exemplary embodiment, there is provided a compound according to Formula III:

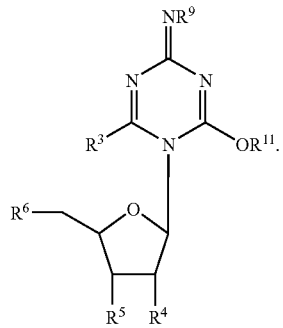
(III)

In an exemplary compound according to Formula III, $R^{11}$ is cleaveable moiety, for example, a silyl group or substituted or unsubstituted alkyl ether, e.g.,

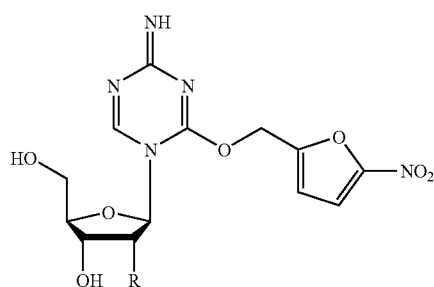

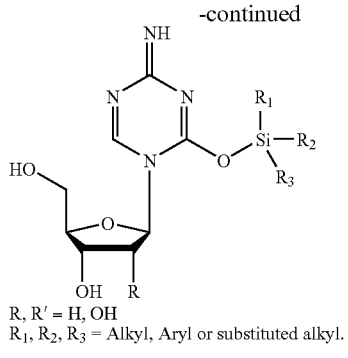

R, R' = H, OH
$R_1$, $R_2$, $R_3$ = Alkyl, Aryl or substituted alkyl.

In a still further exemplary embodiment, the invention provides a compound of Formula IV:

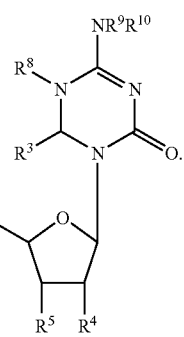
(IV)

Exemplary compounds according to the Formulae above include:

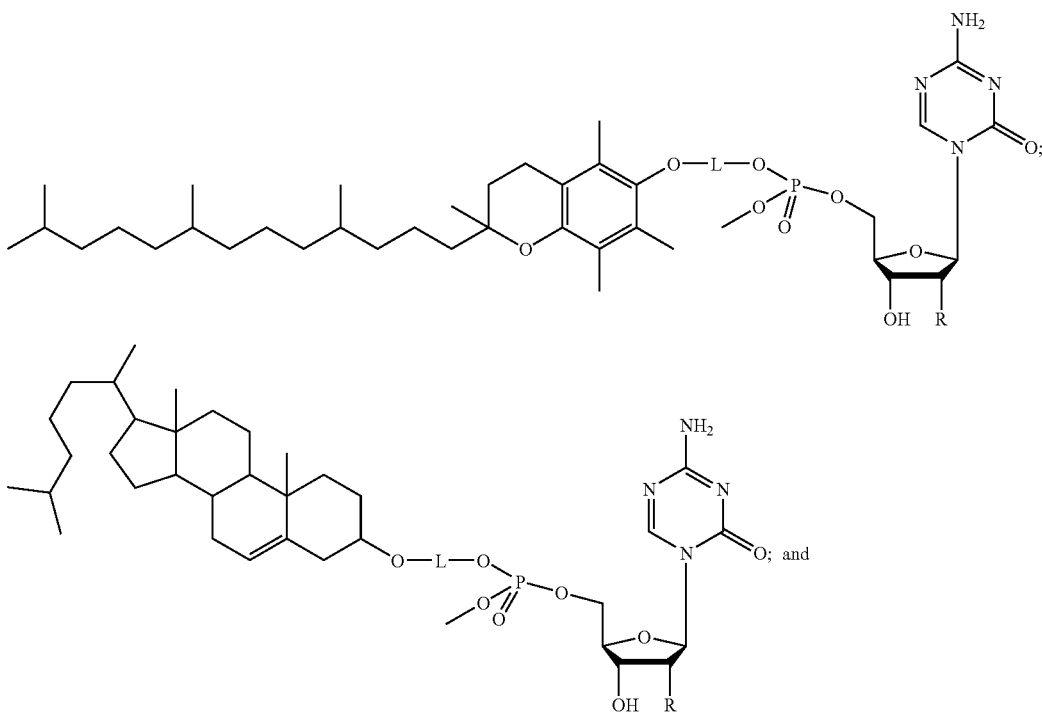

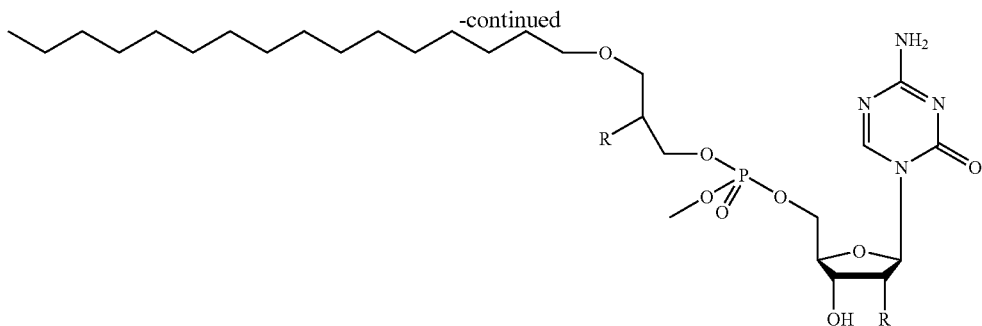

R = H, OH, OMe

Still further exemplary compounds based upon a polynucleotide-like format include:

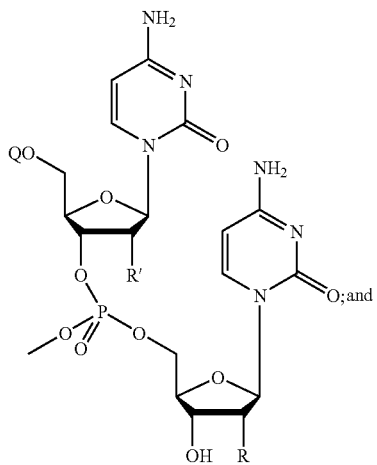

R, R' = H, OH
Q = Hydrophobic substituent

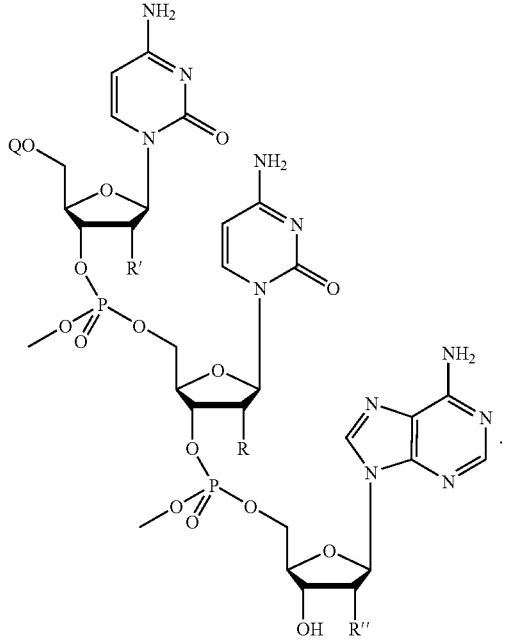

R, R', R'' = H, OH
Q = Hydrophobic substituent

In a further embodiment, the present invention provides a compound according to Formula V:

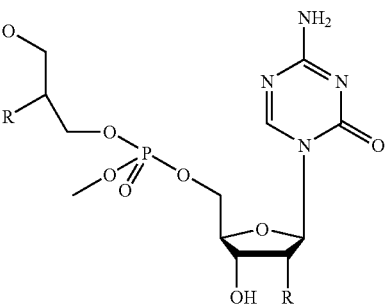

(V)

in which $R^{19}$, $R^{20}$, and $R^{21}$ are members independently selected from H, acyl and substituted or unsubstituted alkyl.

Compounds according to Formula V, provide the active compound by elimination of the nitrogen "protecting group":

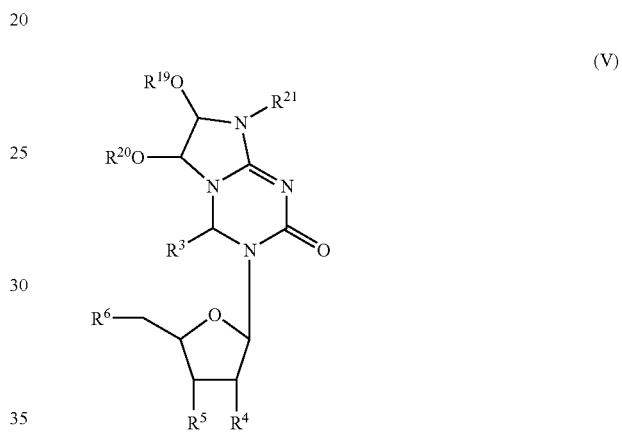

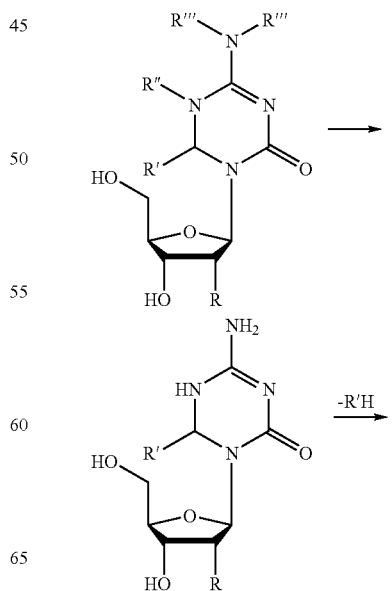

-continued

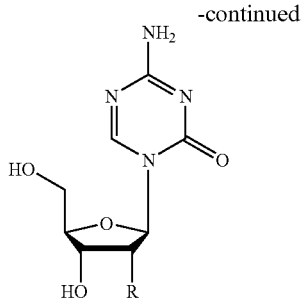

R=H, OH; R' is a leaving group OAlkyl, OAryl, OHeteroaryl, SAlkyl, SAryl, S(O)Heteroaryl, S(O)$_2$Heteroaryl, S(O)$_2$Alkyl, S(O)Aryl, S(O)$_2$Heteroaryl, Cl, Br, I, N(Alkyl)$_2$; R", R"', and R"" are nitrogen protecting groups In an exemplary embodiment, R$^6$ has a structure according to Formula VI or Formula VII:

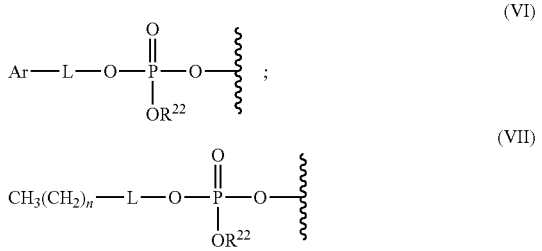

in which R$^{22}$ represents substituted or unsubstituted alkyl or a substituted or unsubstituted heteroalkyl moiety. The symbol L represents a linker selected from substituted or unsubstituted alkyl and substituted or unsubstituted heteroalkyl; and Ar is a member selected from substituted or unsubstituted aryl and substituted or unsubstituted heteroaryl. The symbol n represents an integer from 1 to 30.

An exemplary linker precursor contains at least two linking groups derived from reactive functional groups. Typically, one linking group of the linker bonds to an oxygen of the phosphate (phosphodiester), while the other linking group of the linker bonds to a chemical functionality of the pharmaceutical agent. Examples of chemical functionalities of linker groups include hydroxy, mercapto, carbonyl, carboxy, amino, ketone, and mercapto groups.

Exemplary linker groups include 6-aminohexanol, 6-mercaptohexanol, 10-hydroxydecanoic acid, glycine and other amino acids, 1,6-hexanediol, β-alanine, 2-aminoethanol, cysteamine (2-aminoethanethiol), 5-aminopentanoic acid, 6-aminohexanoic acid, 3-maleimidobenzoic acid, phthalide, α-substituted phthalides, the carbonyl group, aminal esters, and the like. Other "bifunctional" linker groups include, but are not limited to, moieties such as sugars (e.g., polyol with reactive hydroxyl), amino acids, amino alcohols, carboxy alcohols, amino thiols, and the like.

Generally, at least one of the chemical functionalities of the linker group, the modifying group or the pharmacophore will be activated to allow for the formation of the pharmacophore-linker-modifying group complex. One skilled in the art will appreciate that a variety of chemical functionalities, including hydroxy, amino, and carboxy groups, can be activated using a variety of standard methods and conditions. For example, a hydroxyl group of the linker or pharmacophore can be activated through treatment with phosgene to form the corresponding chloroformate, or p-nitrophenylchloroformate to form the corresponding carbonate.

In an exemplary embodiment, the compound of the invention includes a linker that includes a carboxyl functionality. Carboxyl groups may be activated by, for example, conversion to the corresponding acyl halide, imidazolide or active ester. This reaction may be performed under a variety of conditions as illustrated in March, supra pp. 388-89. In a preferred embodiment, the acyl halide is prepared through the reaction of the carboxyl-containing group with oxalyl chloride. Those of skill in the art will appreciate that the use of carboxyl-containing agents is merely illustrative, and that agents having many other functional groups can be incorporated within the compounds of the invention.

Typically, the compounds of the invention are prepared using standard chemical techniques to join the various components through their respective chemical functionalities. Those of skill in the art will recognize that one can first attach the linker either to the pharmacophore or to the modifying group. The exemplary chemical functionalities shown in Table 1 can be present on the pharmacophore, linker, or modifying group, depending on the synthesis scheme employed. Table 1 provides examples of a first chemical functionality that is a component of either the pharmacaphore or a substituent and a second chemical functionality that is a component of either the pharmacaphore or a substituent. The exemplary linkages set forth in Table 1 are produced by the covalent interaction of chemical functionality 1 and 2.

The groups set forth in Table 1 are also generally representative of "active groups," which are found on core moieties of use in the present invention.

TABLE 1

| Chemical Functionality 1 | Chemical Functionality 2 | Linkage |
| --- | --- | --- |
| Hydroxy | Carboxy | Ester |
|  | Hydroxy | Carbonate |
|  | Amine | Carbamate |
|  | SO$_3$ | Sulfate |
|  | PO$_3$ | Phosphate |
|  | Carboxy | Acyloxyalkyl |
|  | Ketone | Ketal |
|  | Aldehyde | Acetal |
|  | Hydroxy | Anhydride |
| Mercapto | Mercapto | Disulfide |
|  | Carboxy | Acyloxyalkyl Thioether |
|  | Carboxy | Thioester |
|  | Carboxy | Amino amide |
|  | Mercapto | Thioester |
|  | Carboxy | Acyloxyalkyl ester |
|  | Carboxy | Acyloxyalkyl amide |
|  | Amino | Acyloxyalkoxy carbonyl |
|  | Carboxy | Anhydride |
|  | Carboxy | N-acylamide |
|  | Hydroxy | Ester |
|  | Hydroxy | Hydroxymethyl ketone ester |
|  | Hydroxy | Alkoxycarbonyl oxyalkyl |
| Amino | Carboxy | Acyloxyalkylamine |
|  | Carboxy | Acyloxyalkylamide |
|  | Amino | Urea |
|  | Carboxy | Amide |
|  | Carboxy | Acyloxyalkoxycarbonyl |
|  | Amide | N-Mannich base |
|  | Carboxy | Acyloxyalkyl carbamate |
| Phosphate oxygen ester | Hydroxy | Phosphate |
|  | Amine | Phosphoramidate |
|  | Mercapto | Thiophosphate ester |

TABLE 1-continued

| Chemical Functionality 1 | Chemical Functionality 2 | Linkage |
|---|---|---|
| Ketone | Carboxy | Enol ester |
| Sulfonamide | Carboxy | Acyloxyalkyl sulfonamide |
|  | Ester | N-sulfonyl- imidate |

One skilled in the art will readily appreciate that many of these linkages may be produced in a variety of ways and using a variety of conditions. For the preparation of esters, see, e.g., March supra at 1157; for thioesters, see, March, supra at 362-363, 491, 720-722, 829, 941, and 1172; for carbonates, see, March, supra at 346-347; for carbamates, see, March, supra at 1156-57; for amides, see, March supra at 1152; for ureas and thioureas, see, March supra at 1174; for acetals and ketals, see, Greene et al. supra 178-210 and March supra at 1146; for acyloxyalkyl derivatives, see, PRODRUGS: TOPICAL AND OCULAR DRUG DELIVERY, K. B. Sloan, ed., Marcel Dekker, Inc., New York, 1992; for enol esters, see, March supra at 1160; for N-sulfonylimidates, see, Bundgaard et al., J. Med. Chem., 31:2066 (1988); for anhydrides, see, March supra at 355-56, 636-37, 990-91, and 1154; for N-acylamides, see, March supra at 379; for N-Mannich bases, see, March supra at 800-02, and 828; for hydroxymethyl ketone esters, see, Petracek et al. Annals NY Acad. Sci., 507:353-54 (1987); for disulfides, see, March supra at 1160; and for phosphonate esters and phosphonamidates, see, e.g., copending application Ser. No. 07/943,805, which is expressly incorporated herein by reference.

In certain embodiments, one or more of the active groups are protected during one or more steps of the reaction to assemble the compound of the invention. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

The linker can also serve to introduce additional molecular mass and chemical functionality into the compound of the invention. Generally, the additional mass and functionality will affect the serum half-life and other properties of the compound. Thus, through careful selection of linker groups, compounds of the invention with a range of serum half-lives can be produced.

In another exemplary embodiment, the linker includes a bond that renders the compound of the invention susceptible to in vivo degradation. In a preferred embodiment, the bond is reversible (e.g., easily hydrolyzed) or partially reversible (e.g., partially or slowly hydrolyzed). Cleavage of the bond can occur through biological or physiological processes. In other embodiments, the physiological processes will cleave bonds at other locations within the complex (e.g., removing an ester group or other protecting group that is coupled to an otherwise sensitive chemical functionality) before cleaving the bond between the agent and dendrimer, resulting in partially degraded complexes. Other cleavages can also occur, for example, between the spacer and agent and the spacer and dendrimer.

For rapid degradation of the complex after administration, circulating enzymes in the plasma can be used to cleave the dendrimer from the pharmaceutical agent. These enzymes can include non-specific aminopeptidases and esterases, dipeptidyl carboxy peptidases, proteases of the blood clotting cascade, and the like.

Alternatively, cleavage may occur through nonenzymatic processes. For example, chemical hydrolysis may be initiated by differences in pH experienced by the complex following delivery. In such a case, the pharmaceutical agent-dendrimer complex may be characterized by a high degree of chemical lability at physiological pH of 7.4, while exhibiting higher stability at an acidic or basic pH in the reservoir of the delivery device. An exemplary pharmaceutical agent-dendrimer complex, which is cleaved in such a process is a complex incorporating a N-Mannich base linkage within its framework.

In most cases, cleavage of the compound will occur during or shortly after administration. However, in certain embodiments, cleavage does not occur until the complex reaches the pharmaceutical agent's site of action.

The susceptibility of the compound of the invention to degradation can be ascertained through studies of the hydrolytic or enzymatic conversion of the complex to the unbound pharmaceutical agent. Generally, good correlation between in vitro and in vivo activity is found using this method. See, e.g., Phipps et al., J. Pharm. Sciences 78:365 (1989). The rates of conversion may be readily determined, for example by spectrophotometric methods or by gas-liquid or high-pressure liquid chromatography. Half-lives and other kinetic parameters may then be calculated using standard techniques. See, e.g., Lowry et al. MECHANISM AND THEORY IN ORGANIC CHEMISTRY, 2nd Ed., Harper & Row, Publishers, New York (1981).

In a preferred embodiment, one or more of the substituents (modifying groups) on the nucleoside or nucleotide (or analogue) core is a lipid, or is lipophilic; an embodiment of the invention that is illustrated by reference to compounds of the invention in which the substituent is a hydrophobic species, such as a lipid.

A wide variety of lipids may be used in preparing the compositions of the invention. The lipids may be of either natural, synthetic or semi-synthetic origin, including for example, fatty acids, fatty alcohols, neutral fats, phosphatides, oils, glycolipids, surface-active agents (surfactants), aliphatic alcohols, waxes, terpenes and steroids.

Exemplary lipids which may be used to prepare the compounds of the present invention include, for example, fatty acids, lysolipids, fluorolipids, phosphocholines, such as those associated with platelet activation factors (PAF) (Avanti Polar Lipids, Alabaster, Ala.), including 1-alkyl-2-acetoyl-sn-glycero 3-phosphocholines, and 1-alkyl-2-hydroxy-sn-glycero 3-phosphocholines, phosphatidylcholine with both saturated and unsaturated lipids, including dioleoylphosphatidylcholine; dimyristoylphosphatidylcholine; dipentadecanoylphosphatidylcholine; dilauroylphosphatidylcholine; dipalmitoylphosphatidylcholine (DPPC); distearoylphosphatidylcholine (DSPC); and diarachidonylphosphatidylcholine (DAPC); phosphatidylethanolamines, such as dioleoylphosphatidylethanolamine, dipalmitoylphosphatidylethanolamine (DPPE) and distearoylphosphatidylethanolamine (DSPE); phosphatidylserine; phosphatidylglycerols, including distearoylphosphatidyl-glycerol (DSPG); phosphatidylinositol; sphingolipids such as sphingomyelin; glycolipids such as ganglioside GM1 and GM2; glucolipids; sulfatides; glycosphingolipids; phosphatidic acids, such as dipalmitoylphosphatidic acid (DPPA) and distearoyl-phosphatidic acid (DSPA); palmitic acid; stearic acid; arachidonic acid; oleic acid; lipids bearing polymers, such as chitin, hyaluronic acid, polyvinyl-pyrrolidone or polyethylene glycol (PEG), also referred to herein as "pegylated lipids" with preferred lipid bearing polymers including DPPE-PEG (DPPE-PEG), which refers to the lipid DPPE having a PEG polymer attached thereto, including, for example, DPPE-PEG5000, which refers to DPPE having attached thereto a PEG polymer having a mean average molecular weight of about 5000; lipids bearing sulfonated mono-, di-, oligo- or polysaccharides; cholesterol, cholesterol sulfate and cholesterol hemisuccinate; tocopherol hemisuccinate; lipids with ether and ester-linked fatty acids; polymerized lipids (a wide variety of which are well known in the art); dicetyl phosphate; stearylamine; cardiolipin; phospholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes such as polyoxyalkylene (e.g., polyoxyethylene) fatty acid esters, polyoxyalkylene (e.g., polyoxyethylene) fatty alcohols, polyoxyalkylene (e.g., polyoxyethylene) fatty alcohol ethers, polyoxyalkylene sorbitan fatty acid esters (such as, for example, the class of compounds referred to as TWEEN™, including TWEEN 20, TWEEN 40 and TWEEN 80, commercially available from ICI Americas, Inc., Wilmington, Del.), including polyoxyethylated sorbitan fatty acid esters, glycerol polyethylene glycol oxystearate, glycerol polyethylene glycol ricinoleate, ethoxylated soybean sterols, ethoxylated castor oil, polyoxyethylene-polyoxypropylene polymers, and polyoxyethylene fatty acid stearates; sterol aliphatic acid esters including cholesterol sulfate, cholesterol butyrate, cholesterol isobutyrate, cholesterol palmitate, cholesterol stearate, lanosterol acetate, ergosterol palmitate, and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid and polyuronic acid; saponins including sarsasapogenin, smilagenin, hederagenin, oleanolic acid, and digitoxigenin; glycerol dilaurate, glycerol trilaurate, glycerol dipalmitate, glycerol and glycerol esters including glycerol tripalmitate, glycerol distearate, glycerol tristearate, glycerol dimyristate, glycerol trimyristate; long chain alcohols including n-decyl alcohol, lauryl alcohol, myristyl alcohol, cetyl alcohol, and n-octadecyl alcohol; 6-(5-cholesten-3β-yloxy)-1-thio-β-D-galactopyranoside; digalactosyldiglyceride; 6-(5-cholesten-3β-yloxy)-hexyl-6-amino-6-deoxy-1-thio-β-D-galactopyranoside; 6-(5-cholesten-3β-yloxy)hexyl-6-amino-6-deoxyl-1-thio-α-D-manno pyranoside; 12-(((7'-diethylamino-coumarin-3-yl)-carbonyl)-methylamino)-octadecanoic acid; N-[12-(((7'-diethylamino-coumarin-3-yl)-carbonyl)-methylamino)-octadecanoyl]-2-aminopalmitic acid; cholesteryl(4'-trimethyl-ammonio)-butanoate; N-succinyldioleoylphosphatidylethanol-amine; 1,2-dioleoyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine and palmitoylhomocysteine, and/or any combinations thereof.

Examples of polymerized lipids include unsaturated lipophilic chains such as alkenyl or alkynyl, containing up to about 50 carbon atoms. Further examples are phospholipids such as phosphoglycerides and sphingolipids carrying polymerizable groups, and saturated and unsaturated fatty acid derivatives with hydroxyl groups, such as for example triglycerides of d-12-hydroxyoleic acid, including castor oil and ergot oil. Polymerization may be designed to include hydrophilic substituents such as carboxyl or hydroxyl groups, to enhance dispersability so that the backbone residue resulting from biodegradation is water-soluble. Suitable polymerizable lipids are also described, for example, in Klaveness et al, U.S. Pat. No. 5,536,490.

If desired, the compound of the invention may comprise a cationic lipid, such as, for example, N-[1-(2,3-dioleoyloxy) propyl]-N,N,N-trimethylammonium chloride (DOTMA), 1,2-dioleoyloxy-3-(trimethylammonio)propane (DOTAP); and 1,2-dioleoyl-3-(4'-trimethylammonio)-butanoyl-sn-glycerol (DOTB).

Exemplary anionic lipids include phosphatidic acid and phosphatidyl glycerol and fatty acid esters thereof, amides of phosphatidyl ethanolamine such as anandamides and methanandamides, phosphatidyl serine, phosphatidyl inositol and fatty acid esters thereof, cardiolipin, phosphatidyl ethylene glycol, acidic lysolipids, sulfolipids, and sulfatides, free fatty acids, both saturated and unsaturated, and negatively charged derivatives thereof. Phosphatidic acid and phosphatidyl glycerol and fatty acid esters thereof are preferred anionic lipids.

Examples of cationic lipids include those listed hereinabove. A preferred cationic lipid for formation of aggregates is N-[1-(2,3-dioleoyloxy)propyl]-N,N,N-trimethylammonium chloride ("DOTMA"). Synthetic cationic lipids may also be used. These include common natural lipids derivatized to contain one or more basic functional groups. Examples of lipids which can be so modified include dimethyldioctadecyl-ammonium bromide, sphinolipids, sphingomyelin, lysolipids, glycolipids such as ganglioside GM1, sulfatides, glycosphingolipids, cholesterol and cholesterol esters and salts, N-succinyldioleoylphosphatidylethanolamine, 1,2-dioleoyl-sn-glycerol, 1,3-dipalmitoyl-2-succinylglycerol, 1,2-dipalmitoyl-sn-3-succinylglycerol, 1-hexadecyl-2-palmitoylglycerophosphatidylethanolamine and palmitoylhomocystiene.

Specially synthesized cationic lipids also function in the embodiments of the invention. Among these are, for example, N,N'-bis(dodecyaminocarbonyl-methylene)-N,N'-bis(β-N, N,N-trimethyl ammoniumethylaminocarbonylmethylene-ethylene-diamine tetraiodide; N,N''-bis hexadecylaminocarbonylmethylene)-N,N',N''-tris hexaiodide; N,N'-Bis (dodecylaminocarbonylmethylene)-N,N''-bis(β-N,N,N-trimethylammoniumethylaminocarbonylmethylene) cyclohexylene-1,4-diamine tetraiodide; 1,1,7,7-tetra-(β-N, N,N,N-tetramethylammoniumethylaminocarbonylmethylene)-3-hexadecylaminocarbonylmethylene-1,3,7-triaazaheptane heptaiodide; and N,N,N'N'-tetraphospho-ethanolaminocarbonylmethylene)diethylenetriamine tetraiodide.

In those embodiments in which both cationic and non-cationic lipids are utilized, a wide variety of lipids, as described above, may be employed as the non-cationic lipid. Preferably, the non-cationic lipid comprises one or more of DPPC, DPPE and dioleoylphosphatidylethanolamine. In lieu of the cationic lipids listed above, lipids bearing cationic polymers, such as polylysine or polyarginine, as well as alkyl phosphonates, alkyl phosphinates, and alkyl phosphites, may also be used in the stabilizing materials. Those of skill in the art will recognize, in view of the present disclosure, that other natural and synthetic variants carrying positive charged moieties will also function in the invention.

Saturated and unsaturated fatty acids, which may be employed in the present compounds, include moieites that preferably contain from about 12 carbon atoms to about 22 carbon atoms, in linear or branched form. Hydrocarbon groups consisting of isoprenoid units and/or prenyl groups can be also used. Examples of suitable saturated fatty acids include, for example, lauric, myristic, palmitic, and stearic acids. Examples of suitable unsaturated fatty acids include, for example, lauroleic, physeteric, myristoleic, palmitoleic, petroselinic, and oleic acids. Examples of suitable branched fatty acids include, for example, isolauric, isomyristic, isopalmitic, and isostearic acids.

Other useful lipids or combinations thereof apparent to those skilled in the art, which are in keeping with the spirit of the present invention are also encompassed by the present invention. For example, carbohydrate-bearing lipids may be employed, as described in U.S. Pat. No. 4,310,505, the disclosure of which is hereby incorporated herein by reference in its entirety.

In addition to the lipids set forth above, the compounds of the present invention may include a moiety that is derived in whole or in part, from proteins or derivatives thereof. Suitable proteins for use in the present invention include, for example, albumin, hemoglobin, α-1-antitrypsin, α-fetoprotein, aminotransferases, amylase, C-reactive protein, carcinoembryonic antigen, ceruloplasmin, complement, creatine phosphokinase, ferritin, fibrinogen, fibrin, transpeptidase, gastrin, serum globulins, myoglobin, immunoglobulins, lactate dehydrogenase, lipase, lipoproteins, acid phosphatase, alkaline phosphatase, α-1-serum protein fraction, α-2-serum protein fraction, β-protein fraction, γ-protein fraction and γ-glutamyl transferase. Other stabilizing materials and vesicles formulated from proteins that may be used in the present invention are described, for example, in U.S. Pat. Nos. 4,572,203, 4,718,433, 4,774,958, and 4,957,656. Other protein-based moieties, in addition to those described above and in the aforementioned patents, are apparent to one of ordinary skill in the art, in view of the present disclosure.

In addition to the lipids and proteins discussed herein, embodiments of the present invention may also include polymers, which may be of natural, semi-synthetic (modified natural) or synthetic origin. Polymer denotes a compound comprised of two or more repeating monomeric units, and preferably 10 or more repeating monomeric units. Semi-synthetic polymer (or modified natural polymer) denotes a natural polymer that has been chemically modified in some fashion. Examples of suitable natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dennatan, hyaluronic acid, alginic acid, xanthin gum, starch and various other natural homopolymer or heteropolymers, such as those containing one or more of the following aldoses, ketoses, acids or amines: erythrose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin. Exemplary semi-synthetic polymers include carboxymethylcellulose, hydroxymethyl-cellulose, hydroxypropylmethyl-cellulose, methylcellulose, and methoxycellulose. Exemplary synthetic polymers suitable for use in the present invention include polyphosphazenes, polyethylenes (such as, for example, polyethylene glycol (including, for example, the class of compounds referred to as PLURONICS™, commercially available from BASF, Parsippany, N.J.), polyoxyethylene, and polyethylene terephthalate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof. Preferred are biocompatible synthetic polymers or copolymers prepared from monomers, such as acrylic acid, methacrylic acid, ethyleneimine, crotonic acid, acrylamide, ethyl acrylate, methyl methacrylate, 2-hydroxyethyl methacrylate (HEMA), lactic acid, glycolic acid, ε-caprolactone, acrolein, cyanoacrylate, bisphenol A, epichlorhydrin, hydroxyalkyl-acrylates, siloxane, dimethylsiloxane, ethylene oxide, ethylene glycol, hydroxyalkyl-methacrylates, N-substituted acrylamides, N-substituted methacrylamides, N-vinyl-2-pyrrolidone, 2,4-pentadiene-1-ol, vinyl acetate, acrylonitrile, styrene, p-amino-styrene, p-amino-benzyl-styrene, sodium styrene sulfonate, sodium 2-sulfoxyethyl-methacrylate, vinyl pyridine, aminoethyl methacrylates, 2-methacryloyloxytrimethylammonium chloride, and polyvinylidene, as well as polyfunctional crosslinking monomers such as N,N'-methylenebisacrylamide, ethylene glycol dimethacrylates, 2,2'-(p-phenylenedioxy)-diethyl dimethacrylate, divinylbenzene, triallylamine and methylenebis-(4-phenylisocyanate), including combinations thereof. Preferable polymers include polyacrylic acid, polyethyleneimine, polymethacrylic acid, polymethylmethacrylate, polysiloxane, polydimethylsiloxane, polylactic acid, poly(e-caprolactone), epoxy resin, poly (ethylene oxide), poly(ethylene glycol), and polyamide (nylon) polymers. Preferred copolymers include, but are not limited to, polyvinylidene-polyacrylonitrile, polyvinylidene-polyacrylonitrile-polymethylmethacrylate, polystyrene-polyacrylonitrile and poly d-1, lactide co-glycolide polymers. A preferred copolymer is polyvinylidene-polyacrylonitrile. Other suitable biocompatible monomers and polymers will be apparent to those skilled in the art, in view of the present disclosure.

In a still further exemplary embodiment, the invention provides tricyclic compounds according to Formula VII, in which the radicals are substantially as described above.

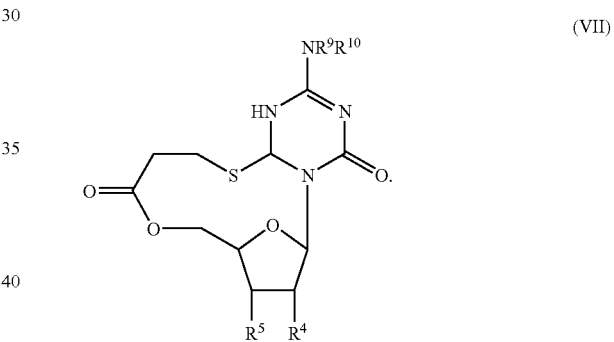

(VII)

Formulations

Many drugs are inherently hydrophobic and hence have limited solubility or ability to be dispersed in an aqueous medium, which reduces their bioavailability and makes them difficult to formulate or administer reducing their usefulness. Contrary, other drugs are excessively hydrophilic and poorly absorbed when given orally. Therefore, certain compounds provided by the present invention are purposely made hydrophobic. Similarly, a number of potentially useful bio-active molecules are not sufficiently stable, or have a too short half-life in biological media for successful treatment, which also limits their use. As a result of these and other problems of pharmacokinetics, bioavailability, specificity, etc., there is a need to develop molecules that can help in the transport or delivery of bioactive or functional substances.

Thus, in another aspect, the invention provides formulations of compounds of the invention. In addition to the compound of the invention, the formulations include a second species that interacts with the compound of the invention to alter a characteristic of the compound, such as its water solubility. In an exemplary embodiment, the compound of the invention includes a lipid moiety, as described above. The second species includes a lipophilic domain that interacts with the lipid moiety of the compound of the invention. The second species also includes a hydrophilic moiety that enhances the water solubility of the complex formed between the compound of the invention and the second species.

In an exemplary embodiment, the invention provides a formulation comprising compound of the invention and a second compound having the formula:

A-B wherein A is a hydrophobic domain; and B is a hydrophilic domain covalently bound to A.

Figure 2:
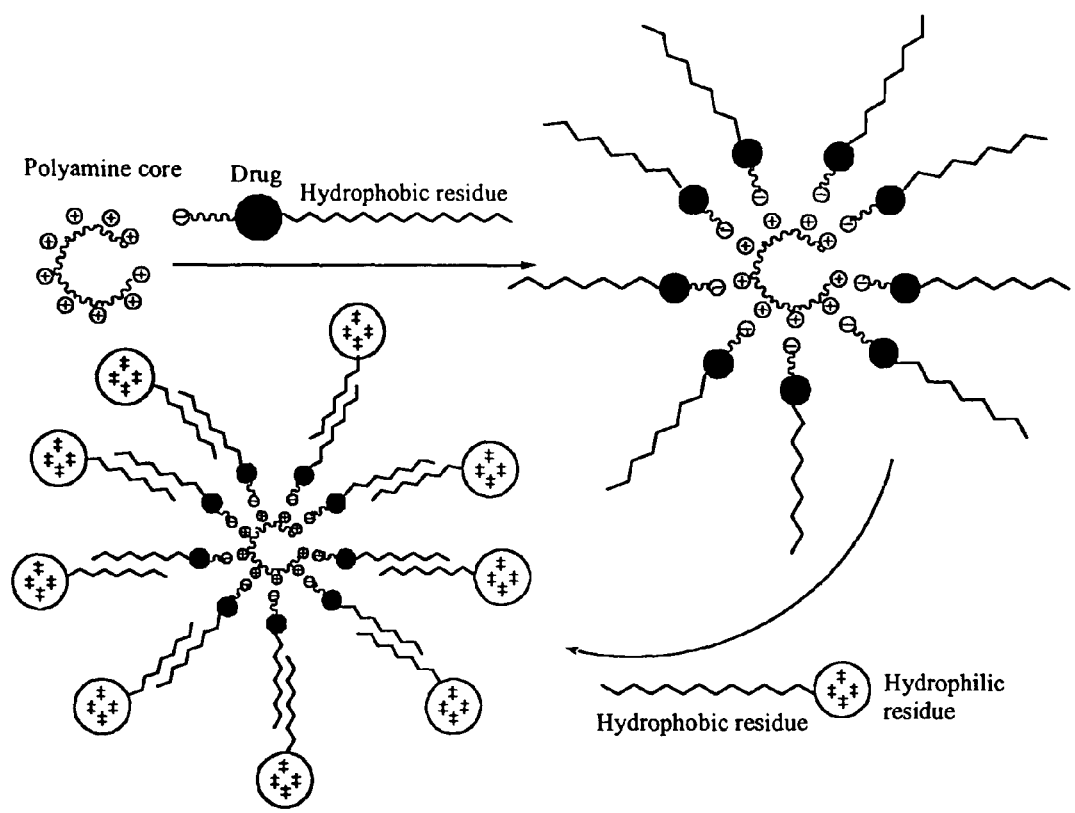
FIG. 2 is an illustration of the complexes of the invention formed between the pharmacophore modified with a hydrophobic modifying group and a poly-ion.
Figure 3:
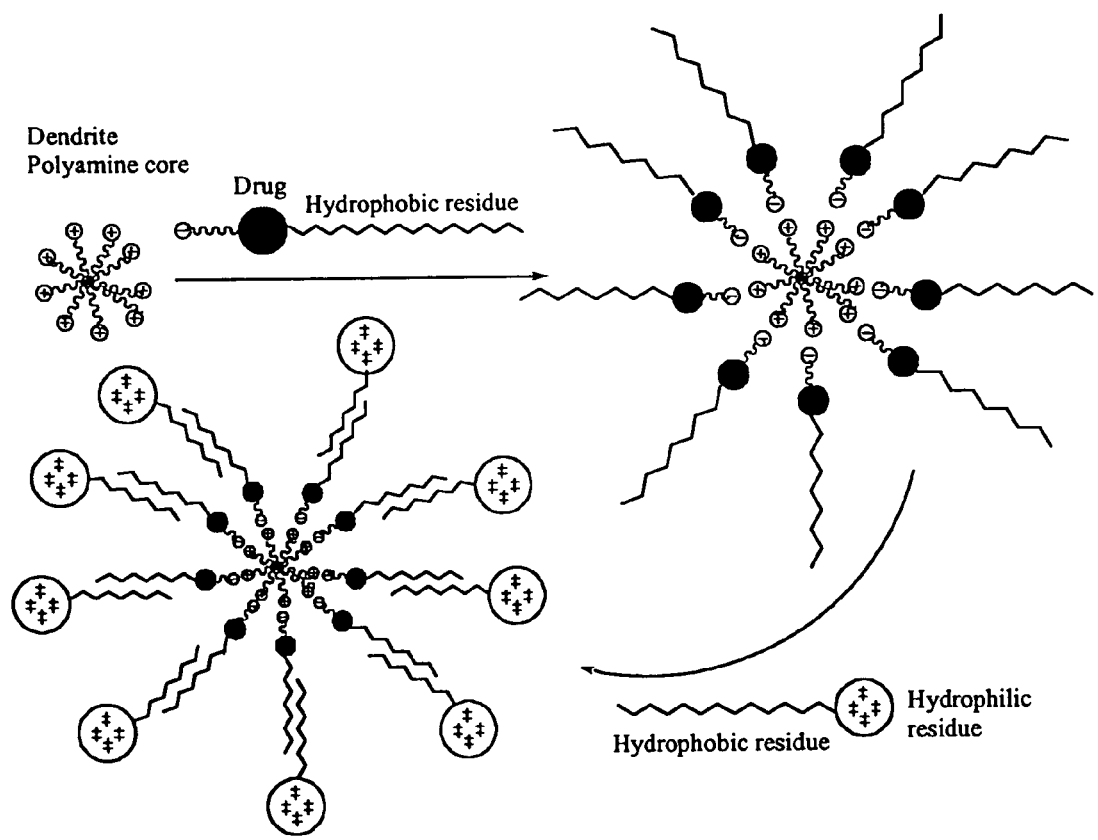
FIG. 3 is an illustration of the complexes of the invention formed between the pharmacophore modified with a hydrophobic modifying group and a dendrimeric poly-ion.

An exemplary embodiment of the formulations of the invention is set forth in FIG. 2, which is an illustration of the complexes of the invention formed between the pharmacophore modified with a hydrophobic modifying group and a poly-ion, such as a polycation. Another exemplary embodiment is provided by FIG. 3, which is an illustration of the complexes of the invention formed between the pharmacophore modified with a hydrophobic modifying group and a dendrimeric poly-ion.

In a preferred embodiment, the formulations of the invention are aqueous formulations.

If desired, the formulations may form aggregates. An example of such formulations is constructed of one or more charged lipids in association with one or more polymer bearing lipids, optionally in association with one or more neutral lipids. The charged lipids may either be anionic or cationic. Typically, the lipids are aggregated in the presence of a multivalent species, such as a counter ion, opposite in charge to the charged lipid. For delivery of prodrugs and/or bioactive agents to selective sites in vivo, aggregates of preferably under 2 microns, more preferably under 0.5 microns, and even more preferably under 200 nm are desired. Most preferably the lipid aggregates are under 200 nm in size and may be as small as 5-10 nm in size.

When the charged lipid is anionic, a multivalent (divalent, trivalent, etc.) cationic material may be used to form aggregates. It is contemplated that cations in all of their ordinary valence states will be suitable for forming aggregates of compounds of the invention.

When the charged lipid is cationic, an anionic material, for example, may be used to form aggregates. Preferably, the anionic material is multivalent, such as, for example, divalent. Examples of useful anionic materials include monatomic and polyatomic anions such as carboxylate ions, sulfide ion, sulfite ions, sulfate ions, oxide ions, nitride ions, carbonate ions, and phosphate ions. Anions of ethylene diamine tetraacetic acid (EDTA), diethylene triamine pentaacetic acid (DTPA), and 1,4,7,10-tetraazocyclododecane-N',N',N'',N'''-tetraacetic acid (DOTA) may also be used. Further examples of useful anionic materials include anions of polymers and copolymers of acrylic acid, methacrylic acid, other polyacrylates and methacrylates, polymers with pendant $SO_3H$ groups, such as sulfonated polystyrene, and polystyrenes containing carboxylic acid groups.

In an exemplary embodiment, the composition of the invention is charged and a polyion, e.g. a charged dendrimer is used to form an aggregate. Dendrimers are polymers of spherical or other three-dimensional shapes that have precisely defined compositions and that possess a precisely defined molecular weight. Dendrimers can be synthesized as water-soluble macromolecules through appropriate selection of internal and external moieties. See, U.S. Pat. Nos. 4,507,466 and 4,568,737, incorporated by reference herein. The first well-defined, symmetrical, dendrimer family was the polyamidoamine (PAMAM) dendrimers, which are manufactured by the Dow Chemical Company. Since the synthesis and characterization of the first dendrimers, a large array of dendrimers of diverse sizes and compositions has been prepared. See, for example, Liu M. and Frechet J. M. J., *Pharm. Sci. Tech. Today* 2(11): 393 (1999).

Dendritic macromolecules are characterized by a highly branched, layered structure with a multitude of chain ends. Dendrimers are particularly well defined with a very regular and almost size monodisperse structure, while hyperbranched polymers are less well defined and have a broader polydispersity. Dendritic macromolecules are usually constructed from $AB_x$ monomers. Hyperbranched polymers are generally obtained via a polymerization reaction that generally takes place in a single series of propagation steps. Dendrimers are generally obtained by multistep iterative syntheses using either a divergent (Tomalia et al., U.S. Pat. Nos. 4,435,548; 4,507,466, 4,558,120; 4,568,737; 5,338,532) or a convergent growth approach (Hawker et al., U.S. Pat. No. 5,041,516).

Dendrimers have been conjugated with various pharmaceutical materials as well as with various targeting molecules that may function to direct the conjugates to selected body locations for diagnostic or therapeutic applications. See, for example, WO 8801178, incorporated by reference herein. Dendrimers have been used to covalently couple synthetic porphyrins (e.g., hemes, chlorophyll) to antibody molecules as a means for increasing the specific activity of radiolabeled antibodies for tumor therapy and diagnosis. Roberts et al., *Bioconjug. Chemistry* 1:305-308 (1990); Tomalia et al., U.S. Pat. No. 5,714,166.

Exemplary dendrimers of use in this aspect of the invention include the well-known PAMAM poly(amidoamine) dendrimers or ASTRAMOL poly(propyleneimine), in part as a result of their easy transformation into ionically charged species.

In an exemplary embodiment, the hydrophilic domain of component B, includes a hydrophilic oligomer or polymer. Suitable hydrophilic groups include, for example, polyalkyleneoxides such as, for example, polyethylene glycol (PEG) and polypropylene glycol (PPG), polyvinylpyrrolidones, polyvinylmethylethers, polyacrylamides, such as, for example, polymethacrylamides, polydimethylacrylamides and polyhydroxypropylmethacrylamides, polyhydroxyethyl acrylates, polyhydroxypropyl methacrylates, polymethyloxazolines, polyethyloxazolines, polyhydroxyethyloxazolines, polyhyhydroxypropyloxazolines, polyvinyl alcohols, polyphosphazenes, poly(hydroxyalkylcarboxylic acids), polyoxazolidines, polyaspartamide, and polymers of sialic acid (polysialics). The hydrophilic polymers are preferably selected from the group consisting of PEG, PPG, polyvinylalcohol and polyvinylpyrrolidone and copolymers thereof, with PEG and PPG polymers being more preferred and PEG polymers being even more preferred.

In another exemplary embodiment, the compound of the invention has an oral bioavailability of at least 15%, more preferably at least 20% of the administered dose. An exemplary formulation of a compound of the invention that provides the desired oral bioavailability is an acid addition salt of the heterocyclic compound of the invention. The acid addition salt may be either a salt of a mineral or organic acid, e.g., a carboxylic acid.

In accordance with the above embodiment, the inventors have surprisingly discovered that carboxylic acid salts of the compounds of the invention provide the desired oral bioavailability. As shown in Table 2, the oral bioavailability of an exemplary carboxylic acid salt of DHAdC is approximately 23%, which is more than twice the oral bioavailability of the corresponding base.

TABLE 2[a]

|  | DHAdC-base (9) (IV) | DHAdC-base (9) (Oral) | DHAdC-palmitate (27) Oral |
|---|---|---|---|
| Cmax (ng/ml) | 40,034 | 1,858 | 2,816 |
| AUC∞(ng-hr/ml) | 74,975 | 8,538 | 17,552 |
| Half-life (hr) | 1.8 | 0.8 | 0.7 |
| % oral bioavailability |  | 11 | 23 |

[a]Comparison of pharmacokinetics of 5,6-dihydro-5-aza-2'deoxycytidine (DHAdC) base given to rats parenterally (IV) and orally to DHAdC-palmitate.
Cmax: maximum concentration in plasma,
AUC: area under the curve Carrier Molecules The compounds of the invention and their formulations can also include a carrier molecule, useful to target the pharmacophore to a specific region within the body or tissue, or to a selected species or structure in vitro. Selective targeting of an agent by its attachment to a species with an affinity for the targeted region is well known in the art. Both small molecule and polymeric targeting agents are of use in the present invention.

In an exemplary embodiment, a compound of the invention is linked to a targeting agent that selectively delivers it to a cell, organ or region of the body. Exemplary targeting agents such as antibodies, ligands for receptors, lectins, saccharides, antibodies, and the like are recognized in the art and are useful without limitation in practicing the present invention. Other targeting agents include a class of compounds that do not include specific molecular recognition motifs include macromolecules such as poly(ethylene glycol), polysaccharide, polyamino acids and the like, which add molecular mass to the ligand. The ligand-targeting agent conjugates of the invention are exemplified by the use of a nucleic acid-ligand conjugate. The focus on ligand-oligonucleotide conjugates is for clarity of illustration and is not limiting of the scope of targeting agents to which the ligands (or complexes) of the invention can be conjugated. Moreover, it is understood that "ligand" refers to both the free ligand and its metal complexes.

Exemplary nucleic acid targeting agents include aptamers, antisense compounds, and nucleic acids that form triple helices. Typically, a hydroxyl group of a sugar residue, an amino group from a base residue, or a phosphate oxygen of the nucleotide is utilized as the needed chemical functionality to couple the nucleotide-based targeting agent to the ligand. However, one of skill in the art will readily appreciate that other "non-natural" reactive functionalities can be appended to a nucleic acid by conventional techniques. For example, the hydroxyl group of the sugar residue can be converted to a mercapto or amino group using techniques well known in the art.

Aptamers (or nucleic acid antibody) are single- or double-stranded DNA or single-stranded RNA molecules that bind specific molecular targets. Generally, aptamers function by inhibiting the actions of the molecular target, e.g., proteins, by binding to the pool of the target circulating in the blood. Aptamers possess chemical functionality and thus, can covalently bond to ligands, as described herein.

Although a wide variety of molecular targets are capable of forming non-covalent but specific associations with aptamers, including small molecules drugs, metabolites, cofactors, toxins, saccharide-based drugs, nucleotide-based drugs, glycoproteins, and the like, generally the molecular target will comprise a protein or peptide, including serum proteins, kinins, eicosanoids, cell surface molecules, and the like. Examples of aptamers include Gilead's antithrombin inhibitor GS 522 and its derivatives (Gilead Science, Foster City, Calif.). See also, Macaya et al. Proc. Natl. Acad. Sci. USA 90: 3745-9 (1993); Bock et al. Nature (London) 355: 564-566 (1992) and Wang et al. Biochem. 32: 1899-904 (1993).

Aptamers specific for a given biomolecule can be identified using techniques known in the art. See, e.g., Toole et al. (1992) PCT Publication No. WO 92/14843; Tuerk and Gold (1991) PCT Publication No. WO 91/19813; Weintraub and Hutchinson (1992) PCT Publication No. 92/05285; and Ellington and Szostak, Nature 346: 818 (1990). Briefly, these techniques typically involve the complexation of the molecular target with a random mixture of oligonucleotides. The aptamer-molecular target complex is separated from the uncomplexed oligonucleotides. The aptamer is recovered from the separated complex and amplified. This cycle is repeated to identify those aptamer sequences with the highest affinity for the molecular target.

For diseases that result from the inappropriate expression of genes, specific prevention or reduction of the expression of such genes represents an ideal therapy. In principle, production of a particular gene product may be inhibited, reduced or shut off by hybridization of a single-stranded deoxynucleotide or ribodeoxynucleotide complementary to an accessible sequence in the mRNA, or a sequence within the transcript that is essential for pre-mRNA processing, or to a sequence within the gene itself. This paradigm for genetic control is often referred to as antisense or antigene inhibition. Additional efficacy is imparted by the conjugation to the nucleic acid of an alkylating agent, such as those of the present invention.

Antisense compounds are nucleic acids designed to bind and disable or prevent the production of the mRNA responsible for generating a particular protein. Antisense compounds include antisense RNA or DNA, single or double stranded, oligonucleotides, or their analogs, which can hybridize specifically to individual mRNA species and prevent transcription and/or RNA processing of the mRNA species and/or translation of the encoded polypeptide and thereby effect a reduction in the amount of the respective encoded polypeptide. Ching et al. Proc. Natl. Acad. Sci. U.S.A. 86: 10006-10010 (1989); Broder et al. Ann. Int. Med. 113: 604-618 (1990); Loreau et al. FEBS Letters 274: 53-56 (1990); Holcenberg et al. WO91/11535; WO91/09865; WO91/04753; WO90/13641; WO 91/13080, WO 91/06629, and EP 386563). Due to their exquisite target sensitivity and selectivity, antisense oligonucleotides are useful for delivering therapeutic agents, such as the ligands of the invention to a desired molecular target.

The site specificity of nucleic acids (e.g., antisense compounds and triple helix drugs) is not significantly affected by modification of the phosphodiester linkage or by chemical modification of the oligonucleotide terminus. Consequently, these nucleic acids can be chemically modified; enhancing the overall binding stability, increasing the stability with respect to chemical degradation, increasing the rate at which the oligonucleotides are transported into cells, and conferring chemical reactivity to the molecules. The general approach to constructing various nucleic acids useful in antisense therapy has been reviewed by van der Krol et al., Biotechniques 6: 958-976 (1988) and Stein et al. Cancer Res. 48: 2659-2668 (1988). Therefore, in an exemplary embodiment, the ligands of the invention are conjugated to a nucleic acid by modification of the phosphodiester linkage.

Moreover, aptamers, antisense compounds and triple helix drugs bearing compounds of the invention can also can include nucleotide substitutions, additions, deletions, or transpositions, so long as specific hybridization to or association with the relevant target sequence is retained as a functional property of the oligonucleotide. For example, some embodiments will employ phosphorothioate analogs which are more resistant to degradation by nucleases than their naturally occurring phosphate diester counterparts and are thus expected to have a higher persistence in vivo and greater potency (see, e.g., Campbell et al., *J. Biochem. Biophys. Methods* 20: 259-267(1990)). Phosphoramidate derivatives of oligonucleotides also are known to bind to complementary polynucleotides and have the additional capability of accommodating covalently attached ligand species and will be amenable to the methods of the present invention. See, for example, Froehier et al., *Nucleic Acids Res.* 16(11): 4831 (1988).

Terminal modification also provides a useful procedure to conjugate the pharmacophore to the nucleic acid, modify cell type specificity, pharmacokinetics, nuclear permeability, and absolute cell uptake rate for oligonucleotide pharmaceutical agents. For example, an array of substitutions at the 5' and 3' ends to include reactive groups are known, which allow covalent attachment of the cytotoxins. See, e.g., OLIGODEOXYNUCLE- OTIDES: ANTISENSE INHIBITORS OF GENE EXPRESSION, (1989) Cohen, Ed., CRC Press; PROSPECTS FOR ANTISENSE NUCLEIC ACID THERAPEUTICS FOR CANCER AND AIDS, (1991), Wickstrom, Ed., Wiley-Liss; GENE REGULATION: BIOLOGY OF ANTISENSE RNA AND DNA, (1992) Erickson and Izant, Eds., Raven Press; and ANTISENSE RNA AND DNA, (1992), Murray, Ed., Wiley-Liss. For general methods relating to antisense compounds, see, ANTISENSE RNA AND DNA, (1988), D. A. Melton, Ed., Cold Spring Harbor Laboratory, Cold Spring Harbor, N.Y.).

In another exemplary embodiment, the invention utilizes a peptide-based targeting moiety. Generally speaking, peptides that are particularly useful as targeting ligands include natural, modified natural, or synthetic peptides that incorporate additional modes of resistance to degradation by vascularly circulating esterases, amidases, or peptidases. Suitable targeting ligands, and methods for their preparation, will be readily apparent to one skilled in the art, in view of the disclosure herein. Exemplary targeting ligands in the present invention include cell adhesion molecules (CAM), among which are, for example, cytokines, integrins, cadherins, immunoglobulins and selectins.

Regarding targeting to specific cell types, for example, endothelial cells, suitable targeting ligands include, for example, one or more of the following: growth factors, including, for example, basic fibroblast growth factor (bFGF), acidic fibroblast growth factor (aFGF), transforming growth factor-alpha (TGF-α), transforming growth factor-beta (TGF-β), platelet-derived endothelial cell growth factor (PD-ECGF) vascular endothelial growth factor (VEGF) and human growth factor (HGF); angiogenin; tumor necrosis factors, including tumor necrosis factor-α (TNF-α) and tumor necrosis factor-β (TNF-β), and receptor antibodies and fragments thereof to tumor necrosis factor (TNF) receptor 1 or 2 family, including, for example, TNF-R1, TNF-R2, FAS, TNFR-RP, NGF-R, CD30, CD40, CD27, OX40 and 4-1BB; copper-containing polyribonucleotide angiotropin with a molecular weight of about 4,500, as well as low molecular weight non-peptide angiogenic factors, such as 1-butyryl glycerol; the prostaglandins, including, for example, prostaglandin $E_1$ (PGE$_1$) and prostaglandin $E_2$ (PGE$_2$); nicotinamide; adenosine; dipyridamole; dobutamine; hyaluronic acid degradation products, such as, for example, degradation products resulting from hydrolysis of β-linkages, including hyalobiuronic acid; angiogenesis inhibitors, including, for example, collagenase inhibitors; minocycline; medroxyprogesterone; chitin chemically modified with 6-O-sulfate and 6-O-carboxymethyl groups; angiostatic steroids, such as tetrahydrocortisol; and heparin, including fragments of heparin, such as, for example, fragments having a molecular weight of about 6,000, admixed with steroids, such as, for example, cortisone or hydrocortisone; angiogenesis inhibitors, including angioinhibin (AGM-1470—an angiostatic antibiotic); platelet factor 4; protamine; sulfated polysaccharide peptidoglycan complexes derived from the bacterial wall of an *Arthobacter* species; fungal-derived angiogenesis inhibitors, such as fumagillin derived from *Aspergillus fumigatus*; D-penicillamine; gold thiomalate; thrombospondin; vitamin $D_3$ analogues; interferons, including, for example, α-interferon, β-interferon and γ-interferon; cytokines and cytokine fragments, such as the interleukins, including, for example, interleukin-1 (IL-1), interleukin-2 (IL-2), interleukin-3 (IL-3), interleukin-5 (IL-5) and interleukin-8 (IL-8); erythropoietin; a 20-mer peptide or smaller for binding to receptor or antagonists to native cytokines; granulocyte macrophage colony stimulating factor (GMCSF); LTB$_4$ leukocyte receptor antagonists; heparin, including low molecular weight fragments of heparin or analogues of heparin; simple sulfated polysaccharides, such as cyclodextrins, including α-, β- and γ-cyclodextrin; tetradecasulfate; transferrin; ferritin; platelet factor 4; protamine; Gly-His-Lys complexed to copper; ceruloplasmin; (12R)-hydroxyeicosatrienoic acid; okadaic acid; lectins; antibodies; CD11a/CD18; and Very Late Activation Integrin-4 (VLA4). Peptides that bind the interleukin-1 (IL-1) receptor may be used.

The cadherin family of cell adhesion molecules may also be used as targeting ligands, including for example, the E-, N-, and P-cadherins, cadherin-4, cadherin-5, cadherin-6, cadherin-7, cadherin-8, cadherin-9, cadherin-10, and cadherin-11; and most preferably cadherin C-5. Further, antibodies directed to cadherins, such as, for example, the monoclonal antibody Ec6C10, may be used to recognize cadherins expressed locally by specific endothelial cells.

A wide variety of different targeting ligands can be selected to bind to the cytoplasmic domains of the ELAM molecules. Targeting ligands in this regard may include lectins, a wide variety of carbohydrate or sugar moieties, antibodies, antibody fragments, Fab fragments, such as, for example, Fab'2, and synthetic peptides, including, for example, Arginine-Glycine-Aspartic Acid (R-G-D) which may be targeted to wound healing. While many of these materials may be derived from natural sources, some may be synthesized by molecular biological recombinant techniques and others may be synthetic in origin. Peptides may be prepared by a variety of different combinatorial chemistry techniques as are now known in the art. Targeting ligands derived or modified from human leukocyte origin, such as CD11a/CD18, and leukocyte cell surface glycoprotein (LFA-1), may also be used as these are known to bind to the endothelial cell receptor ICAM-1. The cytokine inducible member of the immunoglobulin superfamily, VCAM-1, which is mononuclear leukocyte-selective, may also be used as a targeting ligand. VLA4, derived from human monocytes, may be used to target VCAM-1.

As with the endothelial cells discussed above, a wide variety of peptides, proteins and antibodies may be employed as targeting ligands for targeting epithelial cells. Preferably, a peptide, including synthetic, semi-synthetic or naturally-occurring peptides, with high affinity to the epithelial cell target receptor may be selected, with synthetic peptides being more preferred. In connection with these preferred embodiments, peptides having from about 5 to about 15 amino acid residues are preferred. Antibodies may be used as whole antibody or antibody fragments, for example, Fab or Fab'2, either of natural or recombinant origin. The antibodies of natural origin may be of animal or human origin, or may be chimeric (mouse/human). Human recombinant or chimeric antibodies are preferred and fragments are preferred to whole antibody.

In one embodiment of the invention, the targeting ligands are directed toward lymphocytes which may be T-cells or B-cells, with T-cells being the preferred target. To select a class of targeted lymphocytes, a targeting ligand having specific affinity for that class is employed. For example, an anti CD4 antibody can be used for selecting the class of T-cells harboring CD4 receptors, an anti CD-8 antibody can be used for selecting the class of T-cells harboring CD-8 receptors, an anti CD-34 antibody can be used for selecting the class of T-cells harboring CD-34 receptors, etc. A lower molecular weight ligand is preferably employed, e.g., Fab or a peptide fragment. For example, an OKT3 antibody or OKT3 antibody fragment may be used.

When a receptor for a class of T-cells or clones of T-cells is selected, the steroid prodrug will be delivered to that class of cells. Using HLA-derived peptides, for example, will allow selection of targeted clones of cells expressing reactivity to HLA proteins.

Another useful area for targeted prodrug delivery involves the interleukin-2 (IL-2) system. IL-2 is a t-cell growth factor produced following antigen or mitogen induced stimulation of lymphoid cells. Among the cell types producing IL-2 are $CD4^+$ and $CD8'$-cells and large granular lymphocytes, as well as certain t-cell tumors. IL-2 receptors are glycoproteins expressed on responsive cells. They are notable in connection with the present invention because they are readily endocytosed into lysosomal inclusions when bound to IL-2. The ultimate effect of this endocytosis depends on the target cell, but among the notable in vivo effects are regression of transplantable murine tumors, human melanoma or renal cell cancer. IL-2 has also been implicated in antibacterial and antiviral therapies and plays a role in allograft rejection. In addition to IL-2 receptors, preferred targets include the anti-IL-2 receptor antibody, natural IL-2 and an IL-2 fragment of a 20-mer peptide or smaller generated by phage display that binds to the IL-2 receptor.

Although not intending to be bound by any particular theory of operation, IL-2 can be conjugated to the prodrugs and/or other delivery vehicles and thus mediate the targeting of cells bearing IL-2 receptors. Endocytosis of the ligand-receptor complex would then deliver the steroid to the targeted cell, thereby inducing its death through apoptosis—independent and superceding any proliferative or activating effect that IL-2 would promote alone.

Additionally, an IL-2 peptide fragment which has binding affinity for IL-2 receptors can be incorporated either by direct attachment to a reactive moiety on the steroid prodrug or via a spacer or linker molecule with a reactive end such as an amine, hydroxyl, or carboxylic acid functional group. Such linkers are well known in the art and may comprise from 3 to 20 amino acid residues. Alternatively, D-amino acids or derivatized amino acids may be used which avoid proteolysis in the target tissue.

Still other systems which can be used in the present invention include IgM-mediated endocytosis in B-cells or a variant of the ligand-receptor interactions described above wherein the T-cell receptor is CD2 and the ligand is lymphocyte function-associated antigen 3 (LFA-3), as described, for example, by Wallner et al, *J Experimental Med.*, 166: 923-932 (1987), the disclosure of which is hereby incorporated by reference herein in its entirety.

The targeting ligand may be incorporated in the present stabilizing materials in a variety of ways. Generally speaking, the targeting ligand may be incorporated in the present stabilizing materials by being associated covalently or non-covalently with one or more of the stabilizing materials which are included in the compositions including, for example, the prodrugs, lipids, proteins, polymers, surfactants, and/or auxiliary stabilizing materials. In preferred form, the targeting ligand may be associated covalently with one or more of the aforementioned materials contained in the present stabilizing materials. Preferred stabilizing materials of the present invention comprise prodrugs, lipid, protein, polymer or surfactant compounds. In these compositions, the targeting ligands are preferably associated covalently with the prodrug, lipid, protein, polymer or surfactant compounds.

The covalent linking of the targeting ligands to the pharmacophores in the present compositions, including the prodrugs, and lipid components is accomplished using synthetic organic techniques which are readily apparent to one of ordinary skill in the art in view of the present disclosure. For example, the targeting ligands may be linked to the materials, including the lipids, via the use of well-known coupling or activation agents. As known to the skilled artisan, activating agents are generally electrophilic, which can be employed to elicit the formation of a covalent bond. Exemplary activating agents include, for example, carbonyldiimidazole (CDI), dicyclohexylcarbodiimide (DCC), diisopropylcarbodiimide (DIC), methyl sulfonyl chloride, Castro's Reagent, and diphenyl phosphoryl chloride.

The covalent bonds optionally involve crosslinking and/or polymerization. Crosslinking preferably refers to the attachment of two chains of polymer molecules by bridges, composed of an element, a group, or a compound, which join certain carbon atoms of the chains by covalent chemical bonds. For example, crosslinking may occur in polypeptides that are joined by the disulfide bonds of the cystine residue. Crosslinking may be achieved, for example, by (1) adding a chemical substance (crosslinking agent) and exposing the mixture to heat, or (2) subjecting a polymer to high-energy radiation. A variety of crosslinking agents, or "tethers", of different lengths and/or functionalities are described, for example, in R. L. Lunbland, Techniques in Protein Modification, CRC Press, Inc., Ann Arbor, Mich., pp. 249-68 (1995), the disclosures of which is hereby incorporated herein by reference in its entirety. Exemplary crosslinkers include, for example, 3,3'-dithiobis(succinimidylpropionate), dimethyl suberimidate, and its variations thereof, based on hydrocarbon length, and bis-N-maleimido-1,8-octane.

Standard peptide methodology may be used to link the targeting ligand to the compound of the invention utilizing linker groups having two unique terminal functional groups. Bifunctional hydrophilic polymers, and especially bifunctional PEGs, may be synthesized using standard organic synthetic methodologies. In addition, many of these materials are available commercially, such as, for example, α-amino-ω-carboxy-PEG that is commercially available from Shearwater Polymers (Huntsville, Ala.). An advantage of using a PEG material as the linking group is that the size of the PEG can be varied such that the number of monomeric subunits of ethylene glycol may be as few as, for example, about 5, or as many as, for example, about 500 or even greater. Accordingly, the "tether" or length of the linkage may be varied, as desired. This may be important depending, for example, on the particular targeting ligand employed.

In an exemplary embodiment, the terminus of the hydrophilic spacer, such as polyethylene glycol ethylamine, which contains a reactive group, such as an amine or hydroxyl group, is used to bind a targeting ligand to a compound of the invention. For example, polyethylene glycol ethylamine may be reacted with N-succinimidylbiotin or p-nitrophenylbiotin to introduce onto the spacer a useful coupling group.

The carrier molecules may also be used as a backbone for compounds of the invention that are poly- or multi-valent species, including, for example, species such as dimers, trimers, tetramers and higher homologs of the compounds of the invention. The poly- and multi-valent species can be assembled from a single species or more than one species of the invention. For example, a dimeric construct can be "homo-dimeric" or "heterodimeric." Moreover, poly- and multi-valent constructs in which a compound of the invention, or a reactive analogue thereof, is attached to an oligomeric or polymeric framework (e.g., polylysine, dextran, hydroxyethyl starch and the like) are within the scope of the present invention. The framework is preferably polyfunctional (i.e. having an array of reactive sites for attaching compounds of the invention). Moreover, the framework can be derivatized with a single species of the invention or more than one species of the invention.

Moreover, the properties of the carrier molecule can be selected to afford compounds having water-solubility that is enhanced relative to analogous compounds that are not similarly functionalized. Thus, any of the substituents set forth herein can be replaced with analogous radicals that have enhanced water solubility. For example, it is within the scope of the invention to, for example, replace a hydroxyl group with a diol, or an amine with a quaternary amine, hydroxylamine or similar more water-soluble moiety. In a preferred embodiment, additional water solubility is imparted by substitution at a site not essential for the activity towards the ion channel of the compounds set forth herein with a moiety that enhances the water solubility of the parent compounds. Methods of enhancing the water-solubility of organic compounds are known in the art. Such methods include, but are not limited to, functionalizing an organic nucleus with a permanently charged moiety, e.g., quaternary ammonium, or a group that is charged at a physiologically relevant pH, e.g. carboxylic acid, amine. Other methods include, appending to the organic nucleus hydroxyl- or amine-containing groups, e.g. alcohols, polyols, polyethers, and the like. Representative examples include, but are not limited to, polylysine, polyethyleneimine, poly(ethyleneglycol) and poly(propyleneglycol). Suitable functionalization chemistries and strategies for these compounds are known in the art. See, for example, Dunn, R. L., et al., Eds. POLYMERIC DRUGS AND DRUG DELIVERY SYSTEMS, ACS Symposium Series Vol. 469, American Chemical Society, Washington, D.C. 1991.

Pharmaceutical Formulations

In another preferred embodiment, the present invention provides a pharmaceutical formulation comprising a dendrimer-agent conjugate and a pharmaceutically acceptable carrier.

The compounds described herein, or pharmaceutically acceptable addition salts or hydrates thereof, can be delivered to a patient using a wide variety of routes or modes of administration. Suitable routes of administration include, but are not limited to, inhalation, transdermal, oral, rectal, transmucosal, intestinal and parenteral administration, including intramuscular, subcutaneous and intravenous injections.

The compounds described herein, or pharmaceutically acceptable salts, and/or hydrates thereof, may be administered singly, in combination with other compounds of the invention, and/or in cocktails combined with other therapeutic agents. Of course, the choice of therapeutic agents that can be co-administered with the compounds of the invention will depend, in part, on the condition being treated.

For example, when administered to a patient undergoing cancer treatment, the compounds may be administered in cocktails containing other bioactive agents, such as anti-cancer agents and/or supplementary potentiating agents. The compounds may also be administered in cocktails containing agents that treat the side-effects of radiation therapy, such as anti-emetics, radiation protectants, etc.

Other suitable bioactive agents include, for example, antineoplastic agents, such as platinum compounds (e.g., spiroplatin, cisplatin, and carboplatin), methotrexate, adriamycin, taxol, mitomycin, ansamitocin, bleomycin, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, mitomycin, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, etoposide (VP-16), interferon α-2a, interferon α-2b, teniposide (VM-26), vinblastine sulfate (VLB), vincristine sulfate, bleomycin, bleomycin sulfate, methotrexate, adriamycin, and arabinosyl; blood products such as parenteral iron, hemin, hematoporphyrins and their derivatives; biological response modifiers such as muramyldipeptide, muramyltripeptide, microbial cell wall components, lymphokines (e.g., bacterial endotoxin such as lipopoly-saccharide, macrophage activation factor), subunits of bacteria (such as Mycobacteria and Corynebacteria), the synthetic dipeptide N-acetyl-muramyl-L-alanyl-D-isoglutamine; antifungal agents such as ketoconazole, nystatin, griseofulvin, flucytosine (5-fc), miconazole, amphotericin B, ricin, and β-lactam antibiotics (e.g., sulfazecin); hormones and steroids such as growth hormone, melanocyte stimulating hormone, estradiol, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunsolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide and fludrocortisone acetate; vitamins such as cyanocobalamin neinoic acid, retinoids and derivatives such as retinol palmitate, and α-tocopherol; peptides, such as manganese super oxide dimutase; enzymes such as alkaline phosphatase; anti-allergic agents such as amelexanox; anti-coagulation agents such as phenprocoumon and heparin; circulatory drugs such as propranolol; metabolic potentiators such as glutathione; antituberculars such as para-aminosalicylic acid, isoniazid, capreomycin sulfate cycloserine, ethambutol hydrochloride ethionamide, pyrazinamide, rifampin, and streptomycin sulfate; antivirals such as acyclovir, amantadine azidothymidine (AZT or Zidovudine), ribavirin, amantadine, vidarabine, and vidarabine monohydrate (adenine arabinoside, ara-A); antianginals such as diltiazem, nifedipine, verapamil, erythrityl tetranitrate, isosorbide dinitrate, nitroglycerin (glyceryl trinitrate) and pentaerythritol tetranitrate; anticoagulants such as phenprocoumon, heparin; antibiotics such as dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin G, penicillin V, ticarcillin rifampin and tetracycline; antiinflammatories such as diffinisal, ibuprofen, indomethacin, meclofenamate, mefenamic acid, naproxen, oxyphenbutazone, phenylbutazone, piroxicam, sulindac, tolmetin, aspirin and salicylates; antiprotozoans such as chloroquine, hydroxychloroquine, metronidazole, quinine and meglumine antimonate; antirheumatics such as penicillamine; narcotics such as paregoric; opiates such as codeine, heroin, methadone, morphine and opium; cardiac glycosides such as deslanoside, digitoxin, digoxin, digitalin and digitalis; neuromuscular blockers such as atracurium besylate, gallamine triethiodide, hexafluorenium bromide, metocurine iodide, pancuronium bromide, succinylcholine chloride (suxamethonium chloride), tubocurarine chloride and vecuronium bromide; sedatives (hypnotics) such as amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam; local anesthetics such as bupivacaine hydrochloride, chloroprocaine hydrochloride, etidocaine hydrochloride, lidocaine hydrochloride, mepivacaine hydrochloride, procaine hydrochloride and tetracaine hydrochloride; general anesthetics such as droperidol, etomidate, fentanyl citrate with droperidol, ketamine hydrochloride, methohexital sodium and thiopental sodium; and radioactive particles or ions such as strontium, iodide rhenium and yttrium. In certain referred embodiments, the bioactive agent is a monoclonal antibody, such as a monoclonal antibody capable of binding to melanoma antigen.

The active compound(s) of the invention are administered per se or in the form of a pharmaceutical composition wherein the active compound(s) is in admixture with one or more pharmaceutically acceptable carriers, excipients or diluents. Pharmaceutical compositions for use in accordance with the present invention are typically formulated in a conventional manner using one or more physiologically acceptable carriers comprising excipients and auxiliaries, which facilitate processing of the active compounds into preparations which, can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the dendrimer with a solid excipient, optionally grinding the resulting mixture, and processing the mixture of granules, after adding suitable auxiliaries, if desired, to obtain tablets or dragee cores. Suitable excipients are, for example, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, poly(ethylene oxide), and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations, which can be used orally, include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents may be added, such as the cross-linked polyvinyl pyrrolidone, agar, or alginic acid or a salt thereof such as sodium alginate.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as poly(ethylene oxide).

Microarrays

The invention also provides microarrays including immobilized compounds of the invention and compounds functionalized with compounds of the invention. Moreover, the invention provides methods of interrogating microarrays using probes that are functionalized with compounds of the invention. The immobilized species and the probes are selected from substantially any type of molecule, including, but not limited to, small molecules, peptides, enzymes nucleic acids and the like.

Nucleic acid microarrays consisting of a multitude of immobilized nucleic acids are revolutionary tools for the generation of genomic information, see, Debouck et al., in supplement to *Nature Genetics,* 21:48-50 (1999). The discussion that follows focuses on the use of compounds of the invention in conjunction with nucleic acid microarrays. This focus is intended to be illustrative and does not limit the scope of materials with which this aspect of the present invention can be practiced.

Thus, in another preferred embodiment, the compounds of the present invention are utilized in a microarray format. The compound of the invention, or species bearing a compound of the invention can themselves be components of a microarray or, alternatively they can be utilized as a tool to screen components of a microarray.

In an exemplary embodiment, the microarrays comprise n probes that comprise identical or different nucleic acid sequences. Alternatively, the microarray can comprise a mixture of n probes comprising groups of identical and different nucleic acid sequences identical nucleic acid sequences). In a preferred embodiment, n is a number from 2 to 100, more preferably, from 10 to 1,000, and more preferably from 100 to 10,000. In a still further preferred embodiment, the n probes are patterned on a substrate as n distinct locations in a manner that allows the identity of each of the n locations to be ascertained.

In yet another preferred embodiment, the invention also provides a method for preparing a microarray of n probes. The method includes attaching the probes to selected regions of a substrate. A variety of methods are currently available for making arrays of biological macromolecules, such as arrays nucleic acid molecules.

One method for making ordered arrays of probes on a substrate is a "dot blot" approach. In this method, a vacuum manifold transfers a plurality, e.g., 96, aqueous samples of probes from 3 millimeter diameter wells to a substrate. The probe is immobilized on the porous membrane by baking the membrane or exposing it to UV radiation. A common variant of this procedure is a "slot-blot" method in which the wells have highly-elongated oval shapes.

Another technique employed for making ordered arrays of probes uses an array of pins dipped into the wells, e.g., the 96 wells of a microtiter plate, for transferring an array of samples to a substrate, such as a porous membrane. One array includes pins that are designed to spot a membrane in a staggered fashion, for creating an array of 9216 spots in a 22×22 cm area. See, Lehrach, et al., HYBRIDIZATION FINGERPRINTING IN GENOME MAPPING AND SEQUENCING, GENOME ANALYSIS, Vol. 1, Davies et al, Eds., Cold Springs Harbor Press, pp. 39-81 (1990).

An alternate method of creating ordered arrays of probes is analogous to that described by Pirrung et al. (U.S. Pat. No. 5,143,854, issued 1992), and also by Fodor et al., (*Science,* 251: 767-773 (1991)). This method involves synthesizing different probes at different discrete regions of a particle or other substrate. This method is preferably used with relatively short probe molecules, e.g., less than 20 bases. A related method has been described by Southern et al. (*Genomics,* 13: 1008-1017 (1992)).

Khrapko, et al., *DNA Sequence,* 1: 375-388 (1991) describes a method of making an nucleic acid matrix by spotting DNA onto a thin layer of polyacrylamide. The spotting is done manually with a micropipette.

The substrate can also be patterned using techniques such as photolithography (Kleinfield et al., *J. Neurosci.* 8:4098-120 (1998)), photoetching, chemical etching and microcontact printing (Kumar et al., *Langmuir* 10:1498-511 (1994)). Other techniques for forming patterns on a substrate will be readily apparent to those of skill in the art.

The size and complexity of the pattern on the substrate is limited only by the resolution of the technique utilized and the purpose for which the pattern is intended. For example, using microcontact printing, features as small as 200 nm are layered onto a substrate. See, Xia, Y., *J. Am. Chem. Soc.* 117:3274-75 (1995). Similarly, using photolithography, patterns with features as small as 1 μm are produced. See, Hickman et al., *J. Vac. Sci. Technol.* 12:607-16 (1994). Patterns which are useful in the present invention include those which include features such as wells, enclosures, partitions, recesses, inlets, outlets, channels, troughs, diffraction gratings and the like.

In a presently preferred embodiment, the patterning is used to produce a substrate having a plurality of adjacent wells, indentations or holes to contain the probes. In general, each of these substrate features is isolated from the other wells by a raised wall or partition and the wells do not fluidically communicate. Thus, a particle, or other substance, placed in a particular well remains substantially confined to that well. In another preferred embodiment, the patterning allows the creation of channels through the device whereby an analyte or other substance can enter and/or exit the device.

In another embodiment, the probes are immobilized by "printing" them directly onto a substrate or, alternatively, a "lift off" technique can be utilized. In the lift off technique, a patterned resist is laid onto the substrate, an organic layer is laid down in those areas not covered by the resist and the resist is subsequently removed. Resists appropriate for use with the substrates of the present invention are known to those of skill in the art. See, for example, Kleinfield et al., *J. Neurosci.* 8:4098-120 (1998). Following removal of the photoresist, a second probe, having a structure different from the first probe can be bonded to the substrate on those areas initially covered by the resist. Using this technique, substrates with patterns of probes having different characteristics can be produced. Similar substrate configurations are accessible through microprinting a layer with the desired characteristics directly onto the substrate. See, Mrkish et al. *Ann. Rev. Biophys. Biomol. Struct.* 25:55-78 (1996).

The Methods

The compounds of the present invention can be used to treat viral diseases. In addition, the compounds of the present invention can be used to treat cancer and other diseases of deregulated cellular proliferation.

Without wishing to be bound by theory, for treatment of viral diseases, the nucleoside and nucleotide analogues of the present invention are incorporated into the viral genome. The nucleoside and nucleotide analogues have phosphodiester linkages or acquire phosphodiester linkages, allowing them to be incorporated and extended by a polymerase. The nucleoside and nucleotide analogues have altered base-pairing properties allowing incorporation of mutations into the viral genome, dramatically increasing the viral mutation rate. The increase in viral mutation rate results in decreased viability of progeny virus, thereby inhibiting viral replication. In presently preferred embodiments, 5-aza-2'-deoxycytidine, 5-azacytidine, and derivatives and variants thereof are used to treat DNA viruses, RNA viruses, and retrovirus infections.

The compounds of the present invention can also be used to treat cancer. Without wishing to be bound by theory, the nucleoside and nucleotide analogues of the present invention are incorporated into the nucleic acids of a cancerous cell, either DNA or RNA. The nucleoside and nucleotide analogues have phosphodiester linkages or acquire phosphodiester linkages, allowing them to be incorporated and extended by a polymerase. In one embodiment, the nucleoside and nucleotide analogues have altered base-pairing properties allowing incorporation of mutations into the genome of the cancer cell, dramatically increasing the mutation rate in the cancer cell. The increased mutation rate results in decreased viability of progeny cells, leading to death of the cancer cells, or a diminished growth rate, or inability to metastasize. In another embodiment, mutations are incorporated into transcription products, e.g., mRNA molecules that encode proteins or tRNA molecules useful for translation of proteins. The mutated transcription products encode mutated proteins, for example, proteins with altered amino acid sequences or truncations that lead, in turn to the inactivation of the protein. The inability of the cancer cell to consistently encode active protein can also result in death of the cancer cells, or a diminished growth rate, or inability to metastasize, or inability to proliferate.

Assays for Mutagenic Nucleosides and Nucleotides

In one embodiment, preferred nucleoside analogs of the present invention include 5-aza-cytidine, 5-aza-2'-deoxycytidine, and derivatives and variants thereof including nucleotides, which can be incorporated and extended by a polymerase. Generally, such analogs have phosphodiester linkages allowing them to be extended by the polymerase molecule after their incorporation into RNA or DNA. Thus, unlike certain viral inhibitors which cause chain termination (e.g., analogs lacking a 3'-hydroxyl group), the preferred analogs of the present invention are non-chain-terminating analogs that generally do not result in the termination of RNA or DNA synthesis upon their incorporation. Instead, they are preferably error-inducing analogs, which can be incorporated into an DNA or RNA product but which effectively alter the base-pairing properties at the position of their incorporation, thereby causing the introduction of errors in the RNA or DNA sequence at the site of incorporation.

Determination of parameters concerning the incorporation of altered nucleotides by a polymerase such as, human RNA polymerase II and viral polymerases/replicates or the phosphorylation of nucleoside analogs by cellular kinase, is made by methods analogous to those used for incorporation of deoxynucleoside triphosphates by DNA polymerases (Boosalis, et al., *J. Biol. Chem.* 262: 14689-14698 (1987). Those of skill in the art will recognize that such assays can also be used to determine the ability of a compound to inhibit a cellular polymerase or to determine the replicative capability of a virus that has been treated with an altered nucleotide. In selected situations direct determination of the frequency of mutations that are introduced into the viral genome (Ji and Loeb, *Virol.*, 199: 323-330 (1994) can be made.

The nucleoside or nucleotide analog is incorporated by a cellular polymerase or viral polymerase into the DNA or RNA copy of the genomic nucleic acid with an efficiency of at least about 0.1%, preferably at least about 5%, and most preferably equal to that of a naturally occurring complementary nucleic acid when compared in equal amounts in an in vitro assay. Thus, an error rate of about 1 in 1000 bases or more would be sufficient to enhance mutagenesis of the virus. The ability of the nucleoside or nucleotide analog to cause incorrect base pairing may be determined by testing and examining the frequency and nature of mutations produced by the incorporation of an analog into DNA or RNA. It has been reported, for example, that the mutation rates in lytic RNA viruses (such as influenza A) are higher than in DNA viruses, at about 300-fold times higher, Drake, *PNAS, USA* 90: 4171-4175 (1993). Retroviruses, however, apparently normally mutate at an average rate about an order of magnitude lower than lytic RNA viruses. Id.

For example, in the case of HIV, the viral RNA or the incorporated HIV DNA is copied by reverse transcriptase and then DNA polymerase using a PCR reaction with complementary primers and all four deoxynucleoside triphosphates. The region of the genome copied corresponds to a 600 nucleotide segment in the reverse transcriptase gene. The copied DNA or RNA after 70 rounds of PCR is treated with restriction enzymes that cleave the primer sequences, and ligated into a plasmid. After transfection of *E. coli*, individual clones are obtained and the amplified segment within the plasmid is sequenced. Mutations within this region are determined by computer-aided analysis, comparing the individual sequences with control viral sequences obtained by parallel culturing of the same virus in the absence of the RNA analog. For each nucleotide, determinations are carried out after ten sequential rounds of viral passage or at the point of extinction for viral detection. Analogous procedures would be effective for other viruses of interest and would be readily apparent to those of skill in the art.

Incorporation of an analog by a cellular or viral RNA polymerase, by reverse transcriptase (or other viral enzyme) or by DNA polymerase may be compared directly, or separately and the separate test results subsequently compared. A comparison of incorporation of analogs among the polymerases of interest can be carried out using a modification of the "minus" sequencing gel assay for nucleotide incorporation. A 5'-$^{32}$P-labeled primer is extended in a reaction containing three of the four nucleoside triphosphates and an analog in the triphosphate form. The template can be either RNA or DNA, as appropriate. Elongation of the primer past the template nucleotide that is complementary to the nucleotide that is omitted from the reaction will depend and be proportional to the incorporation of the analog. The amount of incorporation of the analog is calculated as a function of the percent of oligonucleotide that is extended on the sequencing gel from one position to the next. Incorporation is determined by autoradiography followed by either densitometry or cutting out each of the bands and counting radioactivity by liquid scintillation spectroscopy. Those of skill in the art will recognize that similar experiments can be done to determine the incorporation of the compounds of the present invention into nucleic acids of cancer cells.

When a nucleoside or nucleotide analog of the invention is administered to virally infected cells, either in vitro or in vivo, a population of cells is produced comprising a highly variable population of replicated homologous viral nucleic acids. This population of highly variable cells results from administering mutagenic nucleoside or nucleotide analogs to virally infected cells and increasing the mutation rate of the virus population. Thus, the highly variable population of viruses is an indicator that the mutation rate of the virus was increased by the administration of the nucleoside or nucleotide analogs. Measuring the variability of the population provides an assessment of the viability of the viral population. In turn, the viability of the viral population is a prognostic indicator for the health of the cell population. For example, low viability for an HIV population in a human patient corresponds to an improved outlook for the patient.

In some embodiments, the mutagenic nucleoside or nucleotide analog of choice will be water-soluble and have the ability to rapidly enter the target cells. Lipid soluble analogs are also encompassed by the present invention. The nucleoside or nucleotide analog will be phosphorylated by cellular kinases, if necessary, and incorporated into RNA or DNA.

Assays of Viral Replication

Those of skill in the art recognize that viral replication or infectivity correlates with the ability of a virus to cause disease. That is, a highly infectious virus is more likely to cause disease than a less infectious virus. In a preferred embodiment, a virus that has incorporated mutations into its genome as a result of treatment with the compounds of this invention will have diminished viral infectivity compared to untreated virus. Those of skill in the art are aware of methods to assay the infectivity of a virus. (See, e.g., Condit, *Principles of Virology*, in *Fields Virology*, 4th Ed. 19-51 (Knipe et al., eds., 2001)).

For example, a plaque-forming assay can be used to measure the infectivity of a virus. Briefly, a sample of virus is diluted into appropriate medium and serial dilutions are plated onto confluent monolayers of cells. The infected cells are overlaid with a semisolid medium so that each plaque develops from a single viral infection. After incubation, the plates are stained with an appropriate dye so that plaques can be visualized and counted.

Some viruses do not kill cells, but rather transform them. The transformation phenotype can be detected, for example formation of foci after loss of contact inhibition. The virus is serially diluted and plated onto monolayers of contact inhibited cells. Foci can be detected with appropriate dye and counted to determine the infectivity of the virus.

Another method to determine infectivity of viruses is the endpoint method. The method is appropriate for viruses that do not form plaques or foci, but that do have a detectable pathology or cytopathic effect (CPE) in cultured cells, embryonated eggs, or animals. A number of phenotypes are measurable as CPE, including rounding, shrinkage, increased refractility, fusion, syncytia formation, aggregation, loss of adherence or lysis. Serial dilutions of virus are applied to an appropriate assay system and after incubation, CPE is assayed. Statistical methods are available to determine the precise dilution of virus required for infection of 50% of the cells. (See, e.g., Spearman, *Br. J. Psychol.* 2:227-242 (1908); and Reed and Muench, *Am. J. Hyg.* 27:493-497 (1938)).

The ability of a drug to inhibit viral replication or infectivity is expressed as the $EC_{50}$ of the drug, or the effective concentration that prevents 50% of viral replication. Methods described above to determine the infectivity of a virus are useful to determine the $EC_{50}$ of a drug.

The ability of a drug to kill cells is expressed as the $IC_{50}$, or the concentration of drug that inhibit cellular proliferation. Methods to determine the $IC_{50}$ of a drug are known to those of skill in the art and include determination of cell viability after incubation with a range of concentrations of the drug.

Treatment of HIV Strains Resistant to Nucleoside Reverse Transcriptase Inhibitors The compounds of the invention can be used to treat HIV infections and other retroviral infections. The compounds of the present invention are particularly well suited to treat HIV strains that are resistant to nucleoside reverse transcriptase inhibitors.

As of 2001, sixteen antiviral drugs were approved for the treatment of HIV infection. Seven are nucleoside/nucleotide analog chain terminators or nucleoside reverse trascriptase inhibitors (NRTI), six are protease inhibitors, and three are non-nucleoside reverse transcriptase inhibitors (NNRTI).

Until recently, zidovudine was the mainstay of anti HIV drugs. The administration of zidovudine to patients with advanced HIV disease has been shown to prolong survival, to improve neurologic function, to transiently improve CD4+ lymphocyte counts, and to decrease the rate of antigenemia. However, the short-term benefits observed with zidovudine monotherapy, together with the emergence of zidovudine resistance during chronic treatment suggested that combination chemotherapy would be required for prolonged control of HIV infection (see e.g., Loveday et al., *Lancet.* 345: 820-824 (1995); Volberding, et al., *J. Infect. Dis.* 171: S150-S154. (1995)).

In 1996, clinical trial results demonstrated that protease inhibitors could dramatically reduce the amount of HIV in a patient's blood and in combination therapy regimens could, in some cases, result in undetectable viral RNA by PCR. A combination chemotherapy clinical trial of saquinavir, zidovudine and zalcitabine demonstrated increased CD4+ counts and decreased viral burden that were significantly greater than a two drug regimen (see, e.g., Collier et al., *New Engl. J. Med.* 334: 1011-1017 (1996)). However, as with nucleoside analogs, there is evidence that cross-resistance develops to protease inhibitors (see e.g., Condra et al., *Nature* 374: 569-571 (1995)). In fact, simultaneous mutations of the HIV genome coding for resistance to protease inhibitors and NRTI have been described (Shafer et al., *Ann. Intern. Med.* 128: 906-911 (1998)). Of note, combination therapy regimens (highly active antiretroviral therapy or HAART), typically initiated with triple drug therapy, are expensive and because of their complexity and side effects adversely affect the patients' quality of life. Full therapeutic benefit may require near perfect adherence to the dosage, frequency, timing and dietary restrictions of many agents (see, e.g., Stone *Clin. Infect. Dis.* 33: 865-872 (2001)). Furthermore, if virologic, immunologic or clinical failure develops during triple therapy a regimen of five or more drugs may be necessary, so called mega-HAART (BHIVA Writing Committee. *HIV Med.* 1: 76-101 (2000)).

Thus, novel HIV therapeutics with a low likelihood of viral resistance are required in the marketplace. One embodiment of this invention describes a novel class of nucleoside and nucleotide analogs for activity against a panel of HIV strains resistant to conventional NRTI.

Routine screening of candidate 5-aza-dC formulations and derivatives was performed against HIV LAI. Candidates with high activity against HIV LAI were also screened for activity against strains of HIV with preexisting resistance to nucleoside reverse transcriptase inhibitors (NRTI).

HIV strains resistant to NRTI are known and mutations in the reverse transcriptase (RT) enzyme responsible for the resistance have been analyzed. Resistance mutations in HIV RT appear to only increase the pre-existing capabilities of wild type RT rather than creating new ones. Two mechanisms of resistance toward NRTI have been described: an increase in efficiency of discrimination between an NRTI and a naturally occurring nucleoside, and excision of an NRTI by pyrophosphorolysis in the presence of nucleotides (see, e.g., Isel et al., *J. Biol. Chem.* 276: 48725-48732 (2001)). Decrease in affinity of HIV RT for a NRTI usually involves alterations in the sugar moiety of an analog, e.g., mutations M184V or Q151M (see, e.g., Sluis-Cremer et al., *Cell. Mol. Life Sci.* 57: 1408-1422 (2000)). Alternatively, chain terminators may be removed by pyrophosphorolysis, or reverse nucleotide polymerization, where pyrophosphate acts as acceptor molecule for the removal of the chain terminator. Removal of the chain-terminator frees RT to incorporate the natural nucleotide substrate and rescue viral replication. ATP has also been proposed as an acceptor molecule for the removal of chain-terminators and is referred to as primer unblocking (see, e.g., Naeger et al., *Nucleosides Nucleotides Nucleic Acids* 20: 635-639 (2001)).

Viral resistance is less likely to emerge after treatment with mutagenic nucleotide analogues than after treatment with NRTI. For example, mutagenic nucleotide analogues apply less selective pressure to a viral population for emergence of resistant variants than approved antivirals, which attempt to immediately halt viral replication. Mutagenic nucleotide analogues adversely affect all viral proteins. Decreased affinity of HIV RT for a modified nucleoside sugar is one mechanism of viral resistance. Mutagenic nucleotide analogues have unmodified sugars. For example, it has been shown that RT may recognize the absence of a 3'-OH group, resulting in cross-resistance among chain terminators (see, e.g., Huang et al., *Science* 282: 1669-75 (1998)). Mutagenic nucleotide analogues, like natural ds, have a 3'-OH. Because mutagenic nucleotide analogues do not terminate replication, pyrophosphorolysis, the other principal mechanism of viral resistance to conventional nucleoside analogs, is unlikely to be applicable to MDRN. Pyrophosphorolysis by RT results in the excision of a chain terminator preventing DNA chain elongation.

Cross resistance between NRTI and mutagenic nucleoside or nucleotide analogues can be tested by determining the $EC_{50}$ for a mutagenic nucleoside or nucleotide analogue in a wild-type HIV strain and in an HIV strain resistant to one or more NRTI's. If the $EC_{50}$ for the mutagenic nucleoside or nucleotide analogue is higher in the NRTI resistant strain than in the wild-type strain, it suggests that cross-resistance has occurred. Experiments have demonstrated that cross-resistance is unlikely to develop between NRTI and mutagenic nucleoside or nucleotide analogues. A panel of three HIV NRTI resistant strains (AIDS Research and Reference Reagent Program, Division of AIDS, NIAID, NIH), where resistance is achieved by pyrophosphorolysis or enhanced RT discrimination, were used to test the effectiveness of 5-aza-2'-deoxycytidine (5-aza-dC), a mutagenic nucleoside or nucleotide analogue. These strains have most of the mutations in susceptibility to NRTI present in routine clinical samples (see, e.g., Hertogs, Antiviral Drug Discovery and Development Summit. Strategic Research Institute, NY, N.Y. (2001)), namely: 1) HIV-1 LA1-M184V: The M184V mutation confers resistance to lamivudine (3TC). M184V also decreases the likelihood of incorporation of 3TC-TP by interaction with the sulfur of the oxathiolane ring but interestingly also enhances sensitivity to zidovudine perhaps by reducing pyrophosphorolytic activity (see e.g., Boyer et al., *J. Virol.* 76: 3248-3256 (2002)). 2) HIV-1 RTMDR1, with 74V, 41L, 106A and 215Y mutations. RTMDR1 is resistant to zidovudine, didanosine, nevirapine and other non-nucleoside reverse transcriptase inhibitors. Template/primer repositioning may play a role in the decreased DNA synthesis processivity associated with the 74V mutation for didanosine. Resistance mutations 41L and 215Y enhance pyrophosphorolysis (see, e.g., Sluis-Cremer et al., supra). 3) HIV-1 RTMC, with 67N, 70R, 215F and 219Q mutations. RTMC is resistant to zidovudine. All of these mutations enhance pyrophosphorolysis (Id.). The $EC_{50}$ of 5-aza-dC for the wild-type HIV strain LAI was similar to the $EC_{50}$ of 5-aza-dC for NRTI resistant strains. In contrast, the $EC_{50}$ of AZT or 3TC for the wild-type HIV strain LAI was markedly different than the $EC_{50}$ of AZT or 3TC for the appropriate NRTI resistant strain (e.g., RTMC, M184V, or RTMDR1). Other NRTI mutants are available and can be assayed in a similar manner (Gonzales et al., Program and Abstracts of the Forty-Second Interscience Conference on Antimicrobials and Chemotherapy. Abstract No. 3300 (2002)). Mutations include: M41L, E44D, A62V, K65R, D67N, T69DN, T69S_SS, K70R, L74V, V75I, F77L, Y115F, F116Y, V118I, Q151M, M184V, L210W, T215F and K219QE.

Treatment of Cancer

The compounds of the present invention can be used to treat cancer. Because malignant cells replicate more rapidly than nonmalignant cells, the compounds of the invention are preferentially incorporated into malignant cells. In a preferred embodiment, leukemias and other hematopoetic cancers are treated using the compounds of the present invention. Without wishing to be bound by theory, the nucleoside and nucleotide analogues of the present invention are incorporated into the nucleic acids of a cancerous cell, either DNA or RNA. The nucleoside and nucleotide analogues have phosphodiester linkages or obtain phosphodiester linkages, allowing them to be incorporated and extended by a polymerase. In one embodiment, the nucleoside and nucleotide analogues have altered base-pairing properties allowing incorporation of mutations into the genome of the cancer cell, dramatically increasing the mutation rate in the cancer cell. The increased mutation rate results in decreased viability of progeny cells, leading to death of the cancer cells, or a diminished growth rate, or inability to metastasize. In another embodiment, mutations are incorporated into transcription products, e.g., mRNA molecules that encode proteins or tRNA molecules useful for translation of proteins. The mutated transcription products encode mutated proteins, for example, proteins with altered amino acid sequences or transactions that lead, in turn to the inactivation of the protein. The inability of the cancer cell to consistently encode active protein can also result in death of the cancer cells, a diminished growth rate, inability to metastasize, or inability to proliferate.

Those of skill in the art are aware of methods to test the effectiveness of compounds in treating cancer. For example, cancer cells of interest can be grown in culture and incubated in the presence varying concentrations of the compounds of the present invention. Frequently, uptake of vital dyes, such as MTT, is used to determine cell viability and cell proliferation. When inhibition of cell proliferation is seen, the $IC_{50}$ of the compound can be determined, essentially as described above. Those of skill in the art will also know to test the compounds of the present invention in animal models, for example, nude mice injected with transformed cells. The data gathered in tissue culture models and animal models can be extrapolated by those of skill in the art for use in human patients.

Combination Therapies

The compounds of the invention can also be used in combination with other drugs to treat viral diseases or cancers.

For example, mutagenic nucleoside analogs can be used in combination with other antiviral therapies, such as nucleoside reverse transcriptase inhibitors, (e.g., Zidovudine (ZDV or AZT), Didanosine (ddI), Zalcitabine (ddC), Stavudine (d4T), Lamivudine (3TC), Abacavir (ABC), and Tenofovir tenofovir disoproxil fumarate (TDF)), non-nucleoside reverse transcriptase inhibitors, (e.g., Nevirapine (NVP), Delavirdine (DLV), and Efavirenz (EFV)), protease inhibitors, (e.g., Invirase, Fortovase, Norvir, Crixivan, Viracept, Agenerase, Kaletra, Reyataz, fosamprenavir, and tipranavir) integrase inhibitors, fusion inhibitors or immunomodulators, such as interferon. Drugs that induce viral replication, such as diacylglycerol analogues, (e.g., Hamer et al. *Journal of Virology.* 77:10227-10236 (2003)), might also benefit from combination with a viral mutagen. These drugs may have utility in decreasing the size of the viral reservoir. Mutagenic nucleoside analogues can also be used in combination with cytokines such as IL-2. (See, e.g., Kedzierski and Crowe, *Antiviral Chem. & Chemo.* 12:133-150 (2001)). Combination of such compounds with a viral mutagen, would allow incorporation of mutagenic nucleosides into the viral genome producing less fit viruses and ultimately resulting in viral extinction.

For cancer treatment mutagenic nucleoside analogs can be used in combination with other anticancer therapies, e.g. radiation, chemotherapeutic agents, hormone analogues, immunostimulants, interferons, cytokines, and antibodies.

Administration

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compounds (in the form of their compositions) are administered to patients by the usual means known in the art, for example, orally or by injection, infusion, infiltration, irrigation, and the like. For administration by injection and/or infiltration or infusion, the compositions or formulations according to the invention may be suspended or dissolved as known in the art in a vehicle suitable for injection and/or infiltration or infusion. Such vehicles include isotonic saline, buffered or unbuffered and the like. Depending on the intended use, they also may contain other ingredients, including other active ingredients, such as isotonicity agents, sodium chloride, pH modifiers, colorants, preservatives, antibodies, enzymes, antibiotics, antifungals, antivirals, other anti-infective agents, and/or diagnostic aids such as radioopaque dyes, radiolabeled agents, and the like, as known in the art. However, the compositions of this invention may comprise a simple solution or suspension of a compound or a pharmaceutically acceptable salt of a compound, in distilled water or saline.

Alternatively, the therapeutic compounds may be delivered by other means such as intranasally, by inhalation, or in the form of liposomes, nanocapsules, vesicles, and the like. Compositions for intranasal administration usually take the form of drops, sprays containing liquid forms (solutions, suspensions, emulsions, liposomes, etc.) of the active compounds. Administration by inhalation generally involves formation of vapors, mists, dry powders or aerosols, and again may include solutions, suspensions, emulsions and the like containing the active therapeutic agents Routes and frequency of administration of the therapeutic compositions described herein, as well as dosage, will vary from individual to individual, and may be readily established using standard techniques. Preferably, between 1 and 100 doses may be administered over a 52-week period. When treating a viral disease, a suitable dose is an amount of a compound that, when administered as described above, is capable of killing or limiting the infectivity of a virus. When treating cancer, a suitable dose is an amount of a compound that, when administered as described above, is capable of killing or slowing the growth of, cancers or cancer cells.

In general, an appropriate dosage and treatment regimen provides the active compound(s) in an amount sufficient to provide therapeutic and/or prophylactic benefit. A response can be monitored by establishing an improved clinical outcome (e.g., longer viral disease-free survival or in cancer patients, more frequent remissions, complete or partial, or longer disease-free survival) in treated patients as compared to non-treated patients.

A therapeutic amount of a compound described in this application, means an amount effective to yield the desired therapeutic response, for example, an amount effective to kill or limit the infectivity of a virus, when treating a viral disease. When treating a patient with cancer, a therapeutic amount of a compound described in this application is for example, an amount effective to delay or halt the growth of a cancer or to cause a cancer to shrink or not metastasize. For treatment of both viral diseases and cancer, if what is administered is not the compound (or compounds), but an enantiomer, prodrug, salt or metabolite of the compound (or compounds), then the term "therapeutically effective amount" means an amount of such material that produces in the patient the same blood concentration of the compound in question that is produced by the administration of a therapeutically effective amount of the compound itself. Similarly, if an enantiomer, prodrug or metabolite of the compositions, or a salt of the compositions or of any of these other compounds, is being administered, then one therapeutically effective amount of such a compound is that amount that produces a therapeutically relevant blood concentration of the compositions in a patient. Oral dosages optimally range from 500 mg to 2 grams for treatment of viral diseases or cancer. Those of skill in the art are aware of the routine experimentation that will produce an appropriate dosage range for a patient in need of treatment by oral administration or any other method of administration of a drug, e.g., intravenous administration or parenteral administration, for example. Those of skill are also aware that results provided by in vitro or in vivo experimental models can be used to extrapolate approximate dosages for a patient in need of treatment.

Patients that can be treated with the a compound described in this application, and the pharmaceutically acceptable salts, prodrugs, enantiomers and metabolites of such compounds, according to the methods of this invention include, for example, patients that have been diagnosed as having HIV infection, hepatitis B, hepatitis C, or small pox or vaccinia virus.

Other patients that can be treated with the a compound described in this application, and the pharmaceutically acceptable salts, prodrugs, enantiomers and metabolites of such compounds, according to the methods of this invention include, for example, patients that have been diagnosed as having lung cancer, bone cancer, pancreatic cancer, skin cancer, cancer of the head and neck, cutaneous or intraocular melanoma, uterine cancer, ovarian cancer, rectal cancer or cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

In further aspects of the present invention, the compositions described herein may be used to treat hematological malignancies including adult and pediatric AML, CML, ALL, CLL, myelodysplastic syndromes (MDS), myeloproliferative syndromes (MPS), secondary leukemia, multiple myeloma, Hodgkin's lymphoma and Non-Hodgkin's lymphomas.

Within such methods, pharmaceutical compositions are typically administered to a patient. As used herein, a "patient" refers to any warm-blooded animal, preferably a human.

Kits for administering the compounds may be prepared containing a composition or formulation of the compound in question, or an enantiomer, prodrug, metabolite, or pharmaceutically acceptable salt of any of these, together with the customary items for administering the therapeutic ingredient.

All references and patent publications referred to herein are hereby incorporated by reference herein. As can be appreciated from the disclosure provided above, the present invention has a wide variety of applications. Accordingly, the following examples are offered for illustration purposes and are not intended to be construed as a limitation on the invention in any way.

EXAMPLES

Example 1

5-aza-dC is a Potent Mutagen of HIV 5-aza-2'-deoxycytidine (5-aza-dC) is a potent viral mutagen that is capable of eradicating HIV in a single passage.

Viral Stocks for Test of Antiviral Activity

The strains of HIV-1 used for primary drug screening are HIV-1 LAI or the appropriate strain of NRTI resistant HIV for studies of cross-resistance. Virus was propagated on MT-2 cells at an multiplicity of infection (MOI) of 0.01 to generate virus stocks. Briefly, the MT-2 cells were suspended in RPMI 1640 media supplemented with 10% fetal bovine serum, streptomycin and penicillin (cRPMI) and grown in a 37° C. incubator containing 5% $CO_2$. Serial dilution of the virus and infection of MT-2 cells were followed by an ELISA detecting the capsid protein of HIV-1 (p24) and used to determine the titer of the virus stocks (50% tissue culture infectious dose ($TCID_{50}$)). The ELISA was performed according to the manufacturer's instructions. The MT-2 cells are also used for visualizing the cytopathic effects of HIV-1 growth (e.g. syncytia formation).

Treatment of HIV-1-Infected Cells with Mutagenic Nucleoside or Nucleotide Analogues 0.1 ml of a $3\times10^5$ cells/ml MT-2 cell suspension were seeded in 96-well plates at $3\times10^4$ cells/well. The compounds to be assayed were diluted in a separate 96-well at ten times (10×) the concentration needed for the screen. 22 μl of the 10× compounds was then added to the wells in triplicate except for six control wells, containing uninfected MT-2 cells alone (3 wells) and untreated HIV-infected MT-2 cells (3 wells). This was followed by the addition of HIV-1 at an MOI of 0.01, except for the three wells serving as the uninfected control. 0.1 ml of cRPMI was added to the uninfected well instead of virus. After the addition of virus, the 96-well plate was centrifuged at 1,200×g for two hours to enhance the adsorption of the virus by the MT-2 cells (see, e.g., O'Doherty, J. Virol. 74:10074-10080 (2000)). After the centrifugation step, the 96-well plate was then incubated in a 37° C. incubator containing 5% CO2 for three days. At the end of this time period the virus and cells were mixed by gentle pipetting followed by a 1 minute spin at 600×g to pellet the cells. The supernatant of each well was then serially diluted 1,000-fold into new 96-well plates to serve as inoculum for the next passage and assayed by ELISA for the amount of p24 produced. The next passage was performed as described above, except that the virus used to infect the cells was derived from the 1,000-fold dilution plate. To generate an $EC_{50}$ value, half-log concentrations of mutagenic nucleoside or nucleotide analogue capable of eradicating virus in a single passage are tested as above to generate a dose-response curve.

Figure 4:
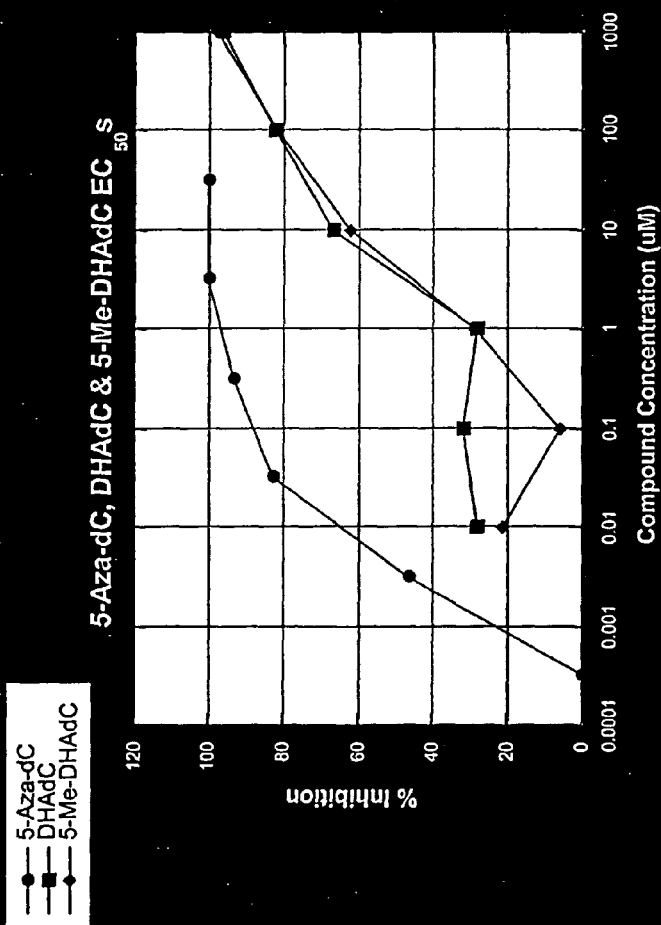
FIG. 4 depicts the $EC_{50}$ values for 5-Aza-dC, DHAdC and 5-Me-DHAdC against wild-type HIV virus. The experiments were carried out in MT-2 cells infected with HIV strain LAI.
Figure 5:
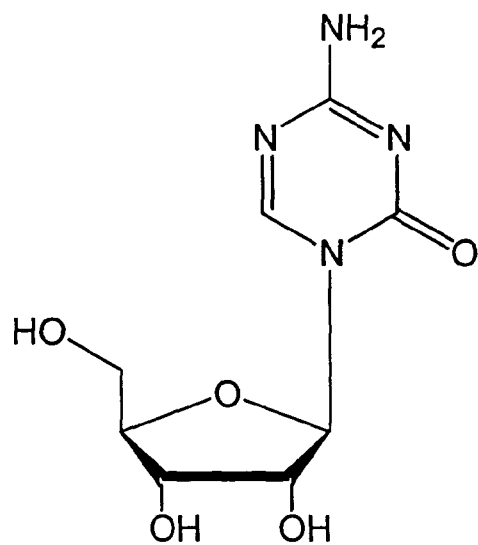
FIG. 5 is an illustration of compounds 1-4.
Figure 5:
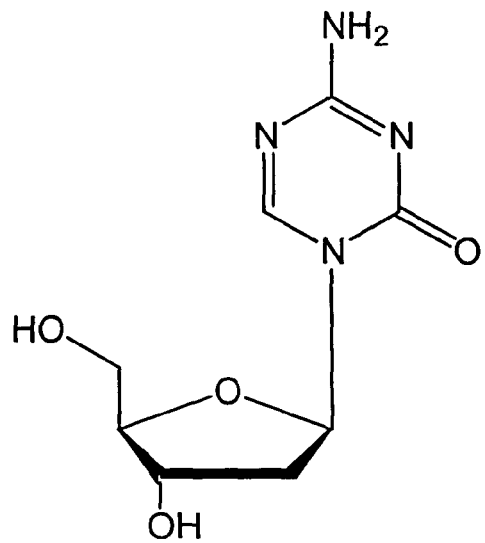
Figure 5:
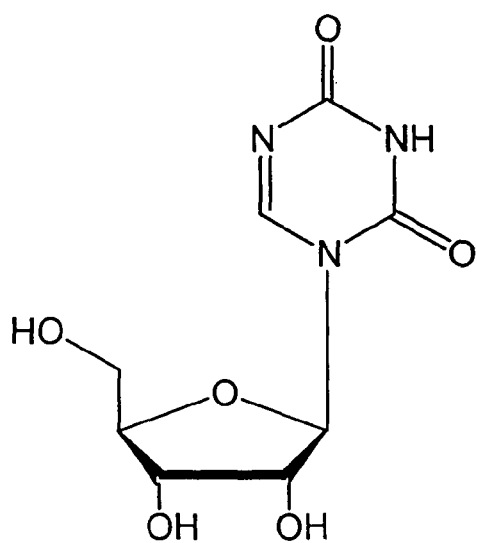
Figure 5:
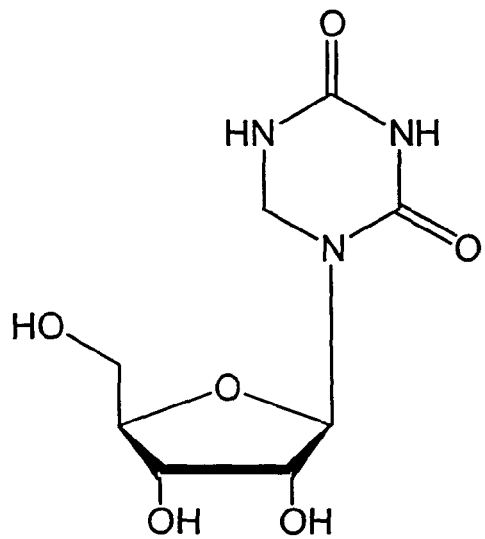
Figure 6:
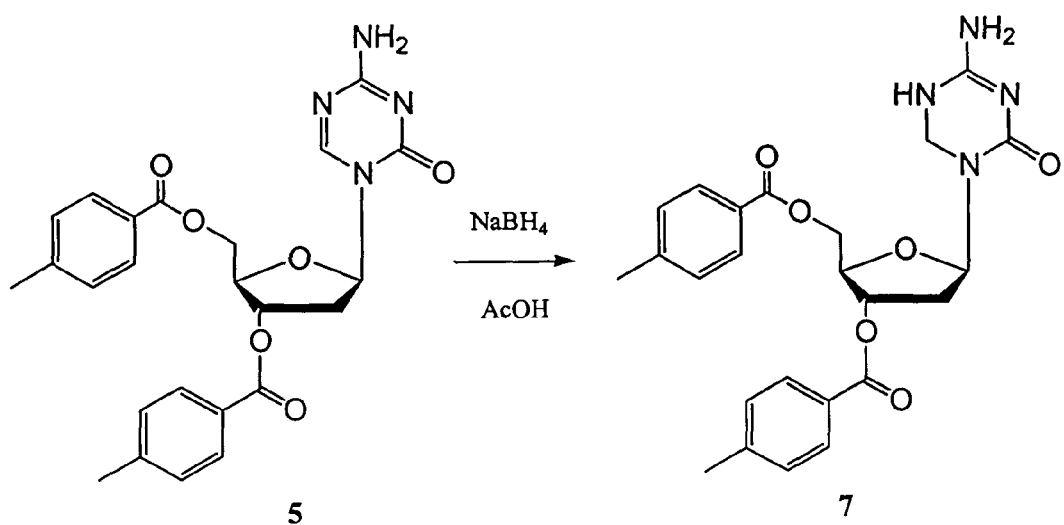
FIG. 6 is an exemplary synthetic scheme for compounds 7 and 8.
Figure 6:
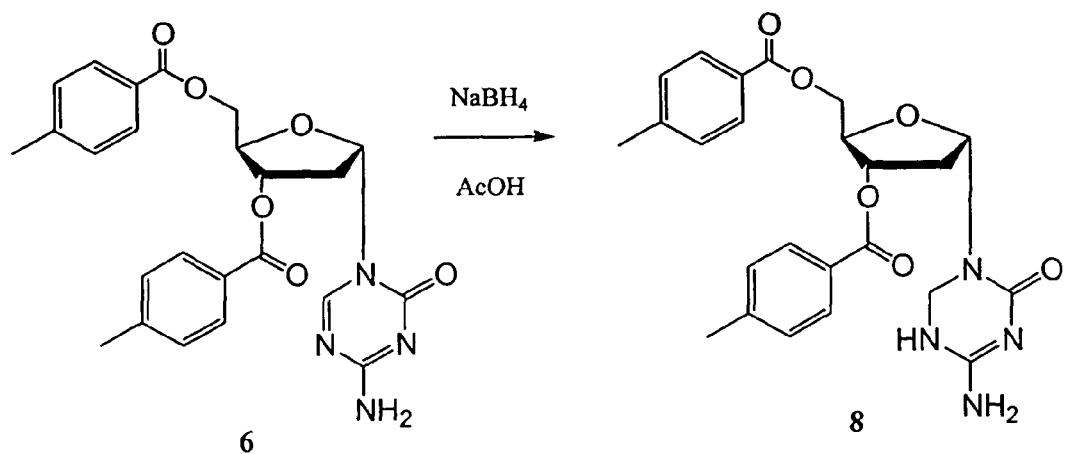
Figure 7:
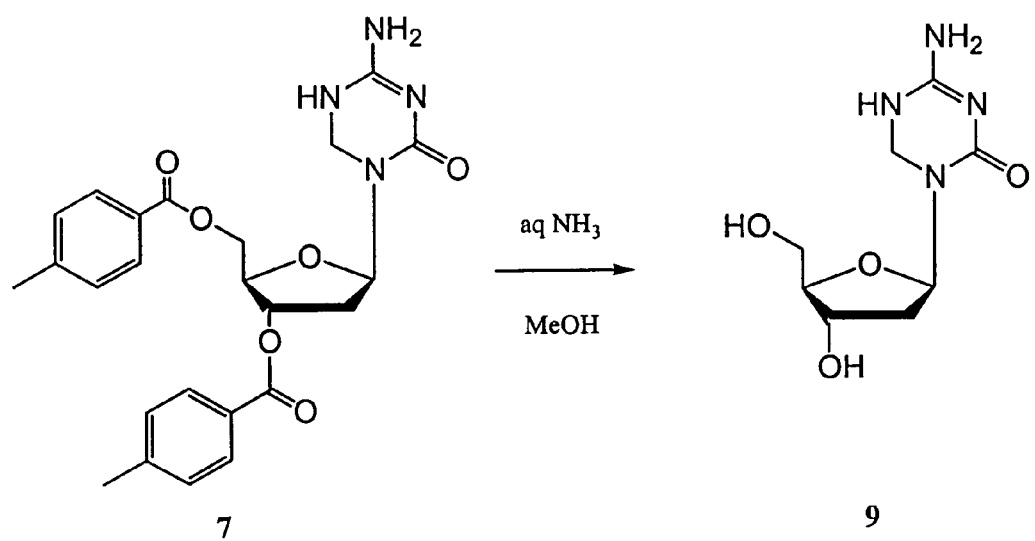
FIG. 7 is an exemplary synthetic scheme for compounds 9 and 10.
Figure 7:
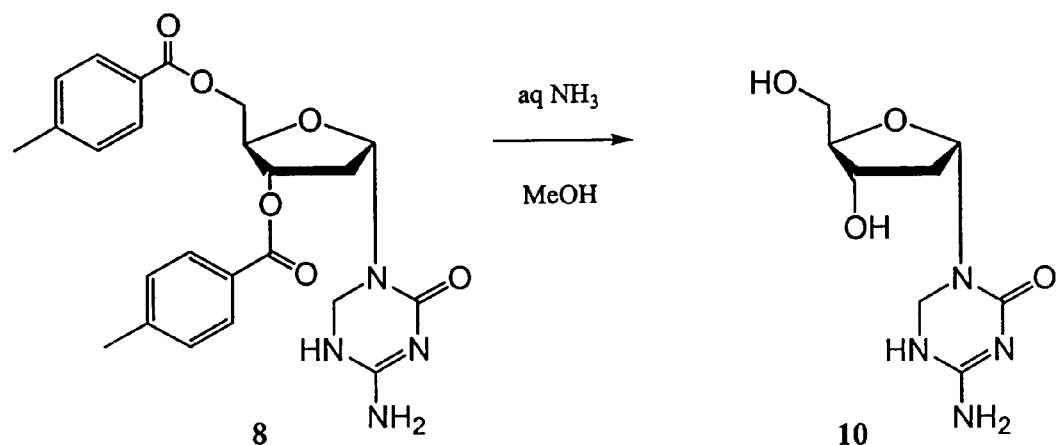
Figure 8:
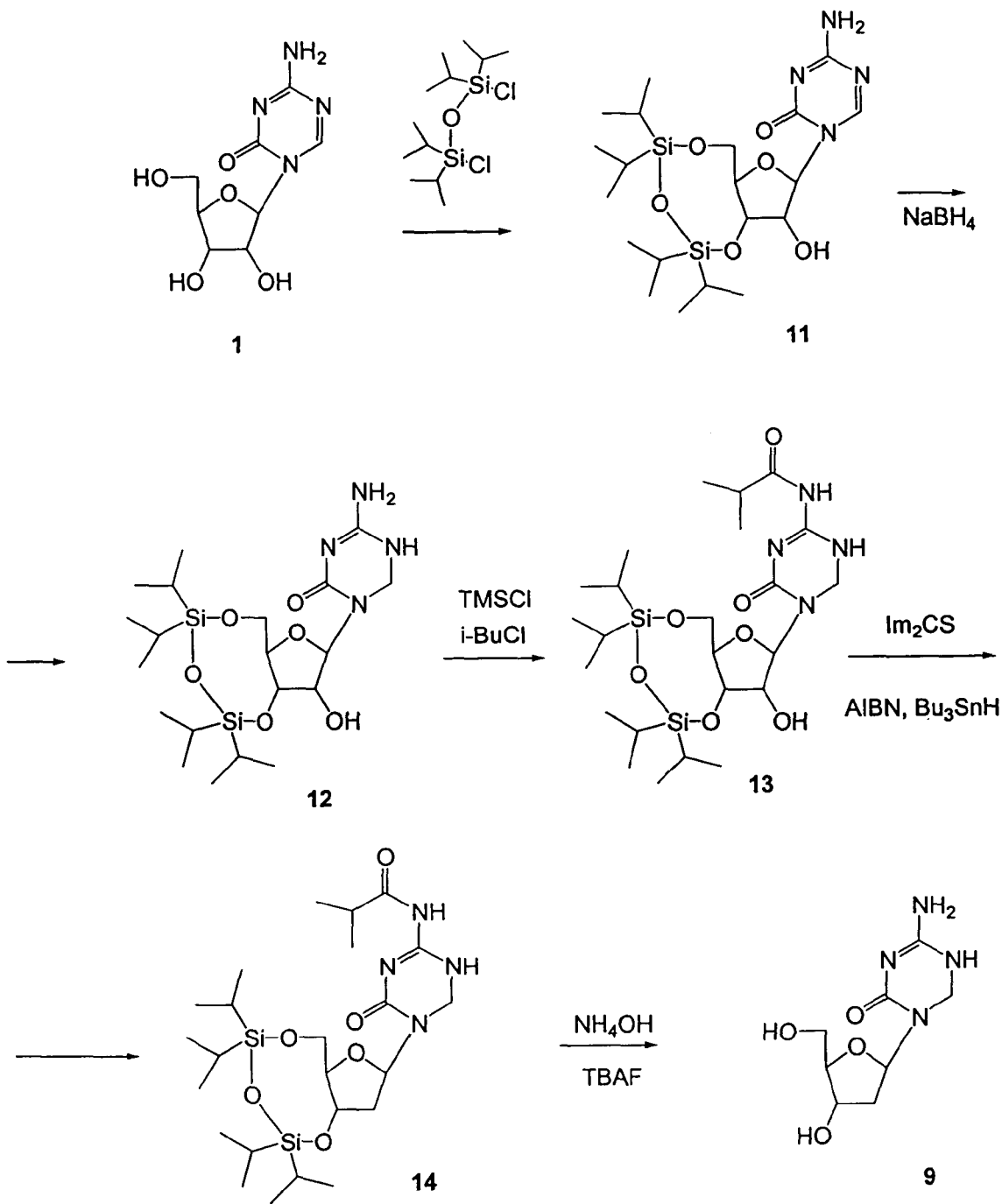
FIG. 8 is an exemplary synthetic scheme for compounds 9, and 11-14.
Figure 9:
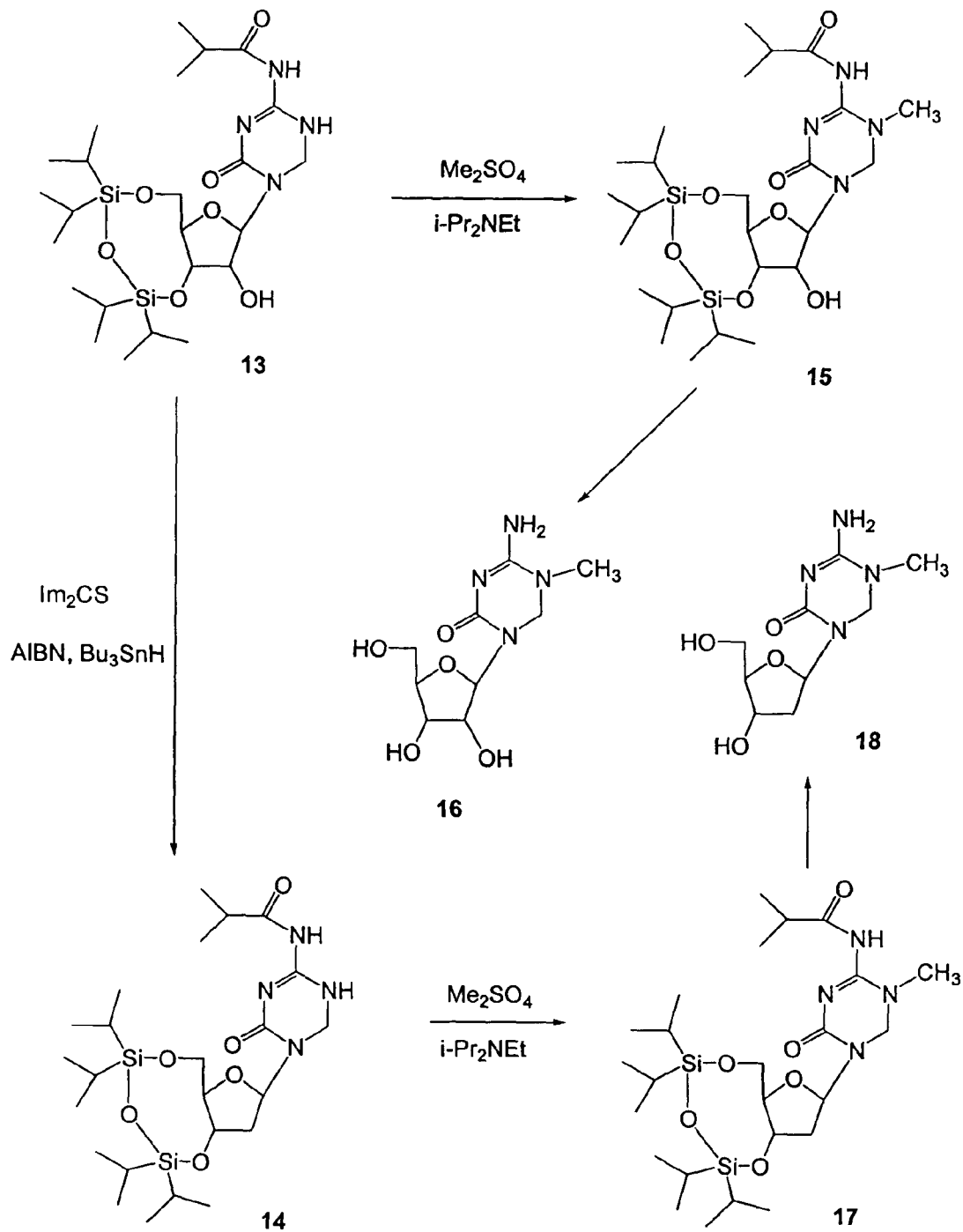
FIG. 9 is an exemplary synthetic scheme for compounds 14-18.
Figure 10:
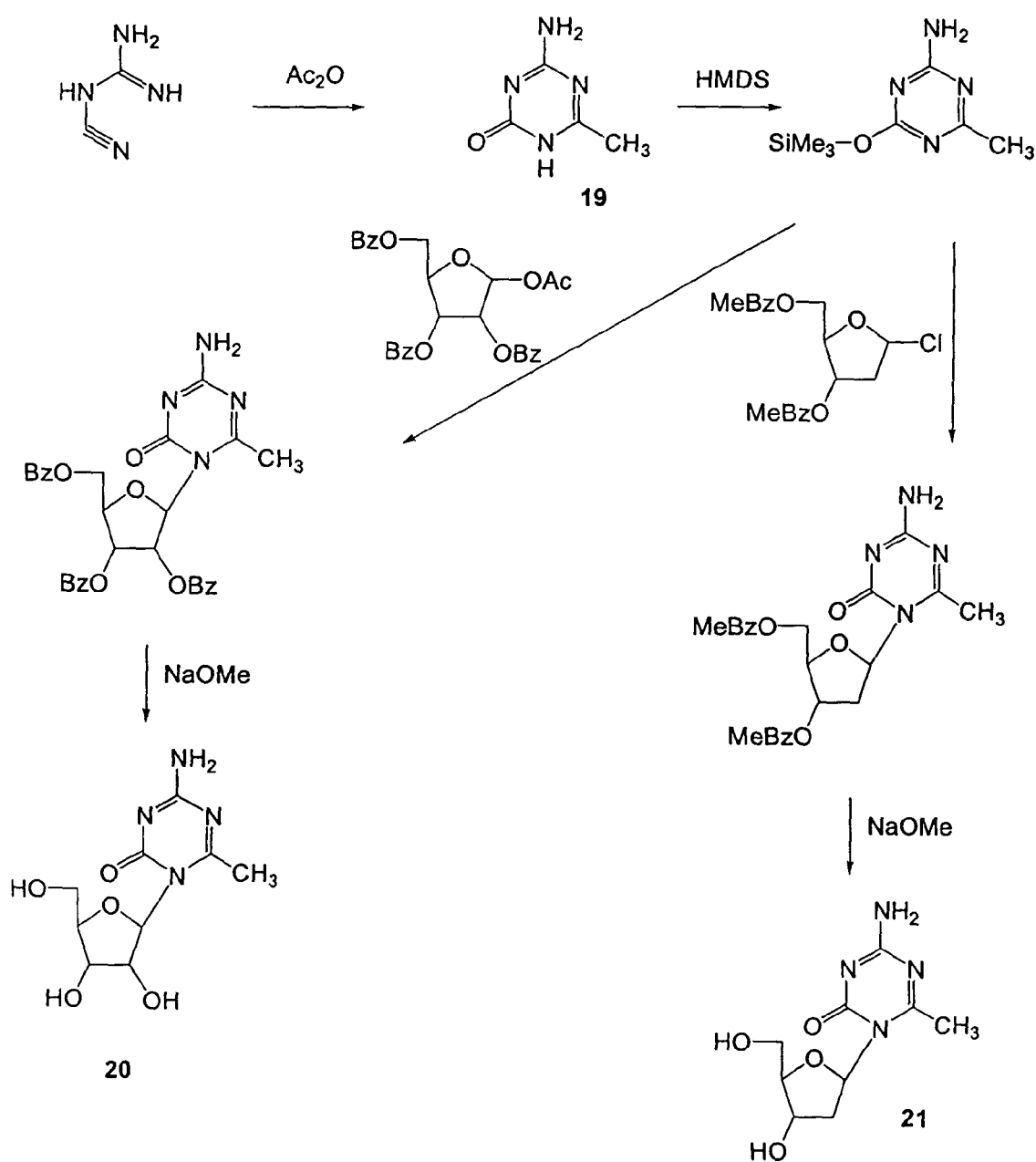
FIG. 10 is an exemplary synthetic scheme for compounds 20-21.
Figure 11:
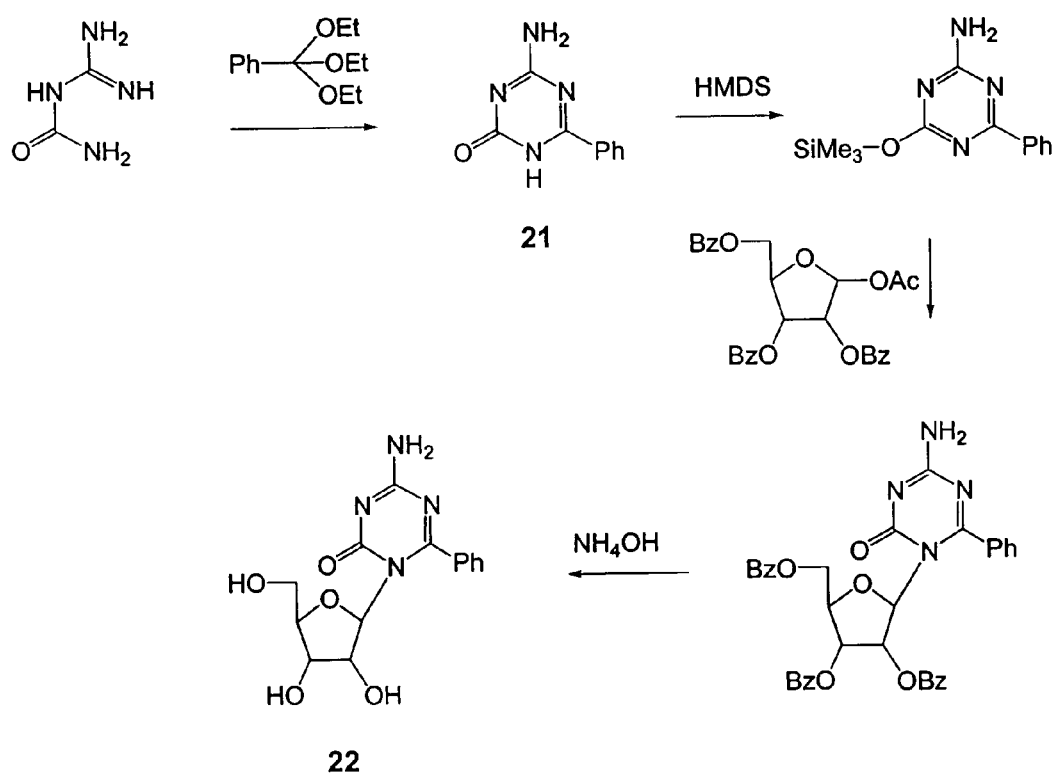
FIG. 11 is an exemplary synthetic scheme for compounds 20-21.
Figure 12:
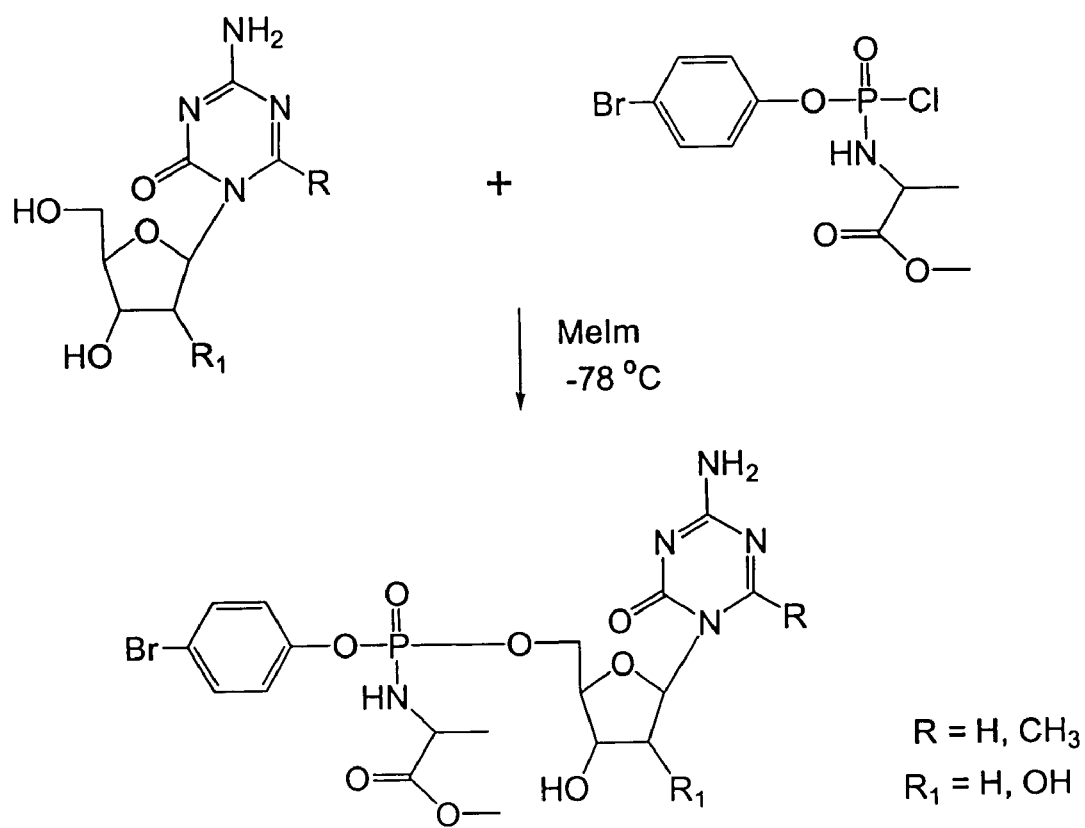
FIG. 12 is an exemplary synthetic scheme for a compound of the invention including a modified phosphodiester group.
Figure 13:
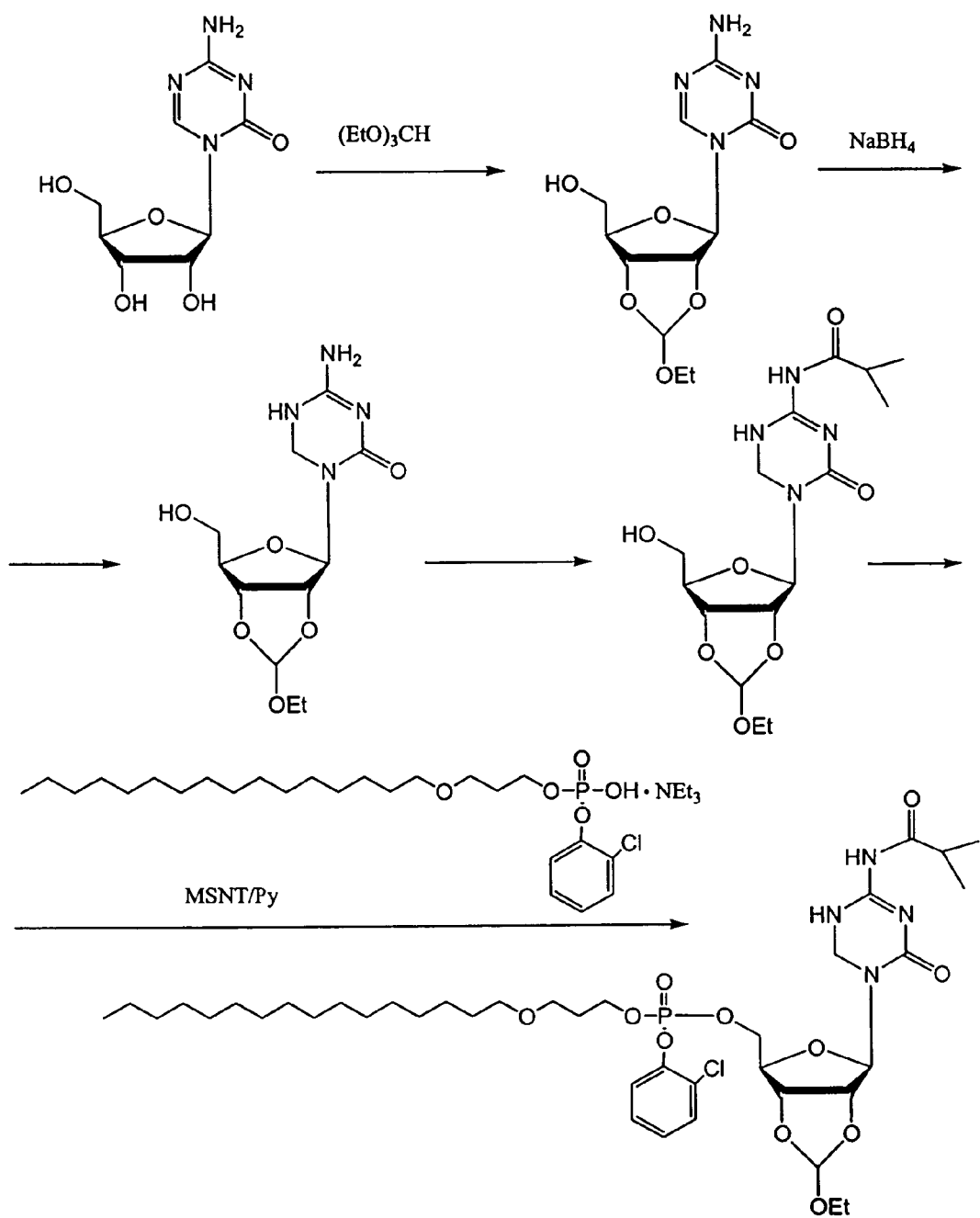
FIG. 13 is an exemplary synthetic scheme for a compound of the invention including a modified phosphodiester group derivatized with a hydrophobic moiety.
Figure 14:
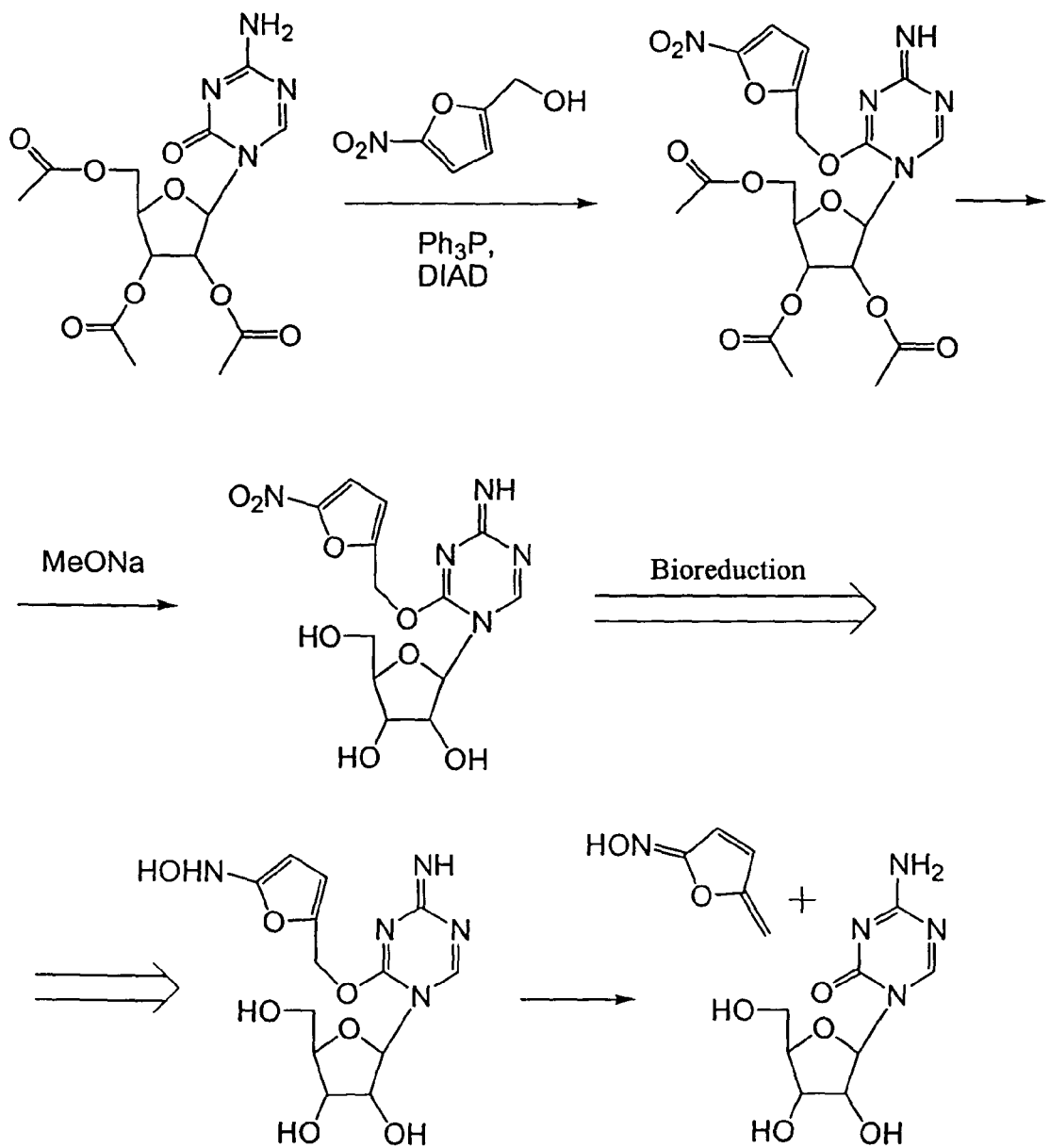
FIG. 14 is a retrosynthetic scheme for preparing a compound of the invention.
Figure 15:
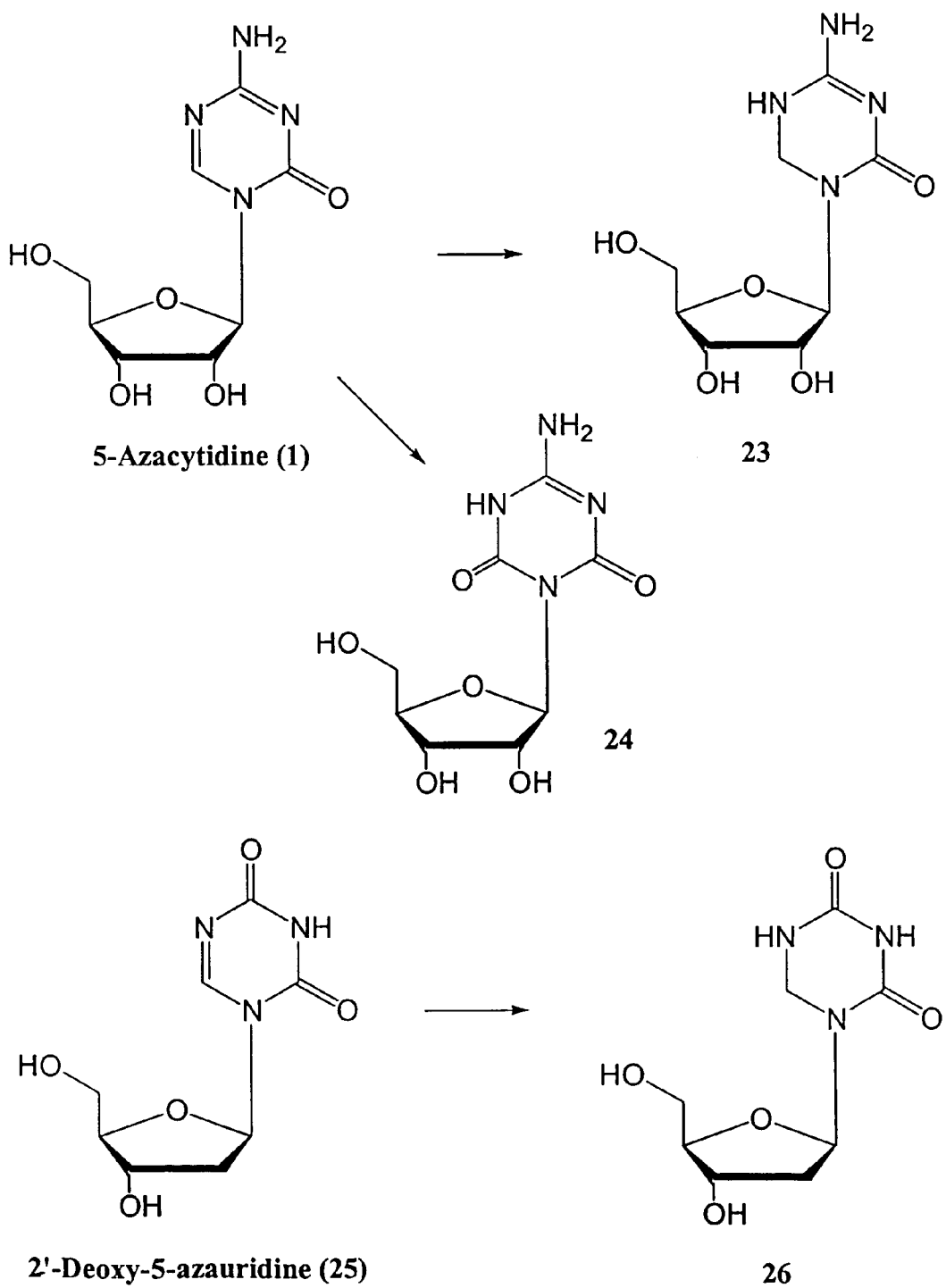
FIG. 15 is an exemplary synthetic scheme for compounds 23, 24 and 26.

$EC_{50}$ values were determined for the following compounds: 5-aza-dC, 5-aza-dU, DH-aza-dC, and 5-methyl-5,6-dihydro-5-azadeoxycytidine (MeDHAdC). 5-aza-dC has an $EC_{50}$ (effective concentration that prevents 50% of viral replication) of 3 nM against the wild-type HIV strain LAI. Results are shown in FIG. 4. The $EC_{50}$ values for the other compounds are 3 μM for DHAdC and 10 μM for MeDHAdC.

Assessment of the Frequency of Mutations to the Viral Genome Induced by Mutagenic Nucleoside Analogues The viral genomic DNA from cells treated with the deoxyribonucleoside analog 5-aza-dC (30 μM) was purified using a Qiagen DNeasy® Kit. 1 μg of genomic DNA was used to amplify a 1 kb region of the HIV-1 RT proviral DNA by PCR. The PCR product was then cloned into a TOPO® cloning vector. A Millipore Miniprep Kit was used to purify plasmid containing proviral inserts. About 45 positive clones were sequenced in both directions by a Beckman Coulter CEQ 8000. The sequencing results were analyzed and assembled using the DNASTAR Stagman program. Each mutated base was counted and the mutation rate was calculated over the total number of sequenced nucleotides. The results were compared with the background mutation rate generated from untreated control virus and are shown in Table 3. Sixty-one mutations were found in 26,187 bases sequenced in the 5-aza-dC treated cells. Only one mutation in the drug-free control could be confirmed by sequencing in both directions and thus, the mutation rate in the control may be overestimated. Thus, sequencing of a fragment of the nucleic acid encoding HIV reverse transcriptase has confirmed that 5-aza-dC is mutagenic to the viral genome.

TABLE 3

| ANALOG | MUTATIONS/ NUCLEOTIDE | % | GПA AПG | TПC CПT | AПT TПA | AПC CПA | GПT TПG | CПG GПC |
|---|---|---|---|---|---|---|---|---|
| 5-aza-dC | 61/ 26,187 | 0.223 | 24 | 6 | 8 | 0 | 10 | 13 |
| None | 6/ 11,023 | 0.054 | | | | 5 | | 1 |

Assessment of Mutagenic Nucleoside Analogue Cytotoxicity

For each compound, cytotoxicity was evaluated on MT-2 cells. MT-2 cells were seeded at $3\times10^4$ cells/well in 96-well plates. The cells were treated with compounds at half-log serial dilutions from 100 μM to 0.32 μM in triplicate. After 5 days growth in a 37° C. incubator containing 5% $CO_2$, MTT was added to a final concentration of 0.5 mg/ml and then incubated for four hours at 37° C. 10% SDS in 0.02 N HCl was added to lyse the cells overnight at 37° C. The plates were read on a Tecan Genius microplate reader at wavelengths of 570 nm/650 nm. The dose response curve was graphed by comparing the treated cells with the untreated control and the $IC_{50}$ was determined for each compound. For 5-aza-dC, the $IC_{50}$ was greater than 10 μM. For DHadC, the $IC_{50}$ was greater than 1 mM. The $IC_{50}$ for 5-Me-DHAdC was not determined.

Example 2

5-aza-dC is Effective Against Wild-Type HIV Strains and NRTI Resistant HIV Strains Assessment of Sensitivity of NRTI-Resistant HIV Strains to Mutagenic Nucleoside Analogue To determine if there is resistance of HIV NRTI resistant strains to mutagenic nucleoside analogues, NRTI resistant strains were grown in the presence of 5-aza-dC to determine whether the $EC_{50}$ for 5-aza-dC is different from the WT strain (HIV-1 LAI). An $EC_{50}$ higher for the NRTI-resistant strains than for the WT strain suggests that there is cross-resistance between 5-aza-dC and the particular NRTI. The $EC_{50}$ experiment was performed in a similar manner described above for the drug screen against HIV-LAI. Growth of HIV NRTI resistant strains in the presence of the appropriate concentration of NRTI was used as a positive control.

Three HIV NRTI resistant strains (HIV-1 LAI-M184V, HIV-1 RTMDR1, with 74V, 41L, 106A and 215Y mutations, and HIV-1 RTMC, with 67N, 70R, 215F and 219Q mutations) were used to test the effectiveness of 5-aza-dC. Results are shown in Table 4. These experiments demonstrate that HIV strains with resistance to NRTI are not cross-resistant with 5-aza-dC. The $EC_{50}$ of 5-aza-dC for the wild-type HIV strain LAI was similar to the $EC_{50}$ of 5-aza-dC for NRTI resistant strains. In contrast, the $EC_{50}$ of AZT or 3TC for the wild-type HIV strain LAI was markedly different than the $EC_{50}$ of AZT or 3TC for the appropriate NRTI resistant strain (e.g., RTMC, M184V, or RTMDR1). Other NRTI mutants are available and can be assayed in a similar manner (Gonzales et al., Program and Abstracts of the Forty-Second Interscience Conference on Antimicrobials and Chemotherapy. Abstract No. 3300 (2002)). Mutations include: M41L, E44D, A62V, K65R, D67N, T69DN, T69S_SS, K70R, L74V, V75I, F77L, Y115F, F116Y, V118I, Q151M, M184V, L210W, T215F and K219QE.

TABLE 4

| HIV Strain | 5-aza-dC ($EC_{50}$) nM | AZT ($EC_{50}$) nM | 3TC ($EC_{50}$) nM |
|---|---|---|---|
| LAI (wild type) | 3 | 10 | 45 |
| RTMC | 5 | 300 | 330 |
| M184V | 10 | 10 | >32,000 |
| RTMDR1 | 10 | 60 | N.D. |

Table 4: $EC_{50}$'s of 5-aza-dC versus zidovudine (AZT) and lamivudine (3TC) against wild type HIV LAI and drug resistant strains.

Example 3

5-aza-C is Effective Against Riboviruses 5-aza-C was effective against two model riboviruses: measles virus and bovine viral diarrhea virus.

Viral Stocks for Test of Antiviral Activity

Measles virus (MV) and bovine viral diarrhea virus (BVDV) are members of two distinct ribovirus families, Paramyxoviridae and Flaviviridae. For primary screening, drug activities were tested against these two viruses.

MV Nagahata strain was used for drug testing. Compared to some laboratory strains, this virus strain replicates lytically in primary human embryonic lung cells and causes extensive cytopathic effect during acute infection. The virus stock was prepared by growing the virus on CV-1 cells at a MOI of 0.01. The titer of the virus stock was determined by plaque formation assay after series dilution.

The BVDV strain used for drug testing was the Singer strain. This virus also causes a cytopathic effect that is measurable and allows estimation of the level of infection. The visible cytopathology can be used as an endpoint for titrating the virus by 50% tissue culture infectious dose ($TCID_{50}$). The BVDV was propagated in bovine turbinate (BT cells). The virus $TCID_{50}$ was determined by counting the cytopathic effect at the endpoint dilution. Briefly, confluent BT cells in 96-well plates were infected with the virus at 8 independent serial 10-fold dilutions. All the plates were incubated for five days at 37° C. in 5% $CO_2$. Each well was scored as positive or negative appearance of visible cytopathic effect. The titers were calculated by the method of Reed and Muench, *Am. J. Hyg.* 27:493-497 (1938), and the mean titer and standard deviation for each of the 3 replicates for each drug concentration and the positive and negative control were calculated.

Treatment of MV- or BVDV-Infected Cells with Mutagenic Nucleoside Analogs

Virus susceptible cells (CV-1 or BT cells) were seeded in 96-well plates at $2\times10^4$ cells/well. The virus was inoculated onto the cell monolayers at a MOI of 0.001~0.002 to keep 30 plaque forming units (pfu) in each well. The inoculum was maintained in 37° C. for about one hour and the supernatant was discarded. Fresh media containing appropriate drug concentration was added in each well. Untreated control was run in parallel. Each drug was tested in triplicate. Three days after infection, cytopathic effect (CPE) was examined in the untreated control wells. When the untreated control cells showed more than 90% CPE, the infected cells were harvested. The plates went through one "freeze-thaw" cycle to release intracellular virus. The virus stock was saved for next round of passage. The virus titer was determined as described above. Virus at a titer of $10^5 \sim 10^6$ pfu/ml was produced by this method.

The following results were obtained. 5-aza-C was effective against BVDV as a surrogate for hepatitis C virus, with an EC50 of 10 µM. 5-aza-C was effective against measles virus with an $EC_{50}$ of 15 µM.

Assessment of the Frequency of Mutations to the Viral Genome Induced by Ribonucleoside Analogs.

The mutagenicity of test analogs showing antiviral activities will be evaluated. Studies with ribavirin indicate that the mutation rate is related to the concentration of introduced analogs (see e.g., Crotty et al., *Nature Med.* 8(12):1375-1379 (2000)). In order to shorten the duration of the experiment, the infected cells are treated with test analogs at 2 mM so that a high mutation rate can be achieved. This dosage is usually toxic to cells and no progeny virus is produced. Cells are inoculated with BVDV or MV and incubated for 4 hours. The incubation allows the virus to express the proteins necessary for viral RNA replication. The test analogs are then added and incubated for another 24 hours. Viral RNA is extracted with a Qiagen RNeasy Kit. About 1 µg of RNA is primed with viral gene specific oligonucleotides and cDNA will be synthesized using M-MLV reverse transcriptase. About 1 kb fragments covering BVDV variable region E2, and conserved region NS3 is amplified from 1 µg cDNA by PCR. The PCR products is cloned into an Invitrogen Topo© cloning vector. A Millipore Miniprep kit is used to screen plasmids containing viral inserts. About 40 positive clones are subjected to sequence reaction. Each sample is sequenced from two directions. Sequence results were assembled by using the DNASTAR Stagman program. Each mutated base is counted and mutation rate is calculated over the total number of sequenced nucleotides. The results are compared with the background control generated from untreated control virus.

Assessment of Cytotoxicity

For each test analog, cytotoxicity is evaluated on BT cells. BT cells are seeded at $1\times10^4$, $4\times10^4$, $1\times10^5$ cells/well in 24-well plates. The next day the cells are treated with drugs at concentrations of 0, 100 µM, 300 µM and 1,000 µM. Each dose is tested in duplicate. After the cells are grown for three generations, MTT at final concentration of 1 µg/µl is added in the media and the cells are incubated for three hours. 10% SDS in 0.02N HCl will be added to lyse the cells overnight. The plates are read on a Tecan Genius microplate reader at wavelengths of 570/650 nm. The dose response curve is graphed by comparing the treated cells with the untreated control. The dosage that inhibits 50% of cell growth ($IC_{50}$) is then determined. For those analogs showing antiviral activity, cytotoxicity is further examined in T lymphoid CEM cells by using the same method.

Example 4

Synthesis

Materials and Methods

5-Azacytidine (1) and 2'-deoxy-5-azacytidine (2) (Scheme 1) are commercially available from Sigma.

5-Azauridine (3)

Compound 3 was synthesized following a literature procedure (Nucl. Acid Chemistry (L. B. Townsend and R. S. Tipson Eds) Part 1, p 455-459, N-Y 1978).

5,6-Dihydro-5-azauridine (4)

Compound 4 was synthesized from 5-azauridine according to (Piskala A., Česneková B., Veselý J. *Nucl. Acids Symp. Ser. No* 18 (1978) pp 57-60).

Example 4a

Synthesis of 1-(2-Deoxy-3,5-di-O-p-toluoyl-β-D-ribofuranosyl)-4-amino-1,2-dihydro-1,3,5-triazin-2-one (5)

The desired compound was synthesized by (Niedballa U., Vorbrüggen H. *J. Org. Chem.* Vol. 39, No. 25, 1974, pp 3672-3674) as a white crystalline powder, m.p. 195-196° (from ethyl acetate).

Example 4b

Synthesis of 1-(2-Deoxy-3,5-di-O-p-toluoyl-α-D-ribofuranosyl)-4-amino-1,2-dihydro-1,3,5-triazin-2-one (6)

The desired compound was isolated as a side reaction product from the above synthesis of compound 5 as a white crystalline powder, m.p. 210-211° (from $CH_2Cl_2$-hexanes), 220° (from ethanol).

NMR (DMSO-$d_6$) δ 8.44 (s, 1H, H-6), 7.91 (d, 2H, Ar), 7.71 (d, 2H, Ar), 7.51 (d J=8.7 Hz, 2H, $NH_2$), 7.36 (d, 2H, Ar), 7.28 (d, 2H, Ar), 6.11 (d J=5.7 Hz, 1H, H-1'), 5.53 (d, 1H, H-4'), 5.11 (t, 1H), 4.45 (d, 2H), 2.86 (m, 1H), 2.50 (m, 1H), 2.39 (s, 3H, Me), 2.37 (s, 3H, Me). NMR (CDCl$_3$) δ 8.25 (s, 1H, H-6), 7.92 (d, 2H, Ar), 7.69 (d, 2H, Ar), 6.88 (br s, 2H, $NH_2$), 7.26 (d, 2H, Ar), 7.19 (d, 2H, Ar), 6.27 (d J=6.3 Hz, 1H, H-1'), 5.61 (d, 1H, H-4'), 4.88 (t, 1H), 4.55 (d, 2H), 3.00-2.87 (m, 1H), 2.67 (m, 1H), 2.42 (s, 3H, Me), 2.38 (s, 3H, Me).

Example 4c

Synthesis of 1-(2-Deoxy-3,5-di-O-p-toluoyl-β-D-ribofuranosyl)-4-amino-1,2,5,6-tetrahydro-1,3,5-triazin-2-one (7) (Scheme 2)

To a suspension of 5 (0.50 g, 1.08 mmol) in acetic acid (5 mL) was added $NaBH_4$ in 2 portions (2×0.040 g, 2.11 mmol) with ice cooling in 15 min interval. The mixture was stirred for another 15 min at 0° C. and evaporated. The residual oil was suspended in CHCl$_3$ (150 mL), washed with sat. $NaHCO_3$ solution (70 mL) and dried over $Na_2SO_4$. The solution was filtered through Celite, concentrated by partial evaporation and applied to a silica gel column (1.5×22 cm). The column was eluted with $CH_2Cl_2$—MeOH mixtures (5-15% v/v MeOH, 700 mL). The product fractions were combined and evaporated, crystallized from MeOH-ether (1:2) giving 0.3 g of 7 as a solid. MS ES$^+$ 467 [M+H$^+$].

Example 4d

Synthesis of 1-(2-Deoxy-3,5-di-O-p-toluoyl-α-D-ribofuranosyl)-4-amino-1,2,5,6-tetrahydro-1,3,5-triazin-2-one (8)

Compound 8 was synthesized by analogy to 7 starting from 6. NMR (DMSO-$d_6$) δ 7.92-7.85 (m, 4H, Ar), 7.38-7.30 (m, 4H, Ar), 6.27 (dd J=8.2+4.8 Hz, 1H, H-1'), 5.46 (m, 1H, H-4'), 4.58 (q, 2H, $CH_2$), 4.56 (m, 1H), 4.37 (m, 2H), 3.5 (br s, 3H, NH, $NH_2$), 2.78 (m, 1H), 2.50 (m, 1H), 2.39 (s, 3H, Me), 2.38 (s, 3H, Me). MS ES$^+$ 467 [M+H$^+$].

Example 4e

Synthesis of 1-(2-Deoxy-β-D-ribofuranosyl)-4-amino-1,2,5,6-tetrahydro-1,3,5-triazin-2-one (2'-deoxy-5,6-dihydro-5-azacytidine) (9)

Method A (Reduction of 2). To a suspension of 2'-deoxy-5-azacytidine (2) (0.045 g, 0.2 mmol) in 96% ethanol (2.9 mL) was added $NaBH_4$ (40 mg, 1.06 mmol), and the mixture was stirred for 10 min at RT. Water (4 mL) was added to the mixture giving a clear solution that was directly used for RP HPLC purification using a gradient of MeCN in 0.1 M triethylammonium bicarbonate buffer. The main fraction after evaporation provided 0.04 g of 9 as a solid. MS ES$^+$ 231 [M+H$^+$].

Method B (Deprotection of 7, scheme 3). To a solution of 7 (50 mg) in MeOH (5 mL) was added 25% aq. $NH_3$ (2 mL) giving a suspension that became a solution upon stirring overnight. The mixture was evaporated, redissolved in water and purified by RP preparative HPLC using a gradient of MeCN in 0.1 M triethylammonium bicarbonate buffer. The main fraction after evaporation gave 0.03 g of 9 as a solid. MS ES$^+$ 231 [M+H$^+$].

Method C (via reduction of ribo-compound 1, scheme 4, five steps).

Step 1. Synthesis of 3',5'-O-(1,1,3,3-tetraisopropyldisiloxane-1,3-diyl)-5-azacytidine (11)

Compound 11 was prepared by analogy to the process described for TIPS-protection of compound 2 in (Goggard A. J., Marquez V. E. *Tetrahedron Letters*, vol. 29, No. 15, 1988, pp 1767-1770). Compound 11 was obtained as a colorless solid with m.p. 249°.

Step 2. Synthesis of 3',5'-O-(1,1,3,3-tetraisopropyldisiloxane-1,3-diyl)-5,6-dihydro-5-azacytidine (12)

0.57 g of 3',5'-O-(1,1,3,3-tetraisopropyldisiloxane-1,3-diyl)-5-azacytidine was suspended in 10 mL of THF under nitrogen. $NaBH_4$ (0.34 g, 9 mmol, 7.7 eq.) was added and the reaction mixture was sonicated for 3 min. After stirring for 2 h at room temperature, 100 mL of saturated NaCl was added and the mixture was extracted 3 times with 150 mL of EtOAc. The organic fractions were dried over $Na_2SO_4$, filtered and evaporated. The product was isolated by silica gel LC in EtOAc with MeOH gradient. MS ES$^-$ 487.0 [M–H$^+$], yield of 12 is 0.27 g (47%).

Step 3. Synthesis of 3',5'-O-(1,1,3,3-tetraisopropyldisiloxane-1,3-diyl)-5,6-dihydro-N$^4$-isobutyryl-5-azacytidine (13) (Scheme 5)

265 mg of 3',5'-O-(1,1,3,3-tetraisopropyldisiloxane-1,3-diyl)-5,6-dihydro-5-azacytidine was dissolved in a 1:1 mix of pyridine and dichloromethane (10 mL) and cooled to 0° C. Chlorotrimethylsilane (344 μL, 5 eq.) was added followed after 15 min by isobutyryl chloride (341 μL, 6 eq.). After 1.5 h of stirring the reaction was quenched with 10 mL of MeOH, evaporated, dissolved in EtOAc (100 mL) and extracted twice with saturated NaCl (50 mL). The organic layer was dried with $Na_2SO_4$, evaporated and the residue was redissolved in MeOH and left overnight at room temperature. Then the solution was evaporated and the product was isolated by flash chromatography (MeOH gradient in dichloromethane). MS ES$^-$ 557.1 [M–H$^+$], yield 180 mg (59%).

Step 4. Synthesis of 3',5'-O-(1,1,3,3-tetraisopropyldisiloxane-1,3-diyl)-2'-deoxy-5,6-dihydro-N$^4$-isobutyryl-5-azacytidine (14)

80 mg of 3',5'-O-(1,1,3,3-tetraisopropyldisiloxane-1,3-diyl)-5,6-dihydro-N$^4$-isobutyryl-5-azacytidine was dissolved in 4 mL of dry DMF and 1,1'-thiocarbonyldiimidazole (77 mg, 3 eq.) was added. After overnight incubation at ambient temperature the reaction mixture was diluted with 50 mL of EtOAc and extracted with water (4×50 mL). The organic fraction was dried over $Na_2SO_4$, filtered, evaporated to oil, coevaporated with toluene twice and dissolved in 10 mL of toluene. The solution was degassed with argon for 45 min, 107 μL of tributyltin hydride (5 eq.) and 13 mg of 2,2'-azobis (isobutyronitrile) were added. The reaction mixture was heated at 80° C. for 3 h, cooled, evaporated and separated by flash chromatography on silica gel (MeOH gradient in dichloromethane). The main product showed expected $ES^+$ MS signals at 543.3 $[M+H^+]$ and 565.5 $[M+Na^+]$, yield 18 mg (23%).

Step 5. Synthesis of 2'-deoxy-5,6-dihydro-5-azacytidine (9)

6 mg of 3',5'-O-(1,1,3,3-tetraisopropyldisiloxane-1,3-diyl)-2'-deoxy-5,6-dihydro-$N^4$-isobutyryl-5-azacytidine was dissolved in 2 mL of MeOH and treated with 6 mL of 25% aq. $NH_3$ over 16 h at room temperature. The solution was evaporated to dryness, coevaporated with toluene and dissolved in 2 mL of THF. To the solution 0.5 mL of 1 M tetrabutylammonium fluoride was added and the reaction mixture was incubated for 1 h. Solvent was removed by evaporation and the product was isolated on RP HPLC. Appropriate fractions were pooled, evaporated to dryness, co-evaporated with MeOH and the product was repurified on a preparative TLC plate (1×250×250 mm, elution with isopropanol—water—conc. $NH_4OH$ (15:4:1)). The product-containing band was scratched out and the product was eluted with MeOH-water (7:3) mixture. MS $ES^+$ 231.0 $[M+H^+]$, 253.2 $[M+Na^+]$, yield 1.7 mg (67%). MS $ES^+$ 231 $[M+H^+]$.

Example 4f

Synthesis of 1-(2-Deoxy-α-D-ribofuranosyl)-4-amino-1,2,5,6-tetrahydro-1,3,5-triazin-2-one (10)

Compound 10 was synthesized by analogy to the preparation of 9 by deprotection of 8 with ammonia using method B. Compound 10 was obtained as a solid.

Example 4g

Synthesis of 3',5'-O-(1,1,3,3-Tetraisopropyldisiloxane-1,3-diyl)-5,6-dihydro-$N^4$-isobutyryl-5-aza-5-N-methylcytidine (15)

18 mg of 3',5'-O-(1,1,3,3-tetraisopropyldisiloxane-1,3-diyl)-2'-deoxy-5,6-dihydro-$N^4$-isobutyryl-5-azacytidine, 0.1 mL of N,N-diisopropyl-N-ethylamine and 1.0 mL of dimethylsulfate were incubated for 1 h at room temperature. The product was isolated by flash chromatography on silica gel (MeOH gradient in dichloromethane). $ES^+$ MS signals at 573.2 $[M+H^+]$, 595.3 $[M+Na^+]$ and 1167.2 $[2M+Na^+]$, yield 14 mg (77%).

Example 4h

Synthesis of 5,6-Dihydro-5-aza-5-N-methylcytidine (16)

14 mg of 3',5'-O-(1,1,3,3-tetraisopropyldisiloxane-1,3-diyl)-5,6-dihydro-$N^4$-isobutyryl-5-aza-5-N-methylcytidine was dissolved in 2 mL of MeOH and treated with 6 mL of concentrated $NH_4OH$ during 16 h at room temperature. The solution was evaporated to dryness, co-evaporated with toluene and dissolved in 2 mL of THF. To the solution 0.5 mL of 1 M tetrabutylammonium fluoride was added and the reaction mixture was incubated for 1 h. Solvent was removed by evaporation and the product was isolated on RP HPLC. Appropriate fractions were pooled, evaporated to dryness, coevaporated with MeOH and the product was repurified on a preparative TLC plate (1×250×250 mm, elution with isopropanol(15):water(4):conc. $NH_4OH(1)$). The band containing product was scratched out and the product was eluted with MeOH(7):water(3) mixture. MS $ES^+$ 261.0 $[M+H^+]$, 520.9 $[2M+H^+]$, yield 5.5 mg (86%). MS/MS of the 261.0 mass ion generated the expected fragment with m/z 128.9, corresponding to the 5,6-dihydro-5-aza-5-N-methylcytosine base.

Example 4i

Synthesis of 3',5'-O-(1,1,3,3-Tetraisopropyldisiloxane-1,3-diyl)-2'-deoxy-5,6-dihydro-$N^4$-isobutyryl-5-aza-5-N-methylcytidine (17)

A mixture of 3',5'-O-(1,1,3,3-tetraisopropyldisiloxane-1,3-diyl)-2'-deoxy-5,6-dihydro-$N^4$-isobutyryl-5-azacytidine (14) (11 mg), 0.1 mL of N,N-diisopropyl-N-ethylamine and 1.0 mL of dimethylsulfate was incubated for 1 h at room temperature. The product 17 was isolated by flash chromatography on silica gel (MeOH gradient in dichloromethane). $ES^+$ MS signals at 557.3 $[M+H^+]$ and 579.3 $[M+Na^+]$, yield 9 mg (80%).

Example 4j

Synthesis of 2'-Deoxy-5,6-dihydro-5-aza-5-N-methylcytidine (18)

A solution of 3',5'-O-(1,1,3,3-tetraisopropyldisiloxane-1,3-diyl)-2'-deoxy-5,6-dihydro-$N^4$-isobutyryl-5-aza-5-N-methylcytidine (17) (9 mg) in MeOH (2 mL) was treated with concentrated $NH_4OH$ (6 mL) and kept at room temperature for 16 h. The solution was evaporated to dryness, coevaporated with toluene, dissolved in THF (2 mL) and treated with a solution of 1 M tetrabutylammonium fluoride in THF (0.5 mL). The reaction mixture was left at room temperature for 1 h. Solvent was removed by evaporation and the product was isolated on RP HPLC. Appropriate fractions were pooled, evaporated to dryness, coevaporated with MeOH and the product was further purified on a preparative TLC plate (1×250×250 mm, elution with isopropanol—water—conc. $NH_4OH$ (15:4:1)). The product-containing band was scratched out and the product was eluted with MeOH-water (7:3) mixture. MS $ES^+$ 245.0 $[M+H^+]$, 267.1 $[M+Na^+]$, yield 18 was 3.7 mg (93%). MS/MS of the 245.0 mass ion generated the expected fragment with m/z 128.9, corresponding to the 5,6-dihydro-5-aza-5-N-methylcytosine base.

Example 4k

Synthesis of 6-Methyl-5-azacytosine (19) (Scheme 6)

8.4 g of dicyandiamide was suspended in a mixture of 16 mL of $Ac_2O$ and 1 mL of AcOH. The reaction mixture was refluxed during 16 h. After cooling the reaction mixture was evaporated to dryness. The product was isolated on preparative RP HPLC ($CH_3CN$ gradient 0-20% over 20 min in 0.1 M triethylammonium bicarbonate buffer (pH 7.0)). Retention time was 6.7 min, λmax=237 nm, MS ES⁻=125, yield 30%.

Example 4l

6-Methyl-5-azacytidine (20)

Compound 20 was synthesized according to (Hanna N. B., Zajicek J., Piskala A. *Nucleosides & Nucleotides* 16, 1997, p. 129-144) with 8% yield starting from 6-methyl-5-azacytosine (19).

Example 4m

Synthesis of 6-Methyl-2'-deoxy-5-azacytidine (21)

30 mg of 6-methyl-5-azacytosine, 5 mg of $(NH_4)_2SO_4$ and 5 mL of hexamethyldisilazane were refluxed overnight at 125° C. (external oil bath temperature). The clear solution was evaporated to solid and co-evaporated with 5 ml of xylene. To the residue 70 mg of the 3,5-bistoluoyl-1-chloro-2-deoxyribose was added and the mixture was suspended in 2 mL of $CH_3CN$. Incubation with stirring was continued for 24 h and then a mixture of 173 mg AcONa and 0.3 mL AcOH, diluted to 1 mL with water was added. After 1 h the mixture was diluted with 20 ml of water and extracted twice with 20 mL of ethyl acetate. The organic layer was dried over $Na_2SO_4$, filtered, evaporated and the products were separated by silica gel chromatography. Yield of β-anomer 25%, α-anomer (23%).

The protected nucleoside was treated with 0.02 M NaOMe in MeOH for 4 h to remove toluoyl protecting groups. The resulting nucleosides were isolated on PR HPLC.

Example 4n

Syntheses of 6-phenyl-5-azacytosine (22) and 6-phenyl-5-azacytidine (23)

(Scheme 7) were carried out according to published procedure (Hanna N. B., Masojidkova M., Fiedler P., Piskala A. *Collect. Czech. Chem. Commun.* 63, 1998, p. 222-230). Yield of the base was 43%, nucleoside—16%.

Example 4o

Synthesis of 5-azacytidine and 6-methyl-5-azacytidine prodrugs (Scheme 8)

8.3 mg of the nucleoside was suspended in 1 mL of THF and 11 uL (4 eq.) of N-methylimidazole was added. The reaction mixture was cooled to −78° C. and 4-bromophenyl-N-methoxyalaninylphosphorochloridate (15 mg) in 0.5 mL of THF was added dropwise during 30 min. After 1 h another 10 mg of the phosphorochloridate was added, the mixture was allowed to warm to room temperature and incubated overnight. The mixture was evaporated and separated by RP HPLC. 5-Azacytidine prodrug was eluted at 23 min (0-20% $CH_3CN$ in 23 min), λmax=226 nm, yield approximately 15%. 6-Methyl-5-azacytidine prodrug was eluted at 24 min, λ max 225 nm, yield approximately 12%.

The 5-Azacytidine phospholipid prodrugs are synthesized by scheme 9. 5-Azacytidine prodrugs, activated by biological reduction are synthesized by scheme 10.

Example 4p 1-(β-D-Ribofuranosyl)-4-amino-1,2,5,6-tetrahydro-1,3,5-triazin-2-one (5,6-Dihydro-5-azacytidine) (23) and 6-oxo-5-azacytidine (24) (Scheme 11) were synthesized by (Beisler, J. A., Abbasi, M. M., Kelley, J. A., Driscoll, J. S. *J Carbohydrates. Nucleosides. Nucleotides,* 4(5), 1977, pp 281-299).

Example 4q

2'-Deoxy-5,6-dihydro-5-azauridine (26) is synthesized by a reduction of 2'-deoxy-5-azauridine (25) by analogy to the reduction of compound 3 to 4 (Piskala A., ČesnekováB., Veselý J. *Nucl. Acids Symp. Ser. No* 18 (1978) pp 57-60).

Example 4r

Synthesis of 2'-deoxy-5,6-dihydro-5-azacytidine Palmitate (27)

To a solution of (9) (0.26 g, 1.13 mmol) in MeOH (50 mL) was added a solution of palmitic acid (0.29 g, 1.13 mmol) in hot MeOH (10 mL) and evaporated. The residue was triturated with ether and filtered giving 0.57 g (quantitative yield) of a colorless product with m.p. 123-124°. MS ES+ 231 [M+H⁺].

Example 5

In Vitro Assays Demonstrate that DHAdC is Safe and Effective Against HIV Infection In Vitro Passaging Assays of DHAdC Passaging experiments were performed for DHAdC (also referred to as SN1212), to demonstrate that viral eradication is possible in vitro. The experiment was carried out in quadruplicate in the presence of SN11212 at a concentration of 100 nM. Levels of p24 fell permanently below the limit of detection (4 ng/ml) by passage 8. No infectious virus was recovered after passage 12. (Data not shown.)

DHAdC is a Viral Mutagen.

Assessment of DHAdC viral mutagenicity was carried out as described above for 5-aza-dC. Mutagenesis of the sense strand of a 0.9 kb fragment of reverse transcriptase of HIV NL4-3 was determined after a single passage in SN1212 (50 μM) and compared to an untreated control. Results are shown in Table 5.

TABLE 5

| Analog | Mutations/Nucleotide | % | G→A A→G | T→C C→T | A→T T→A | A→C C→A | G→T T→G | G→C C→G |
|---|---|---|---|---|---|---|---|---|
| SN1212 | 37/24,828 | 0.015 | 17 | 12 | 1 | 1 | 3 | 3 |
| Control | 32/28,658 | 0.011 | 27 | 3 | 0 | 1 | 1 | 0 |

The mutation rate induced by 50 μM SN1212 in HIV RT is 1.4-fold higher than control (0.0015 in DHAdC treated versus 0.0011 in control). The dominant mutations are C⇌T transitions (enhanced 4.6-fold by SN1212), with a minority of transversions (pyrimidine⇌purine). In contrast, 5-OH-dC demonstrated only a 1.14-fold increase in overall mutation rate over background.

DHAdC does not Cause Significant Mutagenesis of Cellular DNA.

SN1212 is a poor substrate for polymerase-α, the cellular polymerase responsible for most DNA synthesis. (Data not shown.) An hgprt assay was also performed to test mutagenesis of cellular DNA by DHAdC. The assay was performed on CHO (Chinese Hamster Ovary) cells and mutants were selected for resistance to 6-thioguanine (6-TG). EMS (ethyl methyl sulfonate), a known mutagen, was used as a positive control. SN1212 at a concentration of 1 mM did not increase above background the mutation frequency of a cellular gene, hgprt. (Data not shown.) Of note, the $EC_{50}$ of DHAdC against HIV is in the range of 10 nM, while no significant mutation to cellular DNA is noted at 1 mM, a 10,000-fold difference.

Mitochondrial toxicity is also a safety concern with nucleoside analogs. SN1212 was also analyzed for mitochondrial toxicity. SN1212 does not demonstrate evidence of mitochondrial toxicity by either an increase in lactate production or inhibition of mitochondrial DNA at the highest dose tested, 320 µM. (Data not shown.)

DHAdC is Effective Against Wild-Type HIV Strains and NRTI Resistant HIV Strains.

The effectiveness of DHAdC was tested against wild-type HIV strains and NRTI resistant HIV strains as described in Example 2. The following strains were tested: HIV-1 LAI, wild-type; HIV-1 LAI-M184V-M184V mutation with resistance to lamivudine (3TC); HIV-1 RTMDR1-74V, 41L, 106A and 215Y mutations with resistance to zidovudine, didanosine, nevirapine and other non-nucleoside reverse transcriptase inhibitors; and HIV-1 RTMC-67N, 70R, 215F and 219Q with resistance to zidovudine. Results are shown in Table 6.

TABLE 6

| HIV Strain | SN1212 ($EC_{50}$) µM | AZT ($EC_{50}$) nM | 3TC ($EC_{50}$) nM |
| --- | --- | --- | --- |
| Wild-type | 6 | 10 | 45 |
| RTMC | 6 | 300 | 330 |
| M184V | 6 | 10 | >32,000 |
| RTMDR1 | 6 | 60 | N.D. |

The $EC_{50}$'s of SN1212 were the same in wild-type and the three mutant HIV strains, confirming the lack of cross-resistance between SN1212 and NRTI. Furthermore, based on HIV passaging experiments designed to favor the emergence of resistant strains performed with SN1212, it appears unlikely that de novo resistance will develop to SN1212.

Example 6

In Vivo Assays Demonstrate that DHAdC, or Prodrugs Thereof, are Safe and Effective Against HIV Infection DHAdC is Effective in Treating HIV Infections in a Mouse Model SN1212 was administered at up to 100 mg/kg/day subcutaneously in SCID-Hu Thy/Liv mice for 21 days, without any significant toxicity being demonstrated. After completion of this toxicology experiment, SN1212 was tested in HIV infected SCID-Hu mice. While SN1212 did not demonstrate reduction in p24 or HIV RNA, it demonstrated a significant decrease in viral infectivity when compared to untreated animals at a dose of 10 mg/kg (see, e.g., Table 7). The discordance between viral infectivity and conventional surrogate markers of viral load, such as p24 or HIV RNA, is not surprising, as it has also been observed in vitro, and reflects the increased proportion of non-infectious viral particles in the presence of SN1212. It is also interesting to note that, of the treated groups, the immunologic profile of the SN1212 groups most closely resemble that of the uninfected group. This is compatible with the finding that infection with less "fit" viruses provides a relative clinical benefit by preserving cellular immunity.

TABLE 7

| Drug/Dose (mg/kg/day) | CD4+ CD8+ (%) | CD4+ (%) | CD8+ (%) | p24 (pg/$10^6$ cells) | HIV-1 RNA (log copies/ $10^6$ cells) | Viral liter (viruses/ $10^6$ cells) |
| --- | --- | --- | --- | --- | --- | --- |
| SN1212 (100) | 63 | 10 | 11 | 570 | 5.1 | 24.9 |
| SN1212 (10) | 70 | 13 | 9.5 | 510 | 5.3 | 15.2** |
| 3TC (30) | 77 | 6.9 | 4.2 | 0** | 2.0** | 0** |
| NDC* | 63 | 7.9 | 5.9 | 250 | 5.4 | 66.5 |
| Uninfected | 65 | 12 | 9.4 | 0 | 0 | 0 |

*No drug control.
**$p < 0.05$

A Prodrug of SN1212, SN1461, is not Toxic in Animals.

SN1461 is a prodrug that in humans is converted predominantly in the liver to SN1212. SN1461 has been tested for pharmacokinetic characteristics in a number of animal species. In rats, SN1461 has a half-life of 3.9 hours and an oral bioavailability of 43%, while in beagles; SN1461 has a half-life of 2.1 hours and an oral bioavailability of 51%, prior to formulation enhancements. A single dose of up to 1 g/kg of SN1461 has been given orally to rats and up to 2 g/kg to dogs in a dose escalation study without evidence of toxicity.

The present invention provides a novel class of mutagenic compounds, and methods of using and preparing these compounds. While specific examples have been provided, the above description is illustrative and not restrictive. Any one or more of the features of the previously described embodiments can be combined in any manner with one or more features of any other embodiments in the present invention. Furthermore, many variations of the invention will be apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document, Applicants do not imply that any particular reference is "prior art" to their invention.

What is claimed is:

1. A compound having the formula:

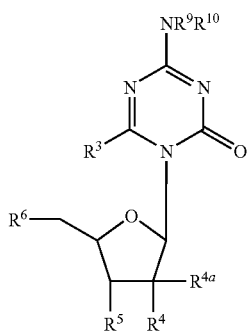

wherein
   $R^9$ is substituted or unsubstituted acyl;
   $R^{10}$ is selected from H, and substituted or unsubstituted alkyl;
   $R^3$ is H;
   $R^4$ is H;
   $R^5$ is OH;
   $R^6$ is OH; and
   $R^8$ is H.

2. A formulation of the compound according to claim 1, and a second compound having the formula:

A-B wherein
   A is a hydrophobic domain; and
   B is a hydrophilic domain covalently bound to A.

3. The formulation according to claim 2, further comprising a polycationic species.

4. The formulation according to claim 3, wherein said polycationic species is a dendrimeric polyamine.

5. The formulation according to claim 2, wherein said formulation is an aqueous formulation.

6. The compound according to claim 1, having the formula:

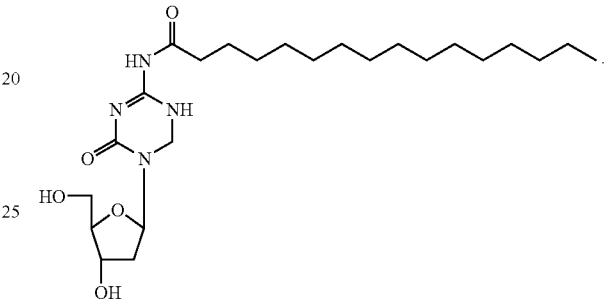

7. The compound according to claim 1, wherein $R^{10}$ is H.

* * * * *

UNITED STATES PATENT AND TRADEMARK OFFICE
CERTIFICATE OF CORRECTION

PATENT NO.         : 7,772,197 B2
APPLICATION NO.    : 10/670915
DATED              : August 10, 2010
INVENTOR(S)        : Richard Daifuku et al.

It is certified that error appears in the above-identified patent and that said Letters Patent is hereby corrected as shown below:

In the Claims:
In column 63, claim 1, please delete the current compound formula shown below:

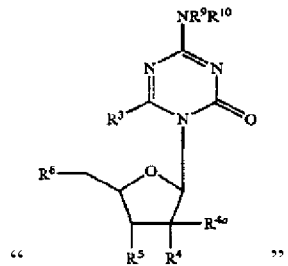

and insert the following compound formula:

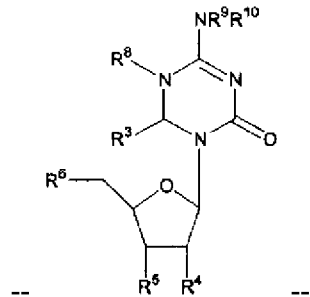

Signed and Sealed this
First Day of May, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,772,197 B2 | Page 1 of 1 |
| APPLICATION NO. | : 10/670915 | |
| DATED | : August 10, 2010 | |
| INVENTOR(S) | : Richard Daifuku et al. | |

It is certified that error appears in the above-identified patent and that said Letters Patent is hereby corrected as shown below:

<u>Title page:</u>

In the Assignee data (73), please replace "1,3,5-Triazines for Treatment of Viral Diseases" with --Koronis Pharmaceuticals, Inc.--

Signed and Sealed this
Sixteenth Day of October, 2012

David J. Kappos
*Director of the United States Patent and Trademark Office*